(12) United States Patent
Dhuper et al.

(10) Patent No.: US 10,525,228 B2
(45) Date of Patent: Jan. 7, 2020

(54) MODULAR PULMONARY TREATMENT SYSTEM

(71) Applicant: AEON RESEARCH AND TECHNOLOGY, INC., Hewlett, NY (US)

(72) Inventors: Sunil Kumar Dhuper, Old Westbury, NY (US); Greg Marler, Rockford, IL (US)

(73) Assignee: AEON RESEARCH AND TECHNOLOGY, Hewlett, NY (US)

( * ) Notice: Subject to any disclaimer, the term of this patent is extended or adjusted under 35 U.S.C. 154(b) by 592 days.

(21) Appl. No.: 15/291,679

(22) Filed: Oct. 12, 2016

(65) Prior Publication Data

US 2017/0100558 A1 Apr. 13, 2017

Related U.S. Application Data

(62) Division of application No. 13/747,095, filed on Jan. 22, 2013, now Pat. No. 9,498,592.
(Continued)

(51) Int. Cl.
*A61M 16/20* (2006.01)
*A61M 11/00* (2006.01)
(Continued)

(52) U.S. Cl.
CPC .......... *A61M 16/208* (2013.01); *A61M 16/06* (2013.01); *A61M 16/0816* (2013.01);
(Continued)

(58) Field of Classification Search
CPC ......... A62B 18/00; A62B 18/02; A62B 18/10; A62B 7/00; A62B 9/02; A61M 11/00;
(Continued)

(56) References Cited

U.S. PATENT DOCUMENTS

| | | |
|---|---|---|
| 2,110,557 A | 3/1938 | Dunlap |
| 2,335,085 A | 11/1943 | Roberts |

(Continued)

FOREIGN PATENT DOCUMENTS

| | | |
|---|---|---|
| GB | 880 824 | 10/1961 |
| GB | 2 407 043 | 4/2005 |

(Continued)

*Primary Examiner* — Joseph D. Boecker
(74) *Attorney, Agent, or Firm* — Leason Ellis LLP

(57) ABSTRACT

A patient interface system for delivering a gas to a patient includes a patient interface device that includes at least one inhalation valve and at least one exhalation valve. The system also includes a venturi device that has at least one port for connection to a gas source. The venturi device has at least one primary air entrainment window and at least one secondary air entrainment window which is downstream of the at least one primary air entrainment window. The inhalation valve is disposed between: (1) the main body and (2) the primary and secondary air entrainment windows of the venturi device. At least one of the primary air entrainment window and secondary air entrainment window includes a means for closing the respective window, thereby changing a degree at which the respective window is open and changing a flow rate of the air flowing through the respective window.

23 Claims, 45 Drawing Sheets

Related U.S. Application Data

(60) Provisional application No. 61/694,020, filed on Aug. 28, 2012, provisional application No. 61/610,828, filed on Mar. 14, 2012, provisional application No. 61/589,671, filed on Jan. 23, 2012.

(51) Int. Cl.

| | | |
|---|---|---|
| *A61M 15/00* | (2006.01) | |
| *A61M 16/06* | (2006.01) | |
| *A61M 16/08* | (2006.01) | |
| *A61M 16/10* | (2006.01) | |
| *A61M 16/12* | (2006.01) | |
| *A61M 16/14* | (2006.01) | |
| *A61M 16/00* | (2006.01) | |

(52) U.S. Cl.
CPC .... *A61M 16/0833* (2014.02); *A61M 16/0875* (2013.01); *A61M 16/1045* (2013.01); *A61M 16/12* (2013.01); *A61M 16/127* (2014.02); *A61M 16/20* (2013.01); *A61M 16/209* (2014.02); *A61M 16/0078* (2013.01); *A61M 16/14* (2013.01); *A61M 2202/0208* (2013.01)

(58) Field of Classification Search
CPC .. A61M 15/00; A61M 16/00; A61M 16/0078; A61M 16/06; A61M 16/08; A61M 16/0816; A61M 16/0833; A61M 16/0875; A61M 16/1045; A61M 16/12; A61M 16/122; A61M 16/125; A61M 16/127; A61M 16/14; A61M 16/20; A61M 16/208; A61M 16/209
See application file for complete search history.

(56) References Cited

U.S. PATENT DOCUMENTS

| | | | |
|---|---|---|---|
| 2,796,295 A | 6/1957 | McKinnon | |
| 2,906,265 A | 9/1959 | Samuels | |
| 2,990,563 A | 7/1961 | Davidson | |
| 3,057,347 A | 10/1962 | McGee | |
| 3,097,642 A * | 7/1963 | Russell | A61M 16/06 128/205.17 |
| 3,104,062 A | 9/1963 | Mahon | |
| D198,964 S | 8/1964 | Dash et al. | |
| 3,184,115 A | 5/1965 | Meshberg | |
| D206,979 S | 2/1967 | Jaffe | |
| D207,143 S | 3/1967 | Goodwin | |
| 3,666,955 A | 5/1972 | Suprenant et al. | |
| 3,794,072 A | 2/1974 | Diedrich et al. | |
| 3,826,413 A | 7/1974 | Warren | |
| D233,845 S | 12/1974 | Fettel et al. | |
| 3,903,884 A | 9/1975 | Huston et al. | |
| 3,977,432 A | 8/1976 | Vidal | |
| 4,011,865 A | 3/1977 | Morishita | |
| 4,114,811 A | 9/1978 | Loeffler | |
| 4,121,580 A | 10/1978 | Fabish | |
| D251,203 S | 2/1979 | Williamson | |
| 4,190,046 A | 2/1980 | Virag | |
| 4,210,155 A | 7/1980 | Grimes | |
| D258,535 S | 3/1981 | Reichl | |
| 4,291,688 A | 9/1981 | Kistler | |
| D262,320 S | 12/1981 | Mono | |
| 4,303,063 A * | 12/1981 | Stahl | A61B 5/02216 601/37 |
| D264,940 S | 6/1982 | Stock | |
| D272,094 S | 1/1984 | Wolf et al. | |
| 4,463,755 A | 8/1984 | Suzuki | |
| 4,470,412 A | 9/1984 | Nowacki et al. | |
| 4,554,916 A | 11/1985 | Watt | |
| 4,584,998 A | 4/1986 | McGrail | |
| 4,620,538 A | 11/1986 | Koegel | |
| 4,637,528 A | 1/1987 | Wachinski et al. | |
| 4,641,644 A | 2/1987 | Andersson et al. | |
| 4,648,628 A | 3/1987 | Meadows et al. | |
| 4,649,912 A | 3/1987 | Collins | |
| 4,669,463 A | 6/1987 | McConnell | |
| 4,711,378 A | 12/1987 | Anderson | |
| D294,175 S | 2/1988 | Briggs | |
| 4,739,756 A | 4/1988 | Horn | |
| 4,821,714 A | 4/1989 | Smelser | |
| 4,823,784 A | 4/1989 | Bordoni et al. | |
| 4,830,224 A | 5/1989 | Brison | |
| 4,850,371 A | 7/1989 | Broadhurst et al. | |
| D304,232 S | 10/1989 | Fuller | |
| D307,183 S | 4/1990 | Kalayjian | |
| 4,919,132 A | 4/1990 | Miser | |
| D308,576 S | 6/1990 | Iversen | |
| 4,951,661 A | 8/1990 | Sladek | |
| 4,953,545 A | 9/1990 | McCarty | |
| 5,012,803 A | 5/1991 | Foley et al. | |
| 5,020,530 A | 6/1991 | Miller | |
| 5,039,134 A | 8/1991 | Meadow et al. | |
| 5,078,131 A | 1/1992 | Foley | |
| 5,099,833 A | 3/1992 | Michaels | |
| 5,119,809 A | 6/1992 | Gerson | |
| D328,244 S | 7/1992 | Hamilton et al. | |
| 5,146,916 A | 9/1992 | Catalani | |
| 5,146,936 A | 9/1992 | Ng | |
| D335,175 S | 4/1993 | Sladek | |
| 5,231,983 A | 8/1993 | Matson et al. | |
| 5,263,485 A | 11/1993 | Hickey | |
| 5,277,175 A | 1/1994 | Riggs et al. | |
| 5,287,849 A | 2/1994 | Piper et al. | |
| 5,349,946 A | 9/1994 | McComb | |
| 5,357,946 A | 10/1994 | Kee et al. | |
| 5,385,140 A | 1/1995 | Smith | |
| 5,388,571 A | 2/1995 | Roberts et al. | |
| 5,438,982 A | 8/1995 | MacIntyre | |
| 5,464,043 A * | 11/1995 | Damia | A61M 16/208 137/556.6 |
| 5,479,920 A | 1/1996 | Piper et al. | |
| 5,482,031 A | 1/1996 | Lambert | |
| 5,504,224 A | 4/1996 | Wilson | |
| 5,513,630 A | 5/1996 | Century | |
| 5,540,218 A | 7/1996 | Jones | |
| 5,542,412 A | 8/1996 | Century | |
| 5,546,930 A | 8/1996 | Wikefeldt | |
| 5,570,686 A | 11/1996 | Century | |
| 5,579,758 A | 12/1996 | Century | |
| 5,586,551 A | 12/1996 | Hilliard | |
| 5,588,424 A | 12/1996 | Insler et al. | |
| 5,594,987 A | 1/1997 | Century | |
| 5,606,789 A | 3/1997 | Century | |
| 5,613,489 A | 3/1997 | Miller et al. | |
| 5,617,844 A | 4/1997 | King | |
| 5,628,305 A | 5/1997 | Melker | |
| 5,640,951 A | 6/1997 | Huddart et al. | |
| 5,642,730 A | 7/1997 | Baran | |
| 5,660,167 A | 8/1997 | Ryder | |
| 5,701,886 A | 12/1997 | Ryatt | |
| 5,727,542 A | 3/1998 | King | |
| 5,738,087 A | 4/1998 | King | |
| 5,752,502 A | 5/1998 | King | |
| 5,791,340 A | 8/1998 | Schleufe et al. | |
| 5,813,423 A | 9/1998 | Kirchgeorg | |
| 5,816,240 A | 10/1998 | Komesaroff | |
| 5,848,587 A | 12/1998 | King | |
| 5,848,588 A | 12/1998 | Foley et al. | |
| 5,865,172 A | 2/1999 | Butler et al. | |
| 5,964,223 A | 10/1999 | Baran | |
| 5,988,162 A | 11/1999 | Retallick, III | |
| 6,039,042 A | 3/2000 | Sladek | |
| 6,041,777 A | 3/2000 | Faithfull et al. | |
| 6,078,730 A | 6/2000 | Huddart et al. | |
| 6,079,413 A | 6/2000 | Baran | |
| 6,116,233 A | 9/2000 | Denyer et al. | |
| 6,116,242 A | 9/2000 | Frye | |
| 6,192,884 B1 | 2/2001 | Vann et al. | |
| 6,340,023 B2 | 1/2002 | Elkins | |
| 6,357,437 B1 | 3/2002 | Jacques | |
| 6,363,932 B1 | 4/2002 | Forchione et al. | |
| 6,390,090 B1 | 5/2002 | Piper | |

(56) References Cited

U.S. PATENT DOCUMENTS

| | | |
|---|---|---|
| 6,427,685 B1 | 8/2002 | Ray |
| 6,450,163 B1 | 9/2002 | Blacker et al. |
| 6,478,026 B1 | 11/2002 | Wood |
| 6,494,202 B2 | 12/2002 | Farmer |
| 6,550,476 B1 | 4/2003 | Ryder |
| 6,584,969 B2 | 7/2003 | Farmer |
| 6,612,308 B2 | 9/2003 | Stenzler et al. |
| 6,622,725 B1 | 9/2003 | Fisher et al. |
| 6,679,252 B2 | 1/2004 | Sladek |
| 6,705,316 B2 | 3/2004 | Blythe et al. |
| 6,718,979 B1 | 4/2004 | Britt et al. |
| 6,748,945 B2 | 6/2004 | Grychowski et al. |
| 6,772,754 B1 | 8/2004 | Mendenhall |
| 6,776,160 B2 | 8/2004 | Wang |
| 6,799,423 B2 | 10/2004 | Piekarski |
| 6,929,003 B2 | 8/2005 | Blacker et al. |
| 6,976,488 B2 | 12/2005 | Halperin |
| 6,994,083 B2 | 2/2006 | Foley et al. |
| 7,036,500 B2 | 5/2006 | Niles et al. |
| 7,080,643 B2 | 7/2006 | Grychowski et al. |
| 7,131,439 B2 | 11/2006 | Blacker et al. |
| 7,191,776 B2 | 3/2007 | Niles et al. |
| 7,204,245 B2 | 4/2007 | Johnson et al. |
| 7,290,541 B2 | 11/2007 | Ivri et al. |
| 7,360,541 B2 | 4/2008 | Dhuper et al. |
| 7,445,006 B2 | 11/2008 | Dhuper et al. |
| 7,493,898 B2 | 2/2009 | King |
| 7,669,595 B1 | 3/2010 | Mitchell |
| 7,743,764 B2 | 6/2010 | Dhuper et al. |
| 7,841,341 B2 | 11/2010 | Dhuper et al. |
| 7,841,342 B2 | 11/2010 | Dhuper et al. |
| 7,861,713 B2 | 1/2011 | Dhuper et al. |
| 7,870,857 B2 | 1/2011 | Dhuper et al. |
| 7,926,484 B2 | 4/2011 | Dhuper et al. |
| 8,074,649 B2 | 12/2011 | Dhuper et al. |
| 8,181,646 B2 | 5/2012 | Dhuper et al. |
| 8,534,280 B2 | 9/2013 | Dhuper et al. |
| 8,616,200 B2 | 12/2013 | McKinnon et al. |
| 9,186,474 B1 | 11/2015 | Rollins, III |
| 2002/0017302 A1 | 2/2002 | Fukunaga et al. |
| 2002/0069870 A1 | 6/2002 | Farmer |
| 2002/0121275 A1 | 9/2002 | Johnson et al. |
| 2002/0129814 A1 | 9/2002 | Sladek |
| 2003/0010336 A1 | 1/2003 | Vito |
| 2003/0024533 A1 | 2/2003 | Sniadach |
| 2003/0209246 A1 | 11/2003 | Schroeder et al. |
| 2004/0011364 A1 | 1/2004 | Dhuper et al. |
| 2004/0024372 A1 | 2/2004 | Grogan |
| 2004/0060560 A1 | 4/2004 | Stenzler et al. |
| 2004/0084048 A1 | 5/2004 | Stenzler et al. |
| 2004/0123974 A1 | 7/2004 | Marler et al. |
| 2004/0226563 A1 | 11/2004 | Xu et al. |
| 2004/0234610 A1 | 11/2004 | Hall et al. |
| 2005/0028811 A1 | 2/2005 | Nelson et al. |
| 2005/0039747 A1 | 2/2005 | Fukunaga et al. |
| 2005/0092325 A1 | 5/2005 | Dionne |
| 2005/0092329 A1 | 5/2005 | Sta-Maria |
| 2005/0205098 A1 | 9/2005 | Lampotang et al. |
| 2005/0247313 A1 | 11/2005 | Niles et al. |
| 2006/0231090 A1 | 10/2006 | King |
| 2006/0231091 A1 | 10/2006 | Camarillo |
| 2006/0249158 A1 | 11/2006 | Dhuper et al. |
| 2006/0260607 A1 | 11/2006 | Dhuper et al. |
| 2007/0062531 A1 | 3/2007 | Fisher et al. |
| 2007/0068516 A1 | 3/2007 | Dhuper et al. |
| 2007/0137644 A1 | 6/2007 | Dhuper et al. |
| 2007/0163592 A1 | 7/2007 | Reinstadtler |
| 2007/0221221 A1* | 9/2007 | Cooke ............... A61M 16/209 128/204.18 |
| 2008/0087280 A1 | 4/2008 | Dhuper et al. |
| 2008/0190436 A1 | 8/2008 | Jaffe |
| 2008/0210242 A1 | 9/2008 | Burk |
| 2009/0126723 A1 | 5/2009 | Dhuper |
| 2009/0151728 A1 | 6/2009 | McConnell |
| 2009/0173348 A1 | 7/2009 | Fisher et al. |
| 2009/0235928 A1 | 9/2009 | Borsari |
| 2009/0260628 A1 | 10/2009 | Flynn, Sr. |
| 2009/0293881 A1* | 12/2009 | Graham ............... A61M 11/06 128/207.12 |
| 2010/0071693 A1 | 3/2010 | Allum et al. |
| 2011/0011474 A1 | 1/2011 | Duncan |
| 2011/0073111 A1 | 3/2011 | Stone |
| 2011/0226250 A1 | 9/2011 | LaBollita |
| 2011/0277754 A1 | 11/2011 | Mckinnon et al. |
| 2012/0325205 A1* | 12/2012 | Allum ............... A61M 16/0666 128/201.13 |
| 2013/0192597 A1 | 8/2013 | McKinnon et al. |

FOREIGN PATENT DOCUMENTS

| | | |
|---|---|---|
| RU | 2009113454 | 11/2010 |
| SU | 175623 | 1/1966 |
| WO | WO 2012/128990 | 9/2012 |

* cited by examiner

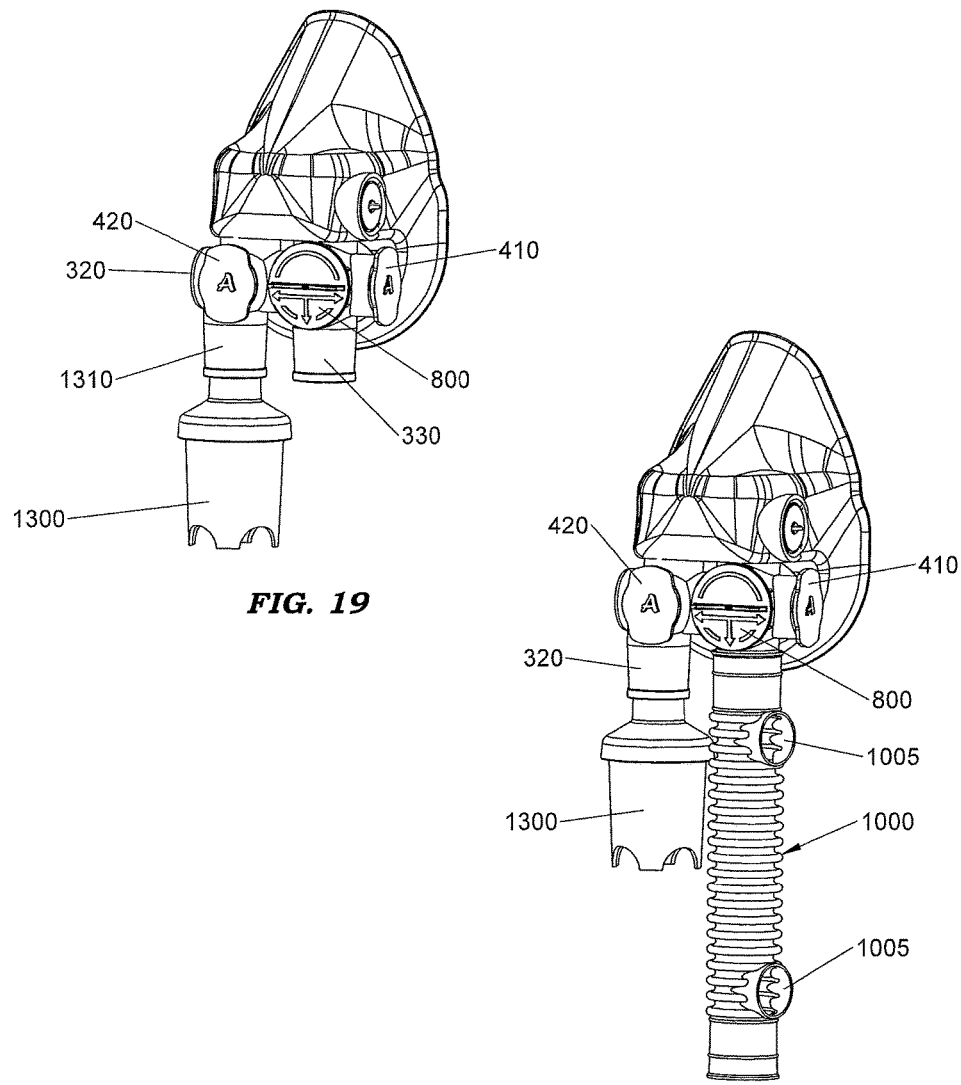

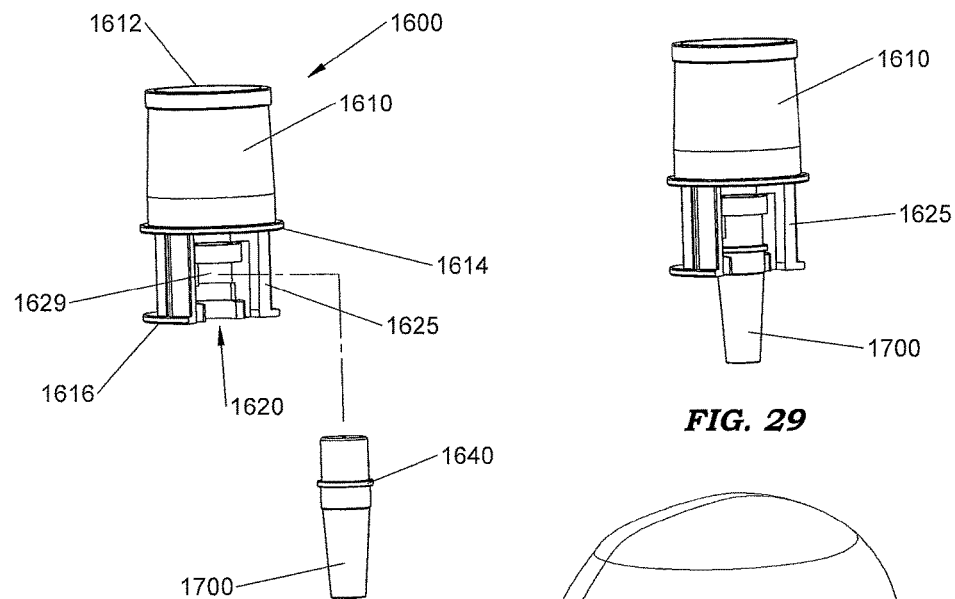
FIG. 28
FIG. 29
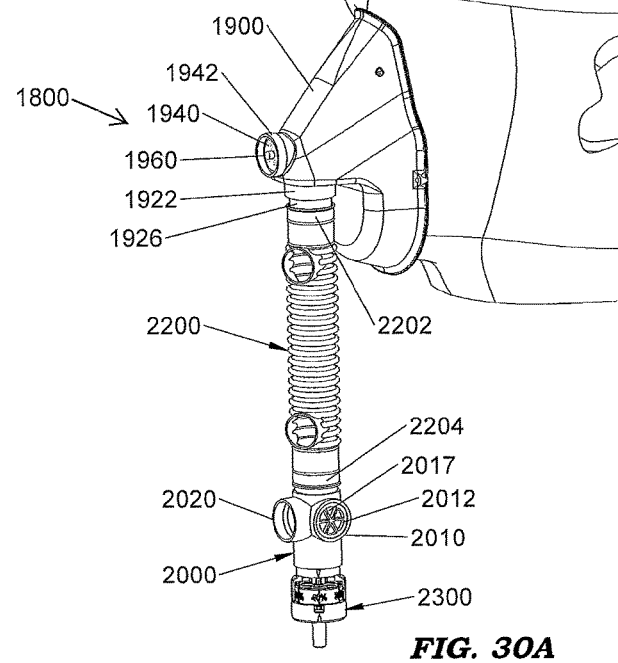
FIG. 30A

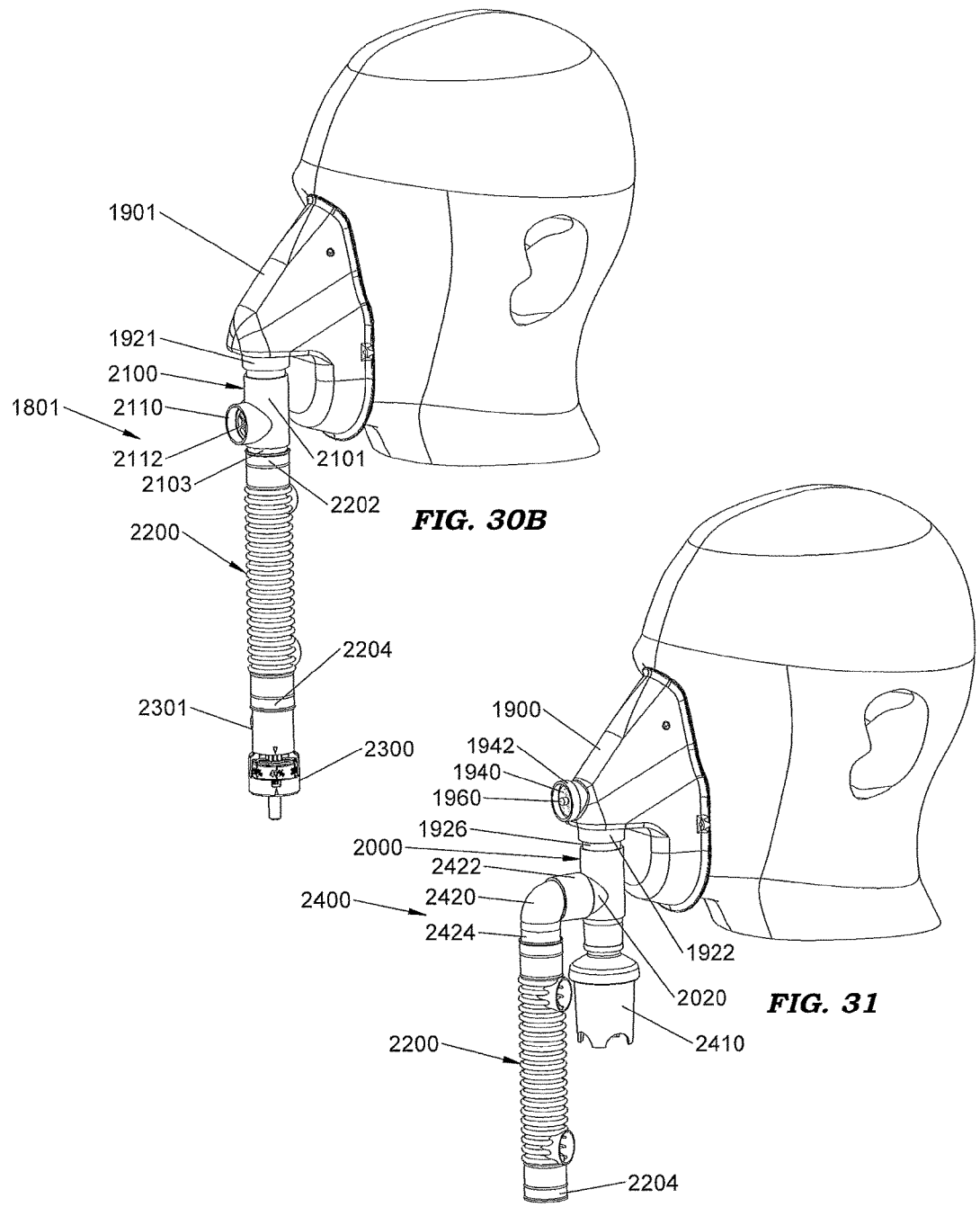

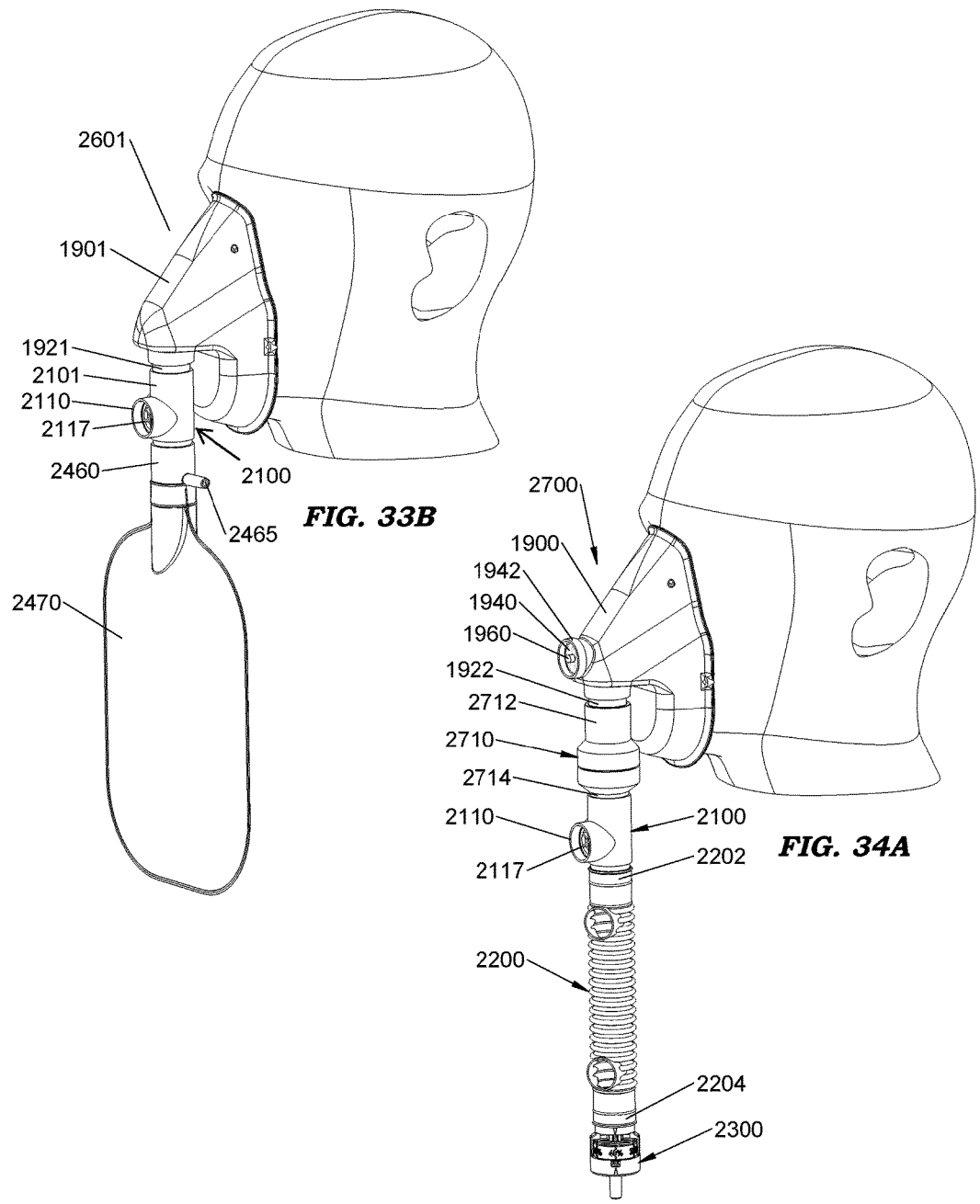

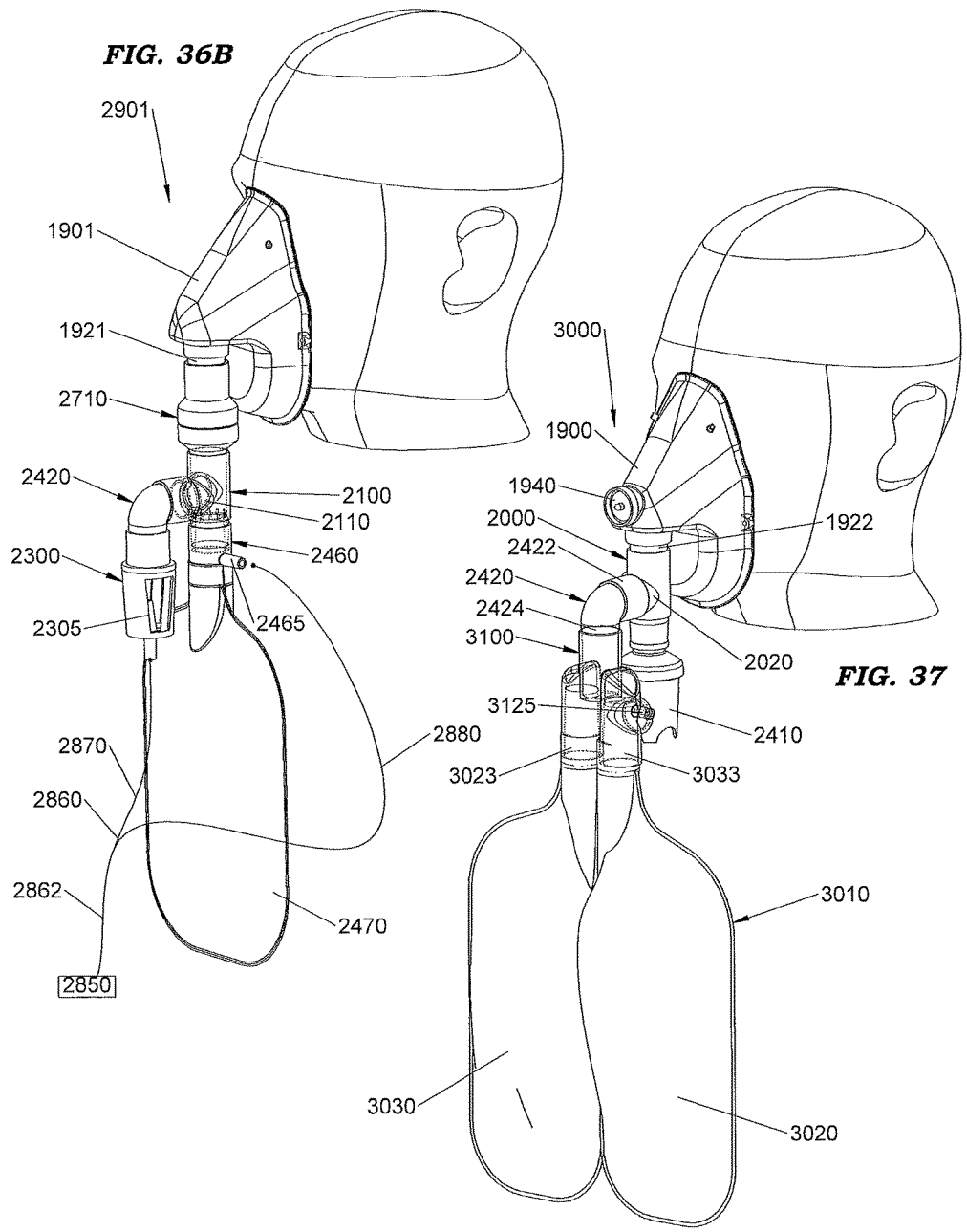

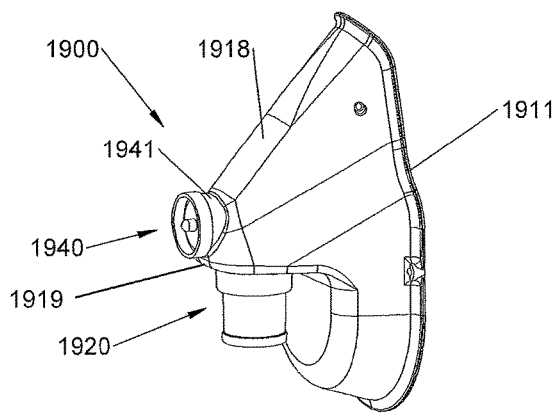
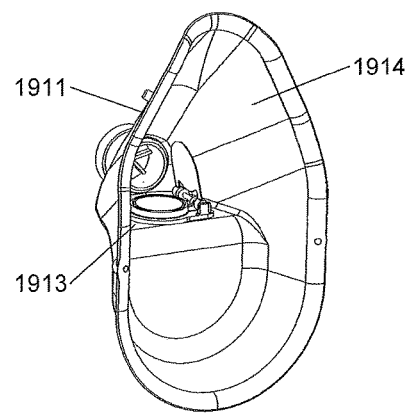
FIG. 38B  FIG. 38C
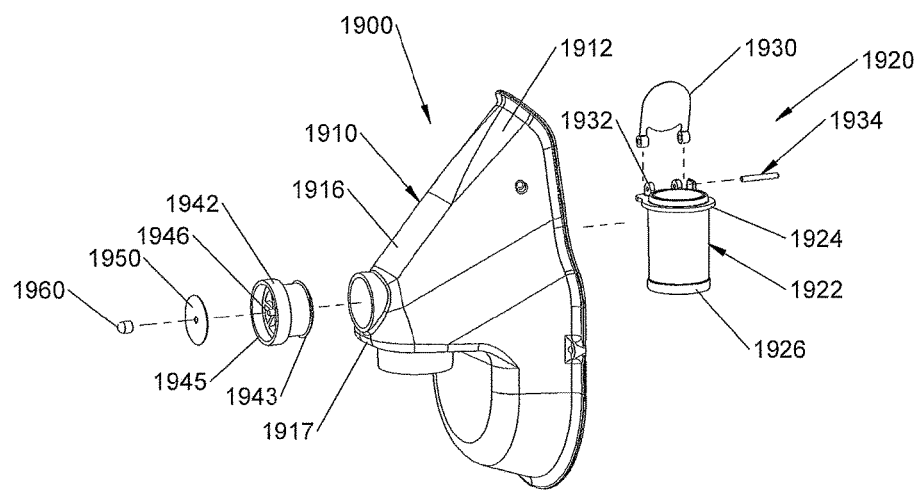
FIG. 38A

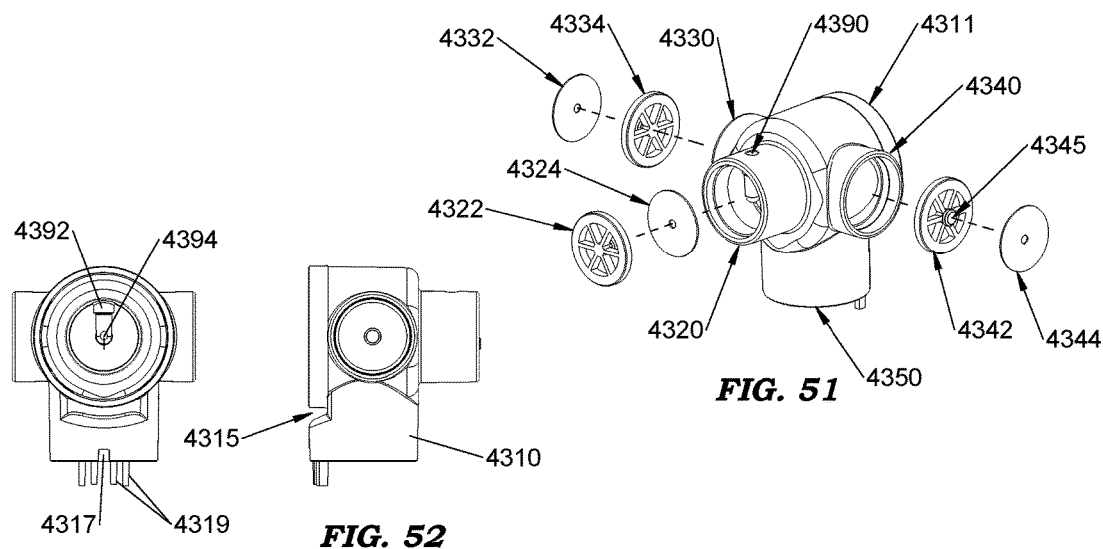
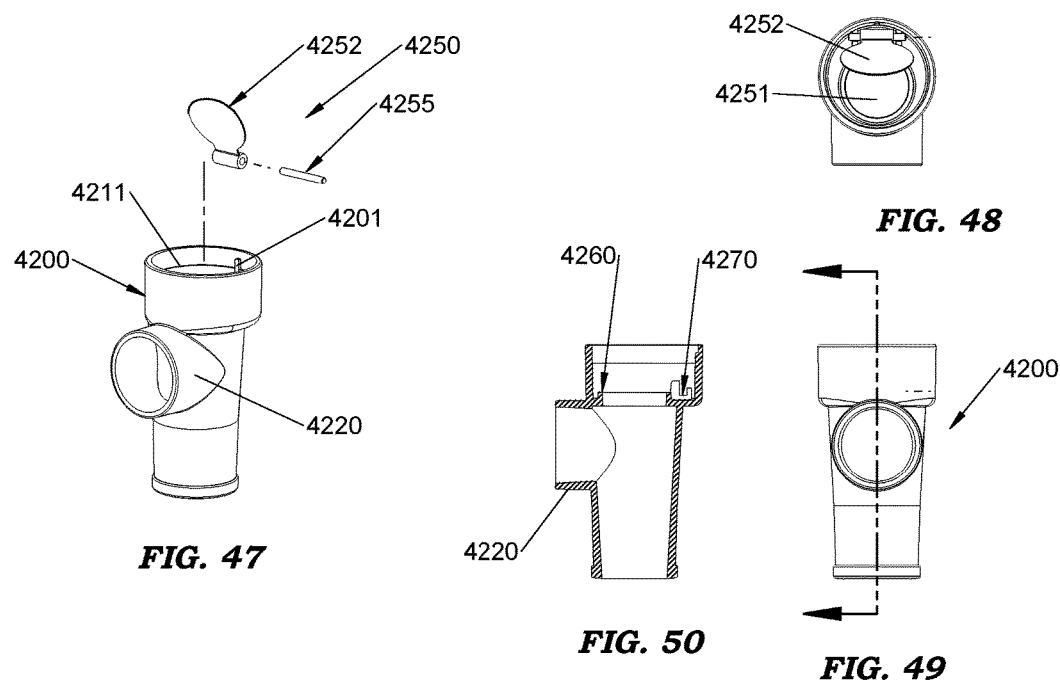

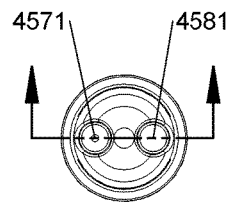 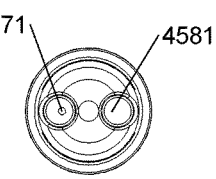 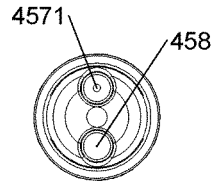 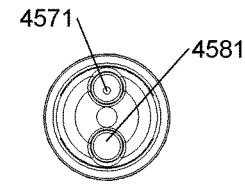
*FIG. 61*  *FIG. 64*  *FIG. 66*  *FIG. 68*
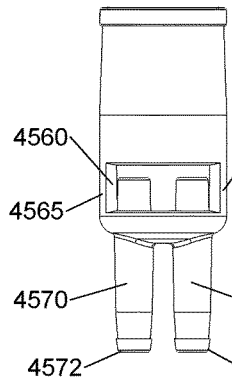 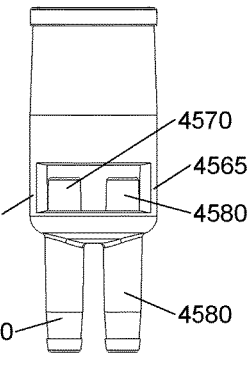 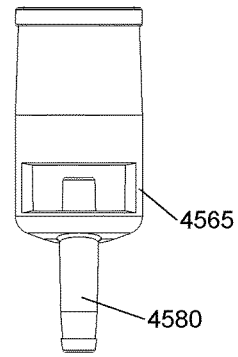 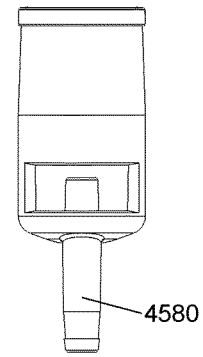
*FIG. 60*  *FIG. 63*  *FIG. 65*  *FIG. 67*
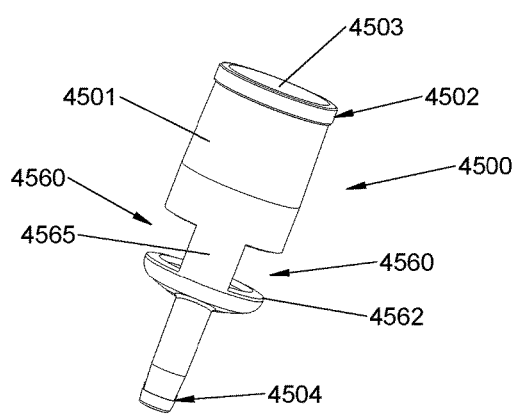 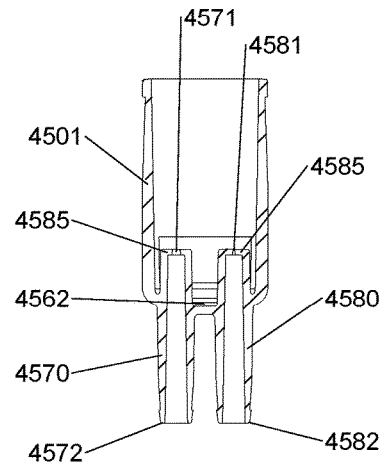
*FIG. 59*  *FIG. 62*

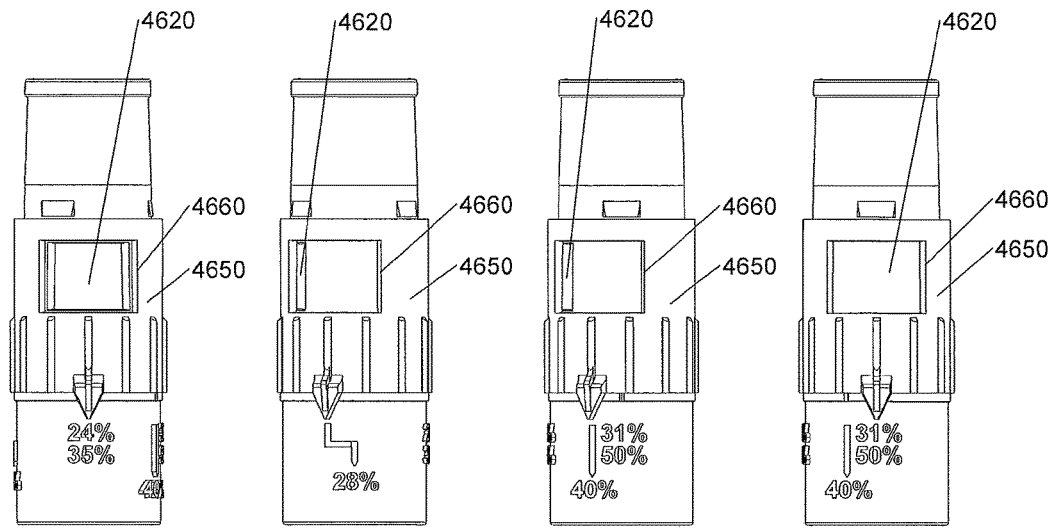
*FIG. 70A*   *FIG. 70B*   *FIG. 70C*   *FIG. 70D*
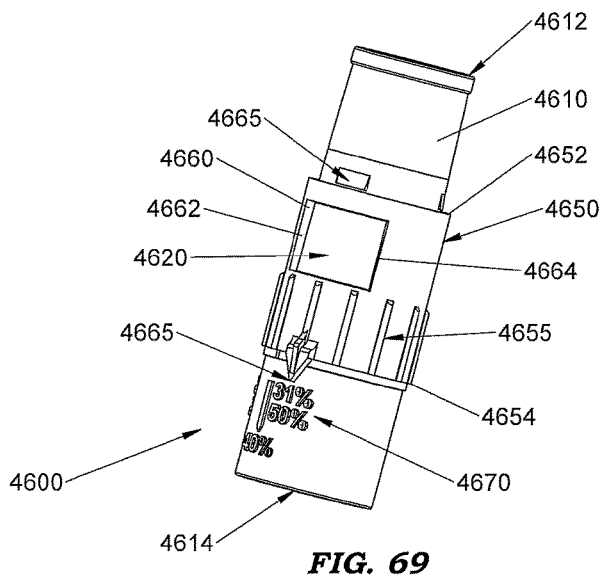
*FIG. 69*

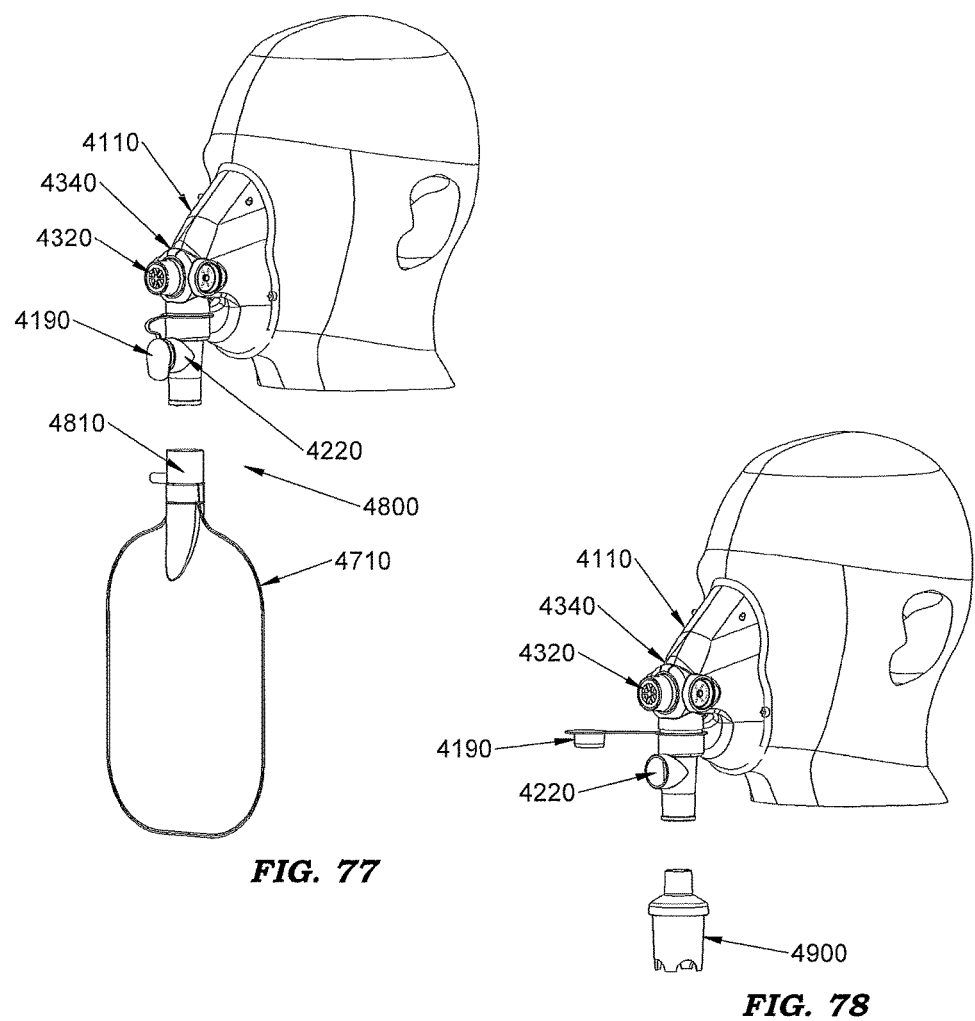

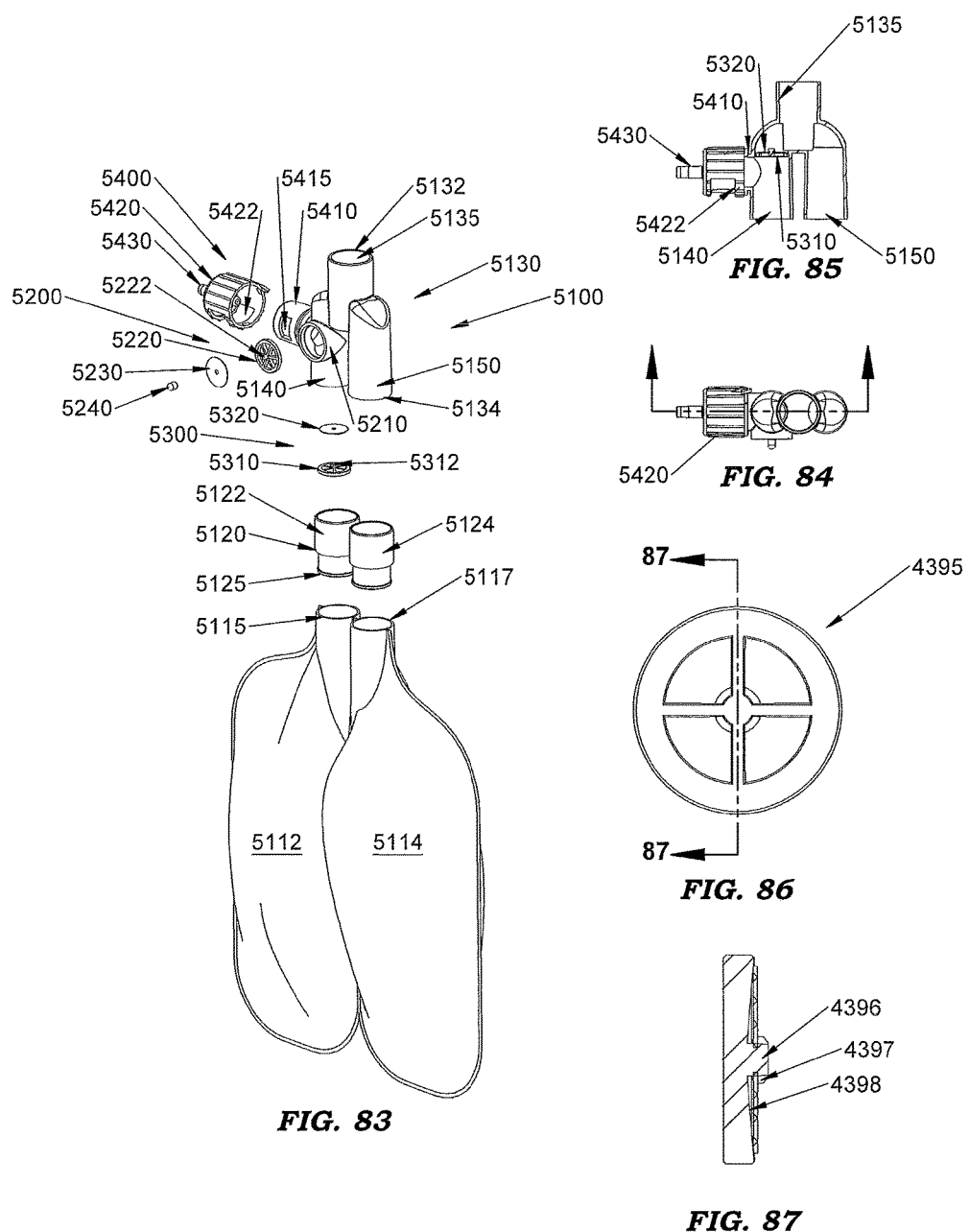

MODULAR PULMONARY TREATMENT SYSTEM

CROSS-REFERENCE TO RELATED APPLICATIONS

The present application is a divisional of U.S. Ser. No. 13/747,095, filed Jan. 22, 2013, which claims the benefit of: U.S. patent application Ser. No. 61/589,671, filed on Jan. 23, 2012; U.S. patent application No. 61/610,828, filed Mar. 14, 2012 and U.S. patent application No. 61/694,020, filed Aug. 28, 2012, each of which is hereby incorporated by reference in its entirety.

TECHNICAL FIELD

The present invention relates to pulmonary treatment equipment and more particularly, relates to a modular pulmonary treatment system that includes a number of interchangeable parts that allow the system to have a number of different operating modes including but not limited to delivery of a gas to a patient; delivery of an aerosolized medication (drug) to a patient; and a combination thereof.

BACKGROUND

Respiratory care devices are commonly used as a means to deliver gases and medication in an aerosolized form to a patient. Aerosolized medication is typically used to treat patients with respiratory conditions, such as reactive airways disease, asthma, bronchitis, emphysema, or chronic obstructive pulmonary disease (COPD), bronchiectasis, cystic fibrosis, etc.

It is generally accepted that effective administration of aerosolized medication depends on the delivery system and its position in relation to the patient. Aerosol particle deposition is influenced by particle size, ventilatory pattern, and airway architecture, and effective medication response is influenced by the dose of the medication used.

An aerosol delivery system includes three principal elements, namely a generator, a power source, and an interface. Generators include small volume nebulizers (SVN), large volume nebulizers (LVN), metered dose inhalers (MDI), and dry powder inhalers (DPI). The power source is the mechanism by which the generator operates or is actuated and includes compressed gas for SVN and LVN and self-contained propellants for MDI. The interface is the conduit between the generator and the patient and includes spacer devices/accessory devices with mouthpieces or face masks. Depending on the patient's age (ability) and coordination, various interfaces are used in conjunction with SVN and MDI in order to optimize drug delivery.

The three primary means for delivering aerosolized medication to treat a medical condition is an MDI, a DPI, or a nebulizer. MDI medication (drug) canisters are typically sold by manufacturers with a boot that includes a nozzle, an actuator, and a mouthpiece. Patients can self-administer the MDI medication using the boot alone but the majority of patients have difficulty synchronizing the actuation of the MDI canister with inhalation causing oropharyngeal drug deposition, decreased drug delivery and therefore effectiveness, and causes other adverse effects.

A dry powder inhaler (DPI) is a device that delivers medication to the lungs in the form of a dry powder. DPIs are an alternative to the aerosol based inhalers commonly called metered-dose inhaler (or MDI). The DPIs may require some procedure to allow a measured dose of powder to be ready for the patient to take. The medication is commonly held either in a capsule for manual loading or a proprietary form from inside the inhaler. Once loaded or actuated, the operator puts the mouthpiece of the inhaler into their mouth and takes a deep inhalation, holding their breath for 5-10 seconds. There are a variety of such devices. The dose that can be delivered is typically less than a few tens of milligrams in a single breath since larger powder doses may lead to provocation of cough. Most DPIs rely on the force of patient inhalation to entrain powder from the device and subsequently break-up the powder into particles that are small enough to reach the lungs. For this reason, insufficient patient inhalation flow rates may lead to reduced dose delivery and incomplete deaggregation of the powder, leading to unsatisfactory device performance. Thus, most DPIs have a minimum inspiratory effort that is needed for proper use and it is for this reason that such DPIs are normally used only in older children and adults.

Small volume nebulizers (SVN) and large volume nebulizers (LVN) have been used to overcome difficulties encountered with MDI and DPI during acute exacerbation of obstructive airways disease but even these devices are fraught with problems especially significant waste of medication and not adequately reaching the target airways.

Problems with prior art devices include that the devices are inefficient and significantly waste medication, they provide a non-uniform concentration of delivered medication, they are expensive, and they are difficult to use. In addition, multiple pieces of equipment are needed to treat a plurality of different conditions.

The modular pulmonary treatment system of the present invention overcomes these deficiencies and provides a system that includes a number of interchangeable parts that allow the system to have a number of different operating modes including but not limited to delivery of a gas to a patient; delivery of an aerosolized medication (drug) to a patient; and a combination thereof.

SUMMARY

According to one embodiment, a patient interface device for delivering a gas to a patient includes a main body for placement against a face of the patient for delivering the gas to the patient. The main body includes a conduit portion that is open at a first end to a hollow interior of the main body and a free second end for attachment to another object in a sealed manner. The device also includes: (1) at least one exhalation valve assembly that is disposed within a first port formed in the main body and includes an exhalation valve member that is configured to vent exhaled air when open; (2) a primary inhalation valve assembly that is disposed within the conduit portion and includes a primary valve member that moves between open and closed positions; and (3) a secondary inhalation valve assembly that is disposed within a second port formed in the main body and includes a secondary valve member that moves between open and closed positions.

The body includes an HME (heat moisture exchange) seat for receiving an HME unit and being located in relationship to the least one primary inhalation valve assembly and the at least one exhalation valve assembly to: (1) allow passage of inhaled gas, that flows through the primary inhalation valve assembly, through the HME seat before flowing into the hollow interior of the main body and to the patient and (2) allow passage of exhaled gas from the patient through the HME seat before exiting to atmosphere through the at least one exhalation valve assembly. The HME seat is at least partially defined by a wall that is integral to the main body and defines a hollow space for receiving the HME unit, the wall being constructed for mating with the HME unit for the secure, yet releasable, attachment of the HME unit to the HME seat.

According to another embodiment, a patient interface system for delivering a gas to a patient includes a patient interface device that includes a main body for placement against a face of the patient for delivering the gas. The patient interface device includes at least one inhalation valve and at least one exhalation valve. The system also includes a venturi device that is fluidly connected to the free second end of the conduit portion. The venturi device has at least one port for connection to a gas source. The venturi device has at least one primary air entrainment window and at least one secondary air entrainment window which is downstream of the at least one primary air entrainment window and thus closer to the main body of the patient interface device. The at least one inhalation valve is disposed between: (1) the main body and (2) the primary and secondary air entrainment windows of the venturi device. At least one of the primary air entrainment window and secondary air entrainment window includes a means for closing the respective window, thereby changing a degree at which the respective window is open and changing a flow rate of the air flowing through the respective window.

In another embodiment, a patient interface system for delivering a gas to a patient includes a patient interface device for delivering a gas to a patient. The patient interface device includes a main body for placement against a face of the patient. The main body includes a conduit portion that is open at a first end to a hollow interior of the main body and a free second end for attachment to another object in a sealed manner. The patient interface delivery device also includes: (1) at least one exhalation valve assembly that is disposed within a first port formed in the main body and includes an exhalation valve member that is configured to vent exhaled air when open; (2) a primary inhalation valve assembly that is disposed within the conduit portion and includes a primary valve member that moves between open and closed positions; and (3) a secondary inhalation valve assembly that is disposed within a second port formed in the main body and includes a secondary valve member that moves between open and closed positions. The system also includes a first accessory that is fluidly attached to the conduit portion.

The primary inhalation valve assembly has a first flow resistance associated therewith and the second inhalation valve assembly has a second flow resistance associated therewith which is greater than the primary inhalation valve assembly and as a result, the secondary inhalation valve assembly acts as an emergency inhalation valve.

The first accessory can be any number of different pieces of equipment including but not limited to a reservoir member, a device for delivering gas and/or aerosolized medication, etc.

BRIEF DESCRIPTION OF THE DRAWING FIGURES

FIG. 19 is a front perspective view of the patient interface system of FIG. 1 attached to a nebulizer for aerosol drug delivery;

FIG. 20 is a front perspective view of the patient interface system of FIG. 19 in further combination with an expandable conduit for aerosol drug delivery;

FIG. 28 is an exploded perspective view of cassette style venturi connector according to one embodiment;

FIG. 29 is a perspective view of the cassette style venturi connector assembly in the assembled state;

FIG. 30A is a side perspective view of a patient interface system according to another embodiment for low concentration gas delivery;

FIG. 30B is a side perspective view of a patient interface system according to another embodiment for low concentration gas delivery;

FIG. 31 is a side perspective view of a patient interface system according to another embodiment for standard dose aerosol drug delivery;

FIG. 33B is a side perspective view of a patient interface system according to another embodiment for 100% non-rebreather gas (oxygen) delivery FIG. 34A is a side perspective view of a patient interface system according to another embodiment for low concentration gas (oxygen) delivery with heat and moisture exchange;

FIG. 36B is a side perspective view of a patient interface system according to another embodiment for high concentration gas (oxygen) delivery with heat and moisture exchange;

FIG. 37 is a side perspective view of a patient interface system according to another embodiment for high dose drug delivery with 100% oxygen or other premixed gas like heliox delivery;

FIG. 38A is an exploded perspective view of a patient interface mask system with valves for use in some of the systems of FIGS. 30-37;

FIG. 38B is a perspective view of the system of FIG. 38A in the assembled condition;

FIG. 38C is a rear perspective view of the system of FIG. 38A;

FIG. 47 is a perspective view of the primary gas valve assembly with a valve member shown exploded therefrom;

FIG. 48 is a top plane view of the primary gas valve assembly;

FIG. 49 is a side elevation view of the primary gas valve assembly;

FIG. 50 is a cross-sectional view of the primary gas valve assembly taken along the lines 50-50 of FIG. 49;

FIG. 51 is an exploded perspective view of the patient interface-mask valve assembly;

FIG. 52 is a side elevation view of the patient interface-mask valve assembly;

FIG. 53 is a front elevation view of the patient interface-mask valve assembly;

FIG. 59 is a side perspective view of a multi-port venturi member that is part of the venturi assembly of FIG. 58;

FIG. 60 is a side elevation view of the multi-port venturi member of FIG. 59 and according to a first embodiment;

FIG. 61 is a top plan view of the multi-port venturi member of FIG. 60;

FIG. 62 is a cross-sectional view of the multi-port venturi member taken along the lines 62-62 of FIG. 61;

FIG. 63 is a side elevation view of the multi-port venturi member according to a second embodiment;

FIG. 64 is a top plan view of a multi-port venturi member of FIG. 63;

FIG. 65 is a side elevation view of the multi-port venturi member according to a third embodiment;

FIG. 66 is a top plan view of a multi-port venturi member of FIG. 65;

FIG. 67 is a side elevation view of the multi-port venturi member according to a fourth embodiment;

FIG. 68 is a top plan view of a multi-port venturi member of FIG. 67;

FIG. 69 is a side perspective view of a secondary gas entrainment valve member that is part of the assembly of FIG. 58;

FIG. 70A is a side elevation showing the secondary gas entrainment valve member in a fully open position;

FIG. 70B is a side elevation showing the secondary gas entrainment valve member in a partially open position;

FIG. 70C is a side elevation showing the secondary gas entrainment valve member in a partially open position;

FIG. 70D is a side elevation showing the secondary gas entrainment valve member in a fully closed position;

FIG. 77 is an exploded perspective view of a respiratory treatment system for a 100% non-breather gas delivery;

FIG. 78 is an exploded perspective view of a respiratory treatment system for standard dose aerosol drug delivery;

FIG. 83 is an exploded perspective view of the high dose aerosol drug delivery/gas delivery mechanism of FIG. 82;

FIG. 84 is a top plan view of the system of FIG. 83;

FIG. 85 is a cross-sectional view taken along the line 85-85 of FIG. 84;

FIG. 86 is a top plan view of a valve seat in accordance with a different embodiment of the present invention; and FIG. 87 is a cross-sectional view taken along the lines 87-87 in FIG. 86.

DETAILED DESCRIPTION OF CERTAIN EMBODIMENTS

Figure 1:
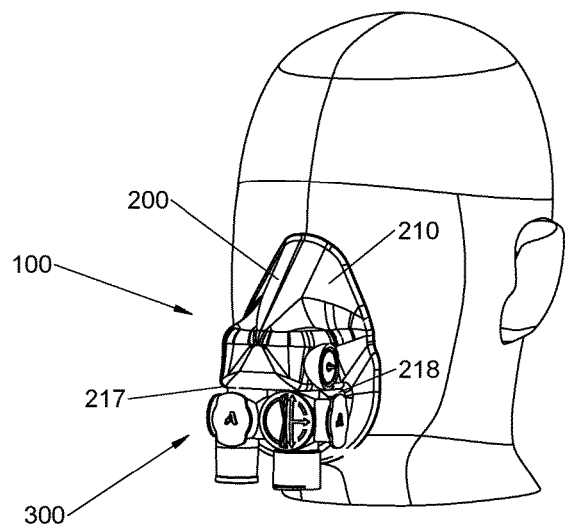
FIG. 1 is a front and side perspective view of a patient interface system/modular pulmonary treatment system according to one embodiment and configured for delivery of gases to a patient including aerosolized medication.
Figure 2:
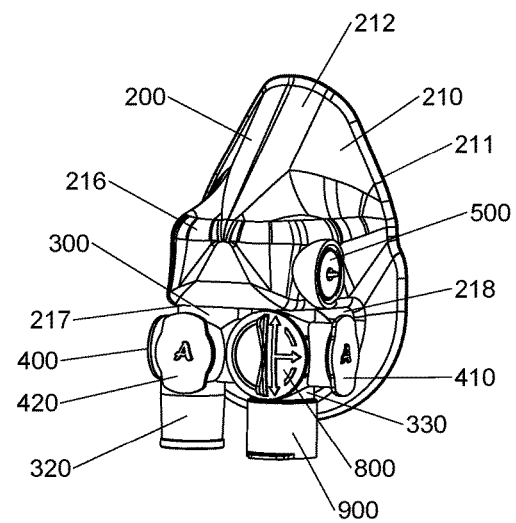
FIG. 2 is a close-up perspective view of the patient interface system/modular pulmonary treatment system of FIG. 1.

FIGS. 1-7 illustrate a patient interface/modular pulmonary treatment system 100 in accordance with one embodiment of the present invention. The system 100 is formed of a number of components that mate together to form the assembled system 100 and in particular, the patient interface system 100 includes a face mask 200 and a primary treatment module valve assembly 300 that intimately mates with the face mask 200.

The illustrated face mask 200 is merely exemplary in nature and it will therefore be understood that any number of different face mask geometries/constructions can be utilized. The face mask 200 includes a face mask body 210 that has a front surface or face 212 and an opposite rear surface or face 214. The face mask body 210 includes a nose portion 216 that is defined by a planar underside wall 217 and a front planar portion 218. The planar underside wall 217 and the front planar portion 218 generally are formed at a right angle. The face mask body 210 has a peripheral edge 211 that seats and seals against the face of a user.

Figure 3:
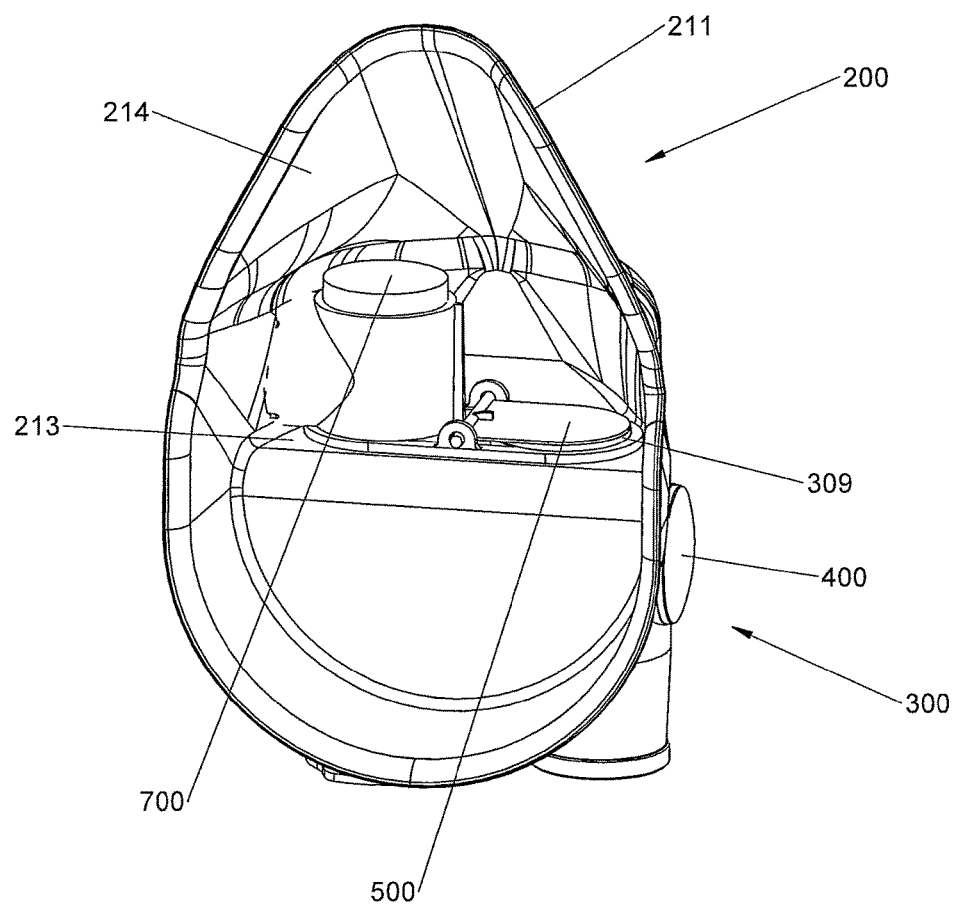
FIG. 3 is a rear perspective view of the patient interface system/modular pulmonary treatment system of FIG. 1.
Figure 4:
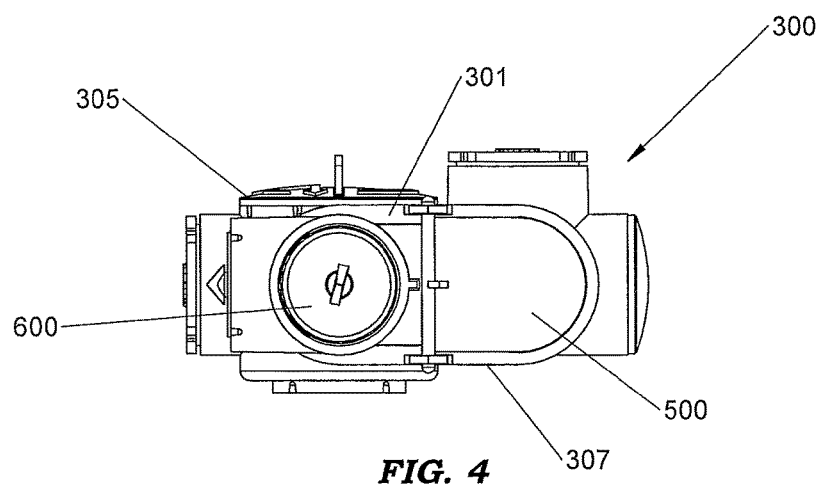
FIG. 4 is a top plan view of a patient interphase valve assembly according to one embodiment for use with a facemask as shown in FIG. 1.
Figure 5:
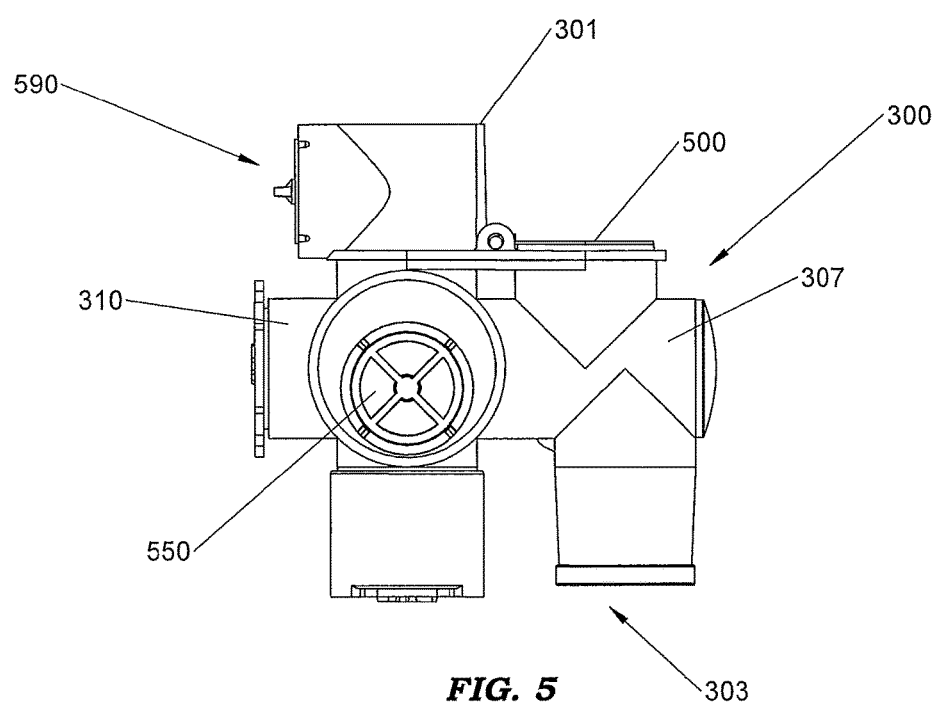
FIG. 5 is a rear elevation view of the patient interphase valve assembly of FIG. 4.
Figure 6:
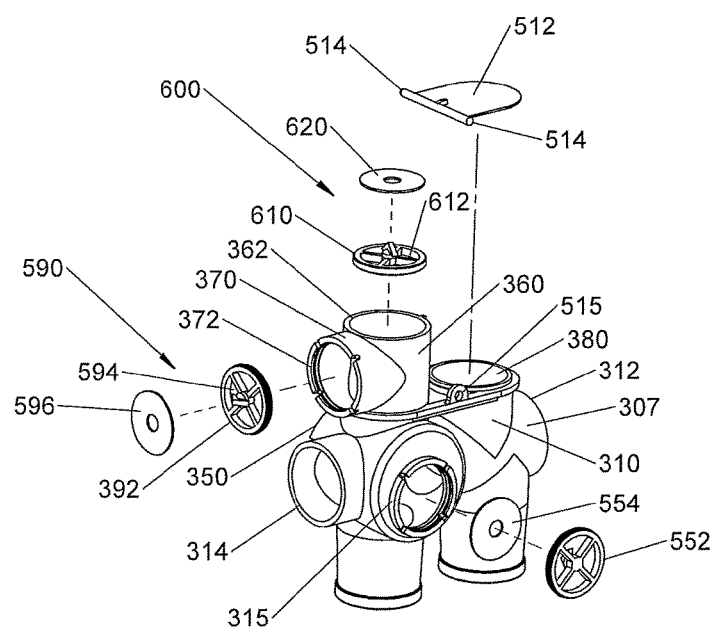
FIG. 6 is a partially exploded view of the patient interphase valve assembly.
Figure 7:
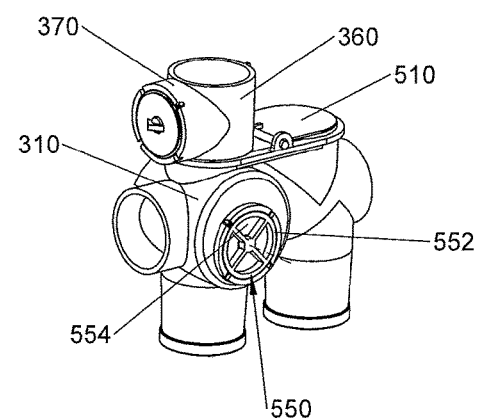
FIG. 7 is a perspective view of the patient interphase valve assembly of FIG. 6 in an assembled state.

As shown in FIG. 3, a hollow interior of the face mask body 210 has a landing or planar floor 213 that is part of the nose portion 216.

The face mask body 210 can be formed of any number of different materials including but not limited to polymeric materials.

The primary treatment module valve assembly (main module) 300 intimately mates with the face mask body 210 to form a complete assembly. In one embodiment, the main module 300 is integrally attached to the face mask body 210 so as to provide a single disposable structure. In other words, the main module 300 is not meant to be detached from the face mask body 210. However, the present invention is not limited to such a construction and covers, as well, an arrangement where the main module 300 is detachable.

Figure 10:
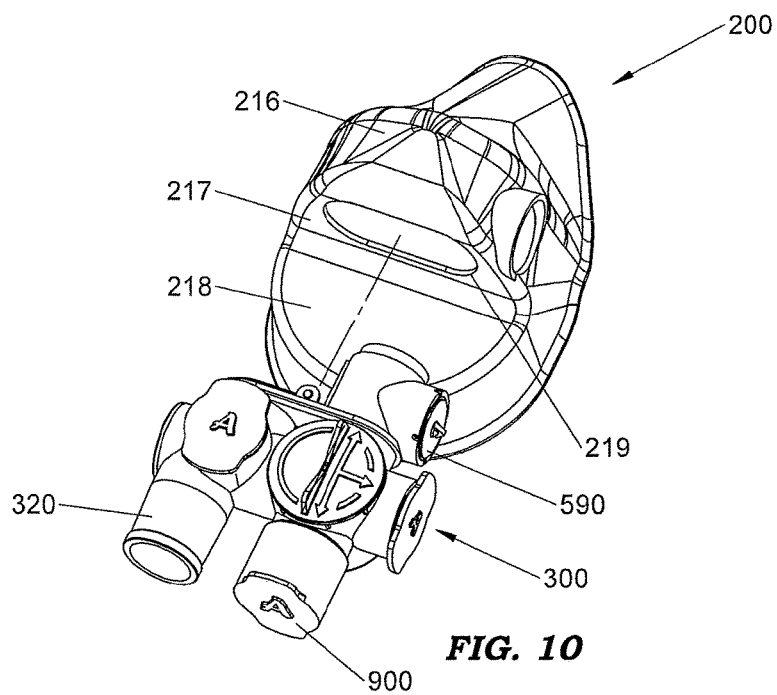
FIG. 10 is a front and bottom perspective view of the system of FIG. 1 prior to mating the primary treatment module valve assembly with the patient interphase system.
Figure 11:
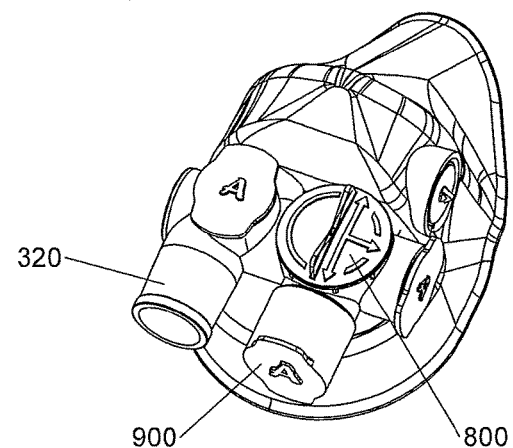
FIG. 11 is a front and bottom perspective view of the system of FIG. 10 in the assembled position.

In the illustrated embodiment as best shown in FIGS. 10 and 11, the module 300 can be received into an opening 219 formed in the planar underside wall 217 of the facemask 200. Any number of different types of coupling can be used between the module 300 and the face mask 200. In the illustrated embodiment, the module 300 can include a lip 309 that seats above the edge of the planar underside wall 217 that defines the opening 219. The lip 309 thus prevents the module 300 from moving downward within the opening 219.

The main module 300 includes a number of interconnected conduits that provide various flow paths for gas(es) as described herein. In particular, the main module 300 has a top 301, a bottom 303, a front 305, and a rear 307. The main module 300 also includes a main body 310 that is in the form of a hollow structure (e.g., tubular structure) that is open at a first end 312 and a second end 314. In the illustrated embodiment, the main body 310 is a hollow tubular structure that has a generally circular shape.

The main module 300 also includes a first conduit 320 that fluidly communicates with the hollow interior of the main body 310. The first conduit 320 is a hollow structure that represents a leg that extends downwardly from the main body 310 and is open at a bottom end 322 thereof. In the illustrated embodiment, the first conduit 320 is in the form of a hollow tubular structure, such as a hollow circular tube. Similarly, the main module 300 includes a second conduit 330 that fluidly communicates with the hollow interior of the main body 310. The second conduit 330 is similar or identical to the first conduit 330 in that it is hollow structure that represents a leg that extends downwardly from the main body 310 and is open at a bottom end 332 thereof. In the illustrated embodiment, the second conduit 330 is in the form of a hollow tubular structure, such as a hollow circular tube. The first conduit 320 is near the first end 312 of the main body 310, while the second conduit 330 is located near the second end 314 of the main body 310.

Along the front 305, there is a first port 340 that fluidly communicates with and forms an entrance into the hollow main body 310 above the first conduit 320 at the first end 312 of the main body 310. As shown, the first port 340 and the first conduit 320 are formed at a right angle relative to one another. Along the front 305, there is also a second port 350 that fluidly communicates with and forms an entrance into the hollow main body 310 above the second conduit 330. As shown, the second port 350 and the second conduit 330 are formed at a right angle relative to one another. The first port 340 has an open end 342 that faces forwardly and the second port 350 has an open end 352 that faces forwardly.

Along the rear 307, a safety port 315 is provided and defines an opening into the hollow interior of the main body 310. The safety port 315 is axially parallel with the second port 350 and is generally located across therefrom.

The main module 300 also includes a third conduit 360 that extends upwardly from the main body 310 and is in fluid communication with and forms an entrance into the hollow main body 310. Like the other conduits, the third conduit 360 can be in the form of a tubular structure that has an open free end 362. The third conduit 360 also includes a side port 370 that extends outwardly from a side of the third conduit 360. The side port 370 is open at a free end 372 thereof. The third conduit 360 and the side port 370 can be tubular structures.

The third conduit 360 is located generally above the second conduit 330 and communicates with the open interior of the hollow main body 310. At this end of the main body 310, there is an interior portion at which six (6) openings or ports intersect.

Along the top of the main body 310 there is also another port or opening 380 that opens into the hollow interior of the main body 310. The opening 380 provides one of the primary flow paths in addition to the third conduit 360 as described herein. The opening 380 is located next to the third conduit 360.

In accordance with the present invention, a number of accessories mate with the main body 310 to provide a modular and easily reconfigurable assembly. For example, a first closure 400 can be provided and disposed within the open first end 312 to close off and seal the first end 312 of the main body 310. The first closure 400 can be in the form of a plug or cap. A second closure 410 can be provided and disposed within the open second end 314 to close off and seal the second end 314 of the main body 310. The second closure 410 can be in the form of a plug or cap. The first and second closures 400, 410 have a lip or flange portion that allows the user to easily grasp and pull the closure out to remove it and open up the respective end of the main body 310 and also to insert the closure into the main body 310 so as to seal the main body 310. The first and second closures 400, 410 can be the same or different (as shown) structures.

In addition, a third closure 420 can be provided and disposed within the first port 340. As with the other closures 400, 410, the third closure 420 can be in the form of a plug or cap. The third closure 420 has a lip or flange portion that allows the user to easily grasp and pull the closure 420 out of the main body 310 and conversely, insert the closure 420 into the first port 340.

Within or on top of the opening 380, a first inhalation valve assembly 500 is provided, which can be in the form of a swing (pivot) or flapper or any other form of one-way valve mechanism. The first inhalation valve assembly 500 can be in the form of a one-way inhalation valve that opens' upon inhalation. More specifically, the first inhalation valve assembly 500 includes an inhalation valve member 510, which opens when the patient inhales. In the illustrated embodiment, the inhalation valve member 510 has a main body 512 and a coupling member 514 that serve to couple (in a pivotal manner) the main body 512 to a portion of the main body 310 of the device. The coupling member 514 can be in the form of an axle or a hinge pin or the like that has free ends that are received within a structure 515 that is part of the main body 310 and is in the form of a pair of mounts or brackets that include openings for receiving the free ends of the coupling member 514. The valve member 510 pivots open by rotating within the opposing mounts that form the structure 515.

The mating between the coupling member 514 and the structure 515 serves to securely hold the valve member 510 in place and permit it to open upon patient inhalation since as described herein, inhalation by the patient causes air flow in an upward direction through opening 380, thereby causing a lifting of the valve member 510 from the main body 310 (the valve seat defined therein).

Within the safety port 315, an emergency valve assembly 550 is provided and in the illustrated embodiment is in the form of an emergency air valve that opens when a patient needs additional air flow for breathing. The emergency air valve can be in the form of a flapper or swing (pivot) style valve or any other form of one-way valve mechanism. The emergency valve assembly 550 includes a valve seat 552 and a valve member 554 that mates with the valve seat 552. The valve assembly 550 is of a type commonly referred to as a one-way valve in that the valve opens in one direction to allow flow in only one direction. The valve member 554 can be a flapper type valve that mates with the valve seat 552 which can be in the form of a body (i.e., spoke structure) that receives the valve member 554 which covers the openings in the seat when closed and lifts from the seat 552 when opened. The emergency valve assembly 550 is thus located along the rear of the module and faces the wall 218 of the face mask 200. There is a space/gap between the module 300 and the wall 218 through which air flows and can enter the emergency valve assembly 550. Air entering through the valve assembly 500 is routed to the hollow interior of the main body 310 where it flows accordingly as described herein.

The system 100 also includes an exhalation valve assembly 590 that is designed to exhaust (vent) gas from the patient to the exterior (atmosphere). The exhalation valve assembly 590 is a one way valve assembly that is designed to only open during exhalation and only allows flow of gas in one way, namely, out of the system 100 and into the atmosphere. The exhalation valve assembly 590 is disposed within the side port 370 and in particular, at the free end 372 thereof. The exhalation valve assembly 590 can be any number of different types of one way valve assemblies including the one illustrated herein. The exhalation valve assembly 590 can be in the form of a valve seat 592 that supports a valve member 596. The valve seat 592 includes a plurality of openings 594 formed therein to allow gas to flow therethrough. In the illustrated embodiment, the valve seat 592 is a spoked structure and has a central mounting structure that is received through a center opening of the valve member 596 to attach the valve member 596 to the valve seat 592.

The exhalation valve assembly 590 is thus located above the main body 310 and gas reaches the exhalation valve assembly 590 by flowing through the third conduit 360 (which is open to the interior of the mask body 210 as described herein) and then the side port 370.

The system 100 also includes a supplemental gas valve assembly 600 that serves to allow a flow of supplemental gas to the patient. The valve assembly 600 is disposed at or near the interface between the main conduit body 310 and the conduit 360 and below the exhalation valve assembly 590. The supplemental gas valve assembly 600 is thus located at the entrance to the third conduit 360 from the main body 310 and thus, the supplemental gas valve assembly 600 allows gas flow between the main body 310 and the third conduit 360 when it is open and conversely, when the valve assembly 600 is closed, gas flow is prevented between these two conduit structures.

The supplemental gas valve assembly 600 is a one way valve assembly that is designed to only open during inhalation and only allows flow of gas in one way, namely, from the main conduit body 310 and into the third conduit 360. The supplemental gas valve assembly 600 can be any number of different types of one way valve assemblies including the one illustrated herein. The supplemental gas valve assembly 600 can be in the form of a valve seat 610 that supports a valve member 620. The valve seat 610 includes a plurality of openings 612 formed therein to allow gas to flow therethrough. In the illustrated embodiment, the valve seat 610 is a spoked structure and has a central mounting structure that is received through a center opening of the valve member 620 to attach the valve member 620 to the valve seat 610.

The third conduit 360 not only receives the supplemental gas valve assembly 600 but it can also include HME (heat and moisture exchange) media 700. As is known, HME media is constructed to heat and humidify inhaled gas and in the present system 100, the HME media 700 is disposed within the third conduit 360 above the supplemental gas valve assembly 600. The HME media 700 is thus in fluid communication with both the gas that flows through the main body 310 and into the third conduit 360 for inhalation by the patient and also exhaled gas that flows from the patient to the side port 370 where it flows out of the exhalation valve assembly 590. Thus, inhaled air flowing through the third conduit 360 to the patient and exhaled gas from the patient both are required to flow through the HME media 700. In this manner, the naturally warm and moist exhaled gas serves to treat the HME media 700 by adding heat and moisture thereto which is then transferred to the inhaled gas that flows through the HME media 700, thereby resulting in the inhaled gas being heated and humidified.

The shape and size of the HME media 700 are thus selected in part by the shape and size of the third conduit 360. In the illustrated embodiment, the HME media 700 is in the form of a cylindrical shaped body that snugly (sealingly) fits within the hollow tubular structure of the third conduit 360. The HME media 700 can be inserted and removed from the open top end 362 of the conduit 360. It is understood that the HME media can be designed alternatively in a non-cylindrical shape to conform to the shape of conduit 360 which could also be shaped non-cylindrical.

It will be appreciated that the HME media 700 is positioned such that it does not interfere with the normal operating movement of the supplemental gas valve assembly 600. In other words, the supplemental gas valve assembly 600 can freely open and close without interfering with the HME media 700.

In accordance with the present invention, the present invention includes a directional valve 800 that allows the gas flow paths within the system 100 to be defined and varied. The directional valve 800 thus opens up and closes off certain flow paths within the main body 310 and the related conduits and ports connected thereto so as to allow the user to define how the gas flows within the system 100. This allows the system 100 to have a significant number of different operating modes as described herein.

As shown, the illustrated directional valve 800 has a valve body 810 that includes a number of strategically placed openings. In particular, the valve body 810 is shaped and sized so that it is received into the second port 350 and can rotate therein to allow the position of the valve 800 to be varied. The valve body 810 can be a cylindrical shaped body as shown and includes a closed outer face 812 that is at a first end 813 of the body 810. The closed outer face 812 is exposed and accessible to the user and represents the portion of the valve body 810 that is manipulated by the user to change the position of the valve body 810 within the main body 310. The closed outer face 812 includes a protrusion or tab 816 that allows the user to manipulate the valve body 810 and more specifically, provides a contact surface from which the user can rotate the valve body 810.

An opposite second end 815 is an open end and in the case of a cylindrical valve body 810, the second end 815 is an open circular end.

The openings formed in the valve body 810 are spaced about the body at specific locations. In particular, a first side opening 820 is formed in the valve body 810 along the side wall of the valve body 810 that extends between the first end 813 and the second end 815. A second side opening 830 is formed in the valve body 810 along the side wall and at a location such that the axis of the opening 820 and the axis of the opening 830 are generally about 90 degrees disposed to one another. The valve body 810 also includes a third side opening 840 formed therein along the side wall and at a location such that the axis of the opening 840 and the axis of the first side opening 820 are about 180 degrees disposed to one another and the axis of the opening 840 and the axis of the third side opening 830 are about 90 degrees disposed to one another. In the illustrated embodiment, the first side opening 820 is located in the 12 o'clock position, the second side opening 830 is located in the 3 o'clock position and the third side opening 840 is located in the 6 o'clock position. When the valve body 810 is placed in this orientation, the 9 o'clock position does not include an opening and instead represents a closed end.

The closed outer face 812 includes indicia that indicate the direction of the openings 820, 830, 840. In particular, as illustrated, the closed outer face 812 includes arrows that point toward the open regions of the valve body, through which fluid (gas) can flow, in that the arrows point toward the three openings 820, 830, 840. The region of the valve body that does not include an opening does not include an arrow indicator since fluid (gas) cannot flow in this direction through the valve body 810. The indicia on the closed outer face 812 also include a solid semi-circular line that indicates that fluid cannot flow in this direction.

Figure 8:
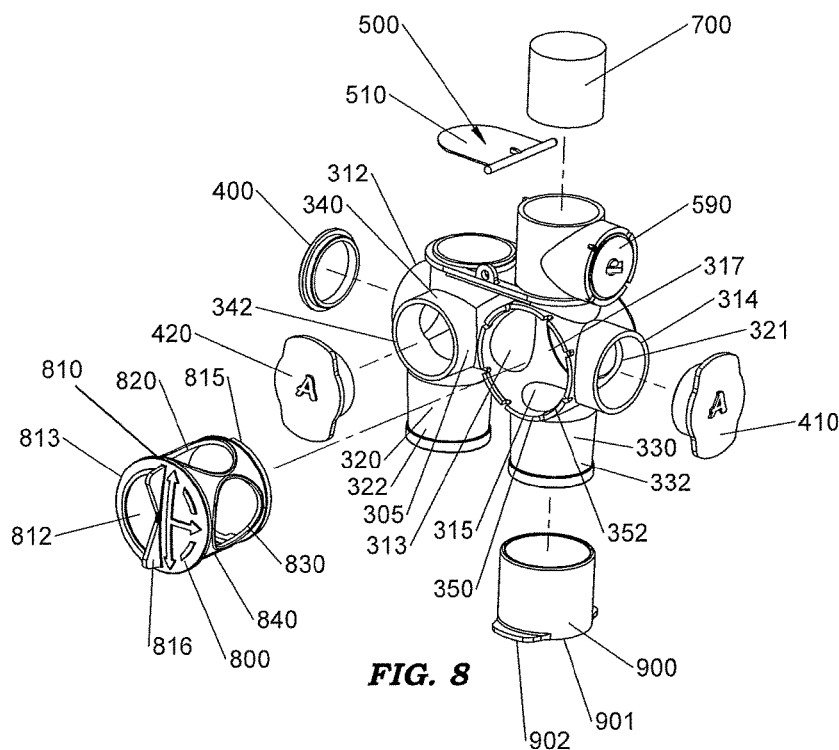
FIG. 8 is a partially exploded view of the patient interphase valve assembly illustrating a directional valve according to the present invention.
Figure 9:
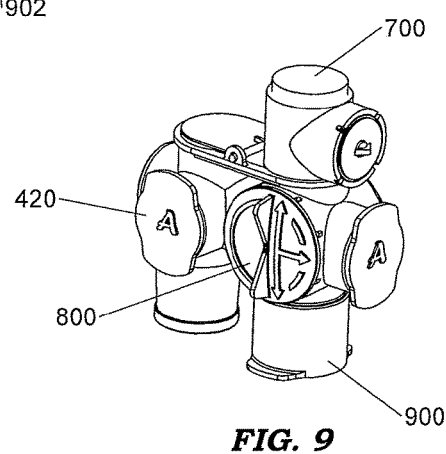
FIG. 9 is a perspective view of the patient interphase valve assembly of FIG. 8 in an assembled state.

When inserted into the second port 350, the valve body 810 extends into the hollow interior of the main body 310 and is adjacent the entrances to the other ports and conduits, such as the third conduit 360, the second conduit 330, and the safety port 315. The openings 820, 830, 840 are sized and shaped in view of the openings that are defined between the main body 310 and the various legs (conduits) that extend therefrom. As shown in FIG. 8, the main body 310 has a first internal opening 313, at the 9 o'clock position, that is within the main body 310 between the ports 320/340 on one side and 330/350 on the other; a second internal opening 319, at the 6 o'clock position, that is between the main body 310 and the leg port 330; a third internal opening 321, at the 3 o'clock position that is between the main body 310 and leg port 314; a fourth internal opening 323, at the 12 o'clock position that is between the main body 310 and leg port, 360; and a fifth internal opening 317 that is between the main body 310 and the rear conduit in which the safety (emergency) port 315 is located. It will therefore be appreciated that the location in which the directional valve 800 is disposed is defined by the intersection of five openings or conduits which define fluid flow paths. In particular, as shown in FIG. 8, a first flow path is in the direction of end 312; a second flow path is in the direction of end 314; a third flow path is in the direction of conduit 360; a fourth flow path is in the direction of the safety port 315; and a fifth flow path is in the direction of conduit 330.

When the directional valve body 810 is rotated within the main body 310, the openings 820, 830, 840 are placed in registration with the various internal openings, with the degree of registration being variable depending upon the positioning between the openings 820, 830, 840 and the internal openings defining the conduits.

It will therefore be understood that the directional valve body 810 is constructed to allow simultaneous flow along three flow paths that can be along three directions.

The system 100 also includes other accessories that mate with various openings/conduits thereof. In particular, a port cap 900 can be provided for mating with the open end 332 of the conduit 330. The port cap 900 has a closed end 901 that effectively seals off the conduit 330 so as to prevent fluid flow from the conduit 330. The port cap 900 has a tab 902 that assists the user in removing the port cap 900. The port cap 900 is thus used when use of the conduit 330 is neither desired nor necessary and the cap 900 thus effectively dead ends the conduit 330.

FIGS. 12-24 show different operating modes for the system 100 of the present invention.

Figures 12, 13:
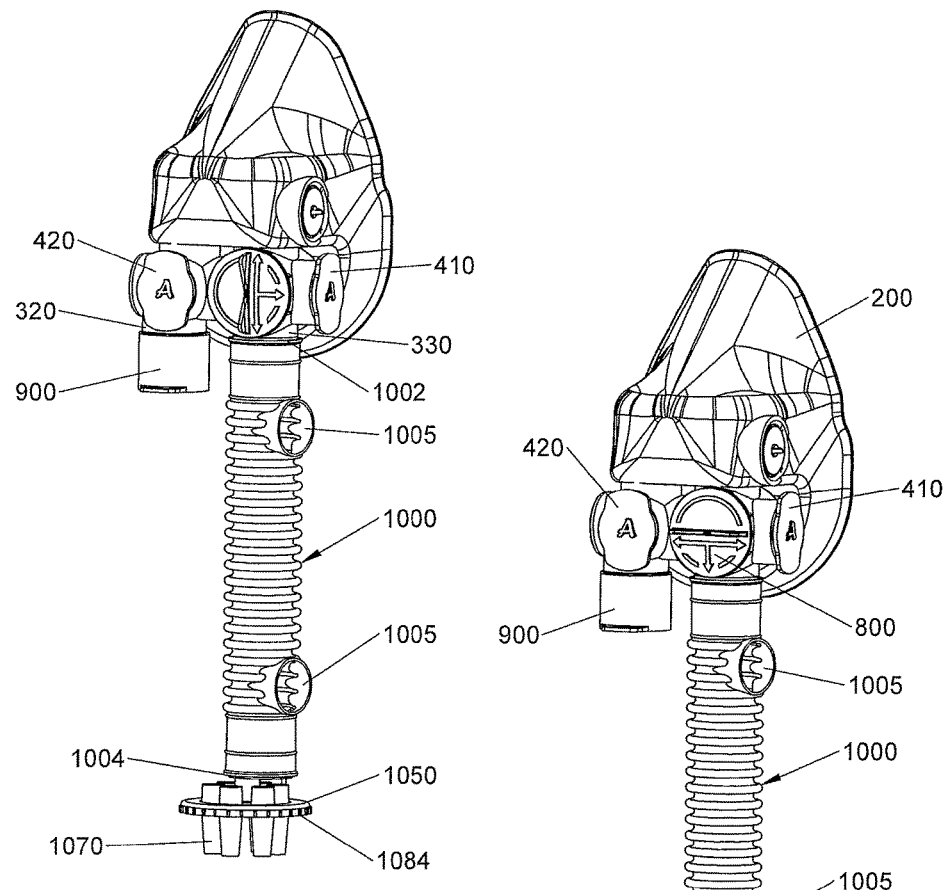
FIG. 12 is a front perspective view of the patient interface system of FIG. 1 attached to an expandable conduit for delivering gas in accordance with a first operating mode.
FIG. 13 is a front perspective view of the patient interface system of FIG. 12 shown in accordance with a second operating mode.

FIG. 12 shows a venturi style, low concentration oxygen delivery with humidification. In this operating mode, an expandable external conduit 1000 fluidly mates with the module 300 as described below. The expandable external conduit 1000 has a first end 1002 and an opposing second end 1004. The expandable external conduit 1000 is expandable along its length (i.e., it can be elongated and subsequently contracted). In the illustrated embodiment, the conduit 1000 is in the form of a collapsible corrugated tube. The conduit 1000 includes one or more air entrainment ports 1005 that are located along the length of the conduit 1000. An air entrainment port 1005 is an opening or hole formed along the conduit 1000 that freely allows air to flow into the hollow interior of the conduit 1000. The air entrainment port 1005 is a complete hole formed in the side wall of the conduit 1000 to allow free flow of air into the conduit 1000. The air entrainment port 1005 can be located at any location along the conduit 1000 and there can be 1 or more ports 1005 formed in the conduit 1000.

The first end 1002 of the conduit 1000 sealingly mates with the open end 332 of conduit 330 so as to allow the gas (such as air) flowing through the conduit to enter into the conduit 330. Any number of different types of fits or couplings between the two parts can be achieved; including but not limited to a mechanical fit, such as a frictional fit, snap-fit, etc.

Figure 25A:
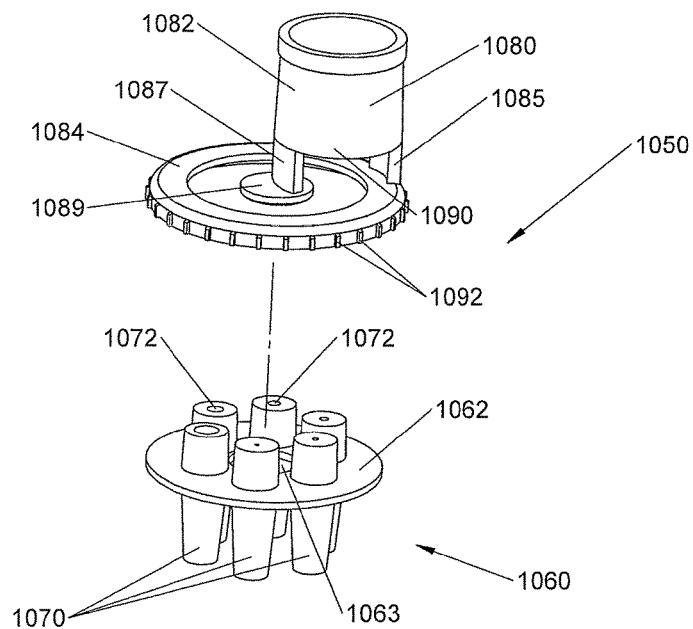
FIG. 25A is an exploded perspective view of a multi-port, variable concentration, gas delivery venturi connector.
Figure 25B:
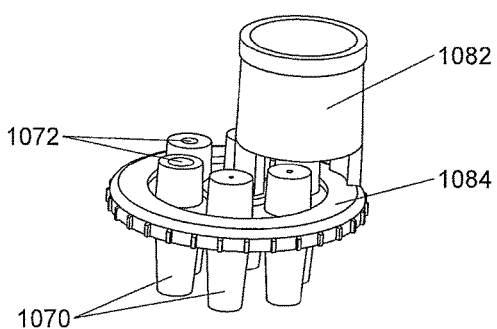
FIG. 25B is a perspective view of the multi-port, variable concentration, gas delivery venturi connector in an assembled position.
Figure 26:
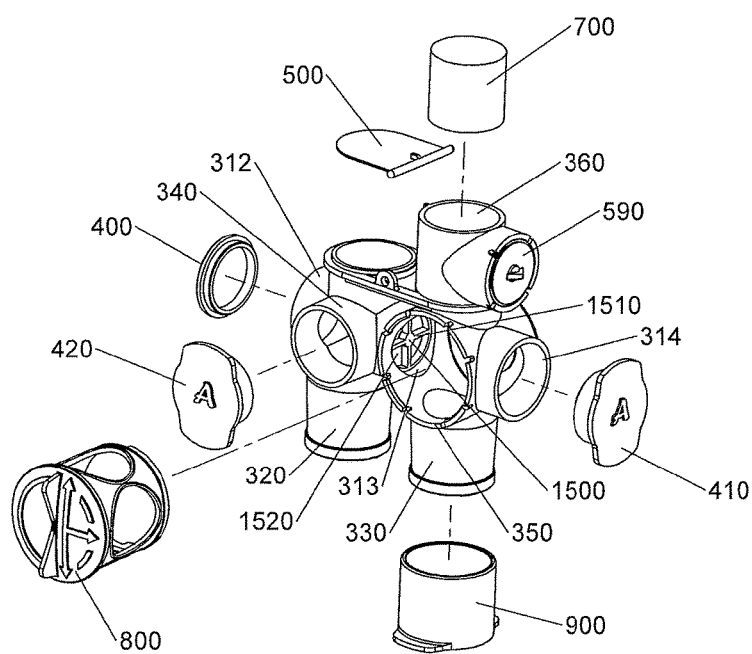
FIG. 26 is an exploded perspective view of a patient interface system/modular pulmonary treatment system according to another embodiment and configured for delivery of gases to a patient including aerosolized medication.
Figure 27:
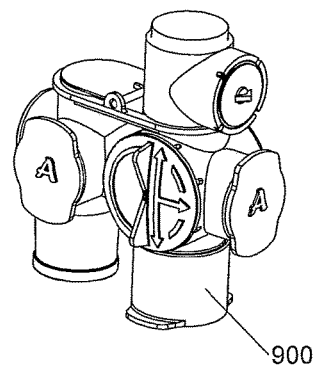
FIG. 27 is a perspective view of the system of FIG. 26 in an assembled state.
Figures 32, 33A:
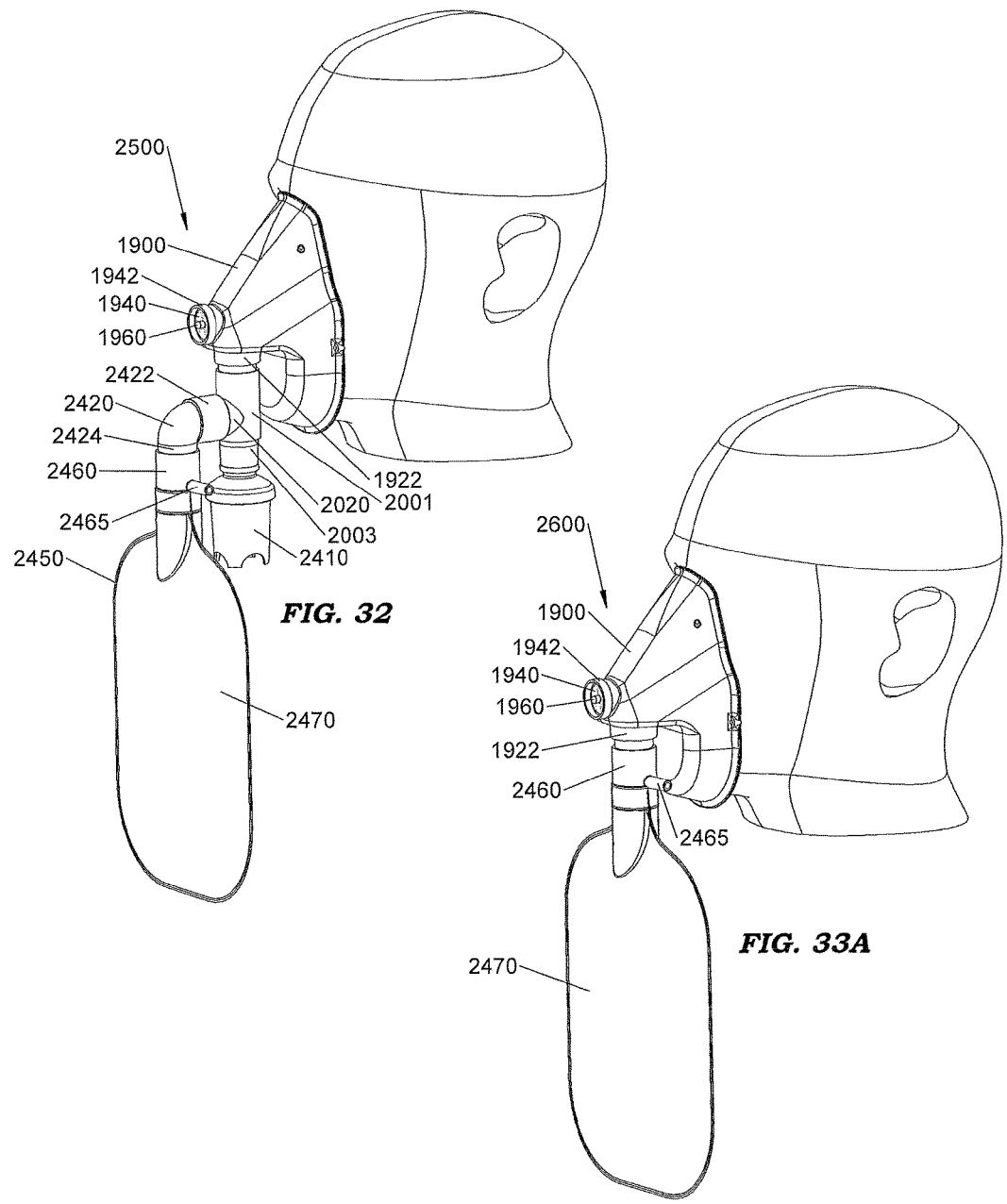
FIG. 32 is a side perspective view of a patient interface system according to another embodiment for high dose aerosol drug delivery.
FIG. 33A is a side perspective view of a patient interface system according to another embodiment for 100% non-rebreather gas (oxygen) delivery.

A multi-port low concentration venturi 1050 is also provided for mating with the second end 1004 of the conduit 1000. FIGS. 25A-B illustrate the venturi 1050 in greater detail. The venturi 1050 can include a first connector 1060 that includes a plurality of venturi tubes 1070 that are attached to and pass through a first connector body 1062 which can be in the form of a plate or disk that has a center hole 1063 formed therein. The venturi tubes 1070 are elongated tubular structures having a center bore and distal orifice 1072 formed therein. As shown, the tubes 1070 can have different diameter orifices 1072. It will be understood that the flow rate through the tubes 1070 differs depending upon the diameter of the orifice 1072 and therefore, the tubes with smaller diameter orifices have lower flow rates than the tubes with larger diameter orifices.

The venturi 1050 also includes a second connector 1080 that mates with the first connector 1060. The second connector 1080 includes a first part that is in the part of a tubular structure 1082 that is open at both ends and includes a second part in the form of an annular shaped base ring 1084 that has a center opening. The first part 1082 is connected to the ring 1084 by means of a first leg 1085 that is attached to a peripheral edge of the ring 1084. A second leg 1087 also extends downwardly from the tubular structure 1082. The second leg 1087 terminates in a small disk 1089 that is disposed within the center of the opening that is defined within the center of the ring 1084. The disk 1089 and annular base ring 1084 thus define an annular shaped opening or track 1090.

An outer peripheral side edge of the ring 1084 includes ribs 1092 to assist in positioning the axes of the venturi tubes 1070 to the axis of the tubular structure 1082.

It will be appreciated from FIGS. 25A-B that a portion of the annular shaped opening/track 1090 extends underneath the hollow tubular structure 1082 and thus the hollow interior (bore) of the structure 1082 intersects the arcuate shaped portion of the opening 1090.

The first and second connectors 1060, 1080 mate together by inserting the small disk 1089 into the hole 1063 of the connector body 1062, thereby allowing the first connector 1060 to rotate within the annular shaped opening or track 1090. As shown, the tubular structure 1082 is constructed such that only one of the venturi tubes 1070 and in particular the center bore 1072 thereof is centrally located within the bore of the tubular structure 1082.

In accordance with the present invention, the first connector 1060 can rotate relative to the second connector 1080 and within the annular shaped opening/track 1090 to vary which venturi tube 1070 is centrally located within the bore of the tubular structure 1082. Thus, the user can vary the flow rate of the fluid being discharged from the venturi tube 1070 into the bore of the tubular structure 1082 by selecting the desired venturi tube 1070 which is centrally located within the tubular structure 1082. To change the characteristics of the fluid flowing into the bore of the tubular structure 1082 and thus into the conduit 1000, the user simply rotates the first connector 1060 within the track 1090 such that the venturi tubes 1070 rotate about the disk 1089 until the desired venturi tube 1070 is properly located underneath the bore of the tubular structure 1082.

The present invention thus allows the user to easily alter how the venturi functions and how the gas is delivered to the patient.

FIG. 12 shows an operating mode in which humidification is provided to the gas (e.g., oxygen) being injected into the module 300. In particular, the directional valve 800 is positioned such that the openings 820, 830, 840 are in registration with the internal opening 319 and the openings leading to the conduit 360 and the conduit portion to the end 314. In other words, the direction valve 800 is positioned such that the conduit 330, the conduit 360 and the main body 310 toward the end 314 are open and fluid can flow therein. However, the second end 314 is closed off with the cap 410 and thus gas cannot exit or flow into the second end 314. In addition, the internal opening 313 is closed and thus gas cannot flow toward the first end 312 within the main body 310.

In this position of the directional valve 800, fluid can only flow through the conduit 330 into the main body 310 and into the conduit 360 and thus, when the patient inhales and the supplemental gas valve assembly 600 opens (under the patient inhalation), gas flowing through the conduit 1000 flows into the conduit 330 and through the open valve assembly 600 into contact with the HME media 700 which acts to heat and humidify the inhaled gas.

When the patient exhales, the exhaled gas flows through conduit 360 and the HME media 700 located within the conduit 360 thereby capturing the heat and moisture from the patients exhaled gas and is vented through the valve assembly 590. Note that during exhalation, swing valve 500 is closed, valve 620 is also closed, both the first conduit 320 and the first end 312 are capped, and hence exhaled air can only exit via HME 700 and then through the exhaled valve 590.

FIG. 12 thus shows a venturi style, low concentration oxygen delivery (by means of the conduit 1000) with humidification.

FIG. 13 illustrates an operating mode that is similar to the operating mode that shown in FIG. 12 with the exception that the gas (oxygen) is delivered to the patient without humidification. The directional valve 800 is rotated in the operating mode such that the conduit 360 is closed off and thus gas does not flow into the conduit 360 and thus does not flow into contact with the HME media 700. Instead, the gas flowing through the conduit 1000 enters the conduit 330 and can flow in the main body 310 towards both the first end 312 and the second end 314. Since the second end 314 is closed off with the cap 410 and other conduits are closed off as shown, the gas entering the main body 310 through the conduit 1000 flows toward the first end 312. Upon patient inhalation, the main inhalation valve assembly 500 opens and thus the gas flowing within the main body 310 enters the interior of the patient interface 200 by flowing through the valve assembly 500 and thereby reaches the patient.

When the patient exhales, the exhaled gas can only flow through the HME media 700 within conduit 360 and exits through the side port 370 through the exhalation valve assembly 590 to atmosphere.

Figure 14:
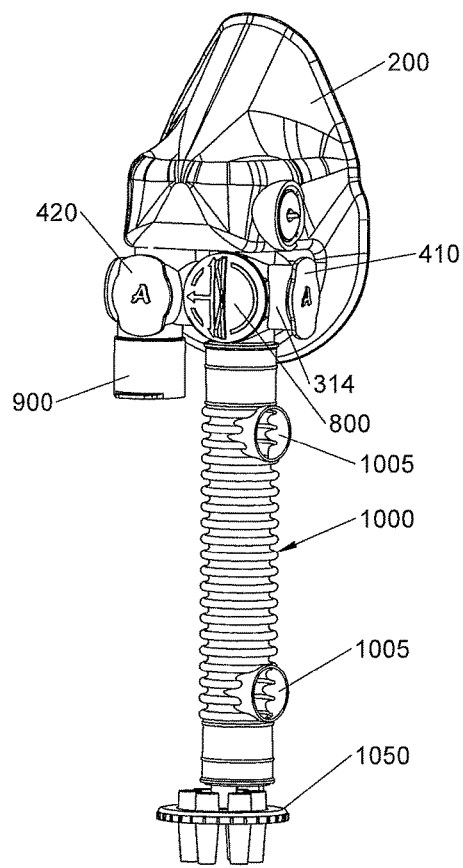
FIG. 14 is a front perspective view of the patient interface system of FIG. 12 shown in accordance with a third operating mode.

FIG. 14 illustrates a different operating mode and in particular, shows a venturi style, low concentration oxygen delivery with reduced humidification/resistance. In this operating mode, the directional valve 800 is positioned such that the conduit 330, the conduit 360 and the internal opening 313 are open to flow, while the main body 310 toward the second end 314 is closed off (as shown by the indicator arrows). The conduit 320 is closed off with the cap 900.

It will be appreciated that in this embodiment, the gas (e.g., oxygen) flowing through the conduit 1000 enters the main body 310 and flows both (1) into the conduit 360 and (2) flows through the internal opening 313 toward the first end 312. Upon patient inhalation, the main inhalation valve assembly 500 opens and gas flows into the face mask 200 to the patient and also flows through the open supplemental gas valve assembly 600 (inhalation valve 620) and through the HME media 700 to the patient. Thus, gas flows along two flow paths to the patient during inhalation, with one path being a path that humidifies the gas. It will also be appreciated that in all of the operating modes, the amount of gas flowing into a conduit through the directional valve can be varied by rotating the directional valve to cause less registration between the openings 820, 830, 840 and the respective conduits. This arrangement though allows intermediate level of heated and moist gas to be inhaled, it has the advantage of overall reduced resistance during inhalation.

Figure 15:
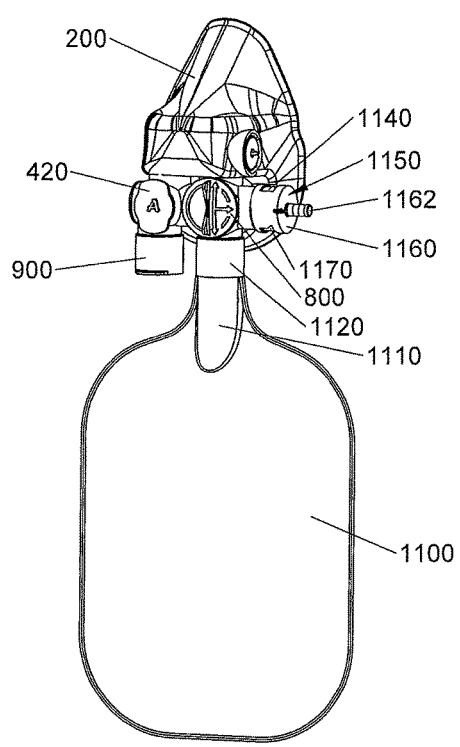
FIG. 15 is a front perspective view of the patient interface system of FIG. 1 attached to a gas reservoir assembly and venturi mechanism for delivering gas in accordance with a first operating mode.

FIG. 15 shows another operating mode in which an accessory module in the form of a gas reservoir assembly 1100 and the venturi mechanism via venturi connector 1150 are used to deliver variable concentration of oxygen. The gas reservoir assembly 1100 is in the form an expandable bag that includes a neck portion 1110. The neck portion 1110 includes a connector 1120 that allows the bag 1100 to be sealingly attached to the module 300. The connector 1120 attaches to the conduit 330 to permit the conduit 330 to be in free communication with the interior of the bag 1100. The cap 900 is placed on the conduit 320 to close off this conduit 320.

The second end 314 of the main body 310 is an active port in this embodiment and a venturi connector 1150 mates with the second end 314 to allow gas to be delivered thereto. The venturi connector 1150 includes an outer part 1160 that includes a tubing connector (nipple) 1162 that protrudes outwardly therefrom and provides an entrance into the hollow interior of the connector 1150. The outer part 1160 also includes one or more and preferably a plurality of openings or windows 1170 that are located circumferentially about the side wall of the outer part 1160. The venturi connector 1150 also includes an inner part that is a tubular structure and likewise includes one or more openings or windows that are located circumferentially about the side wall of the inner part 1140. Registration between the windows 1170 of the outer part 1160 and the openings of the inner part 1140 can be achieved by moving the outer part 1160 relative to the inner part 1140 or vice versa. It will be appreciated that air enters through the overlying window 1170 and the inner opening 1140 and into the interior of the tubular structure of the inner part that is in fluid communication with the hollow interior of the body part 310.

As gas, such as oxygen flows through the connector 1162 and into the hollow interior of the inner part, air is entrained into the flow stream through the openings of the inner part 1140 and the window 1170. The amount of air entrained can be varied by increasing or decreasing the relative size of the openings formed by the relationship of the outer part 1150 and the inner part 1140 by rotating the outer part windows with respect to the stationary inner part windows.

The cap 900 closes off the conduit 320 and the first end 312 is also closed off.

The directional valve 800 is positioned such that the conduits 330, 360 are open along with the second end 314 of the main body 310. Since the conduit 330 is open, the gas reservoir assembly (bag) 1100 is freely open to the main body 310 and gas can both flow into and flow out of the bag 1100 relative to the main body 310.

Gas, such as oxygen, flowing into the main body 310 can flow directly into the bag 1100 and thus, the bag 1100 serves a structure that stores excess gas (that enters through the venturi connector 1150) that is not immediately needed by the patient. However, since the inside of the bag 1100 is in communication with the conduit 360 when the supplemental gas valve assembly 600 opens, the gas within the bag 1100 can be inhaled by the patient during inhalation since the valve member 620 is an inhalation valve.

In this embodiment, all of the gas inhaled by the patient passes through valve assembly 600 and thus passes through the HME media 700 resulting in heat exchange and humidification thereof. The exhaled air exists through the HME media 700 and the exhalation valve assembly 590.

Figure 16:
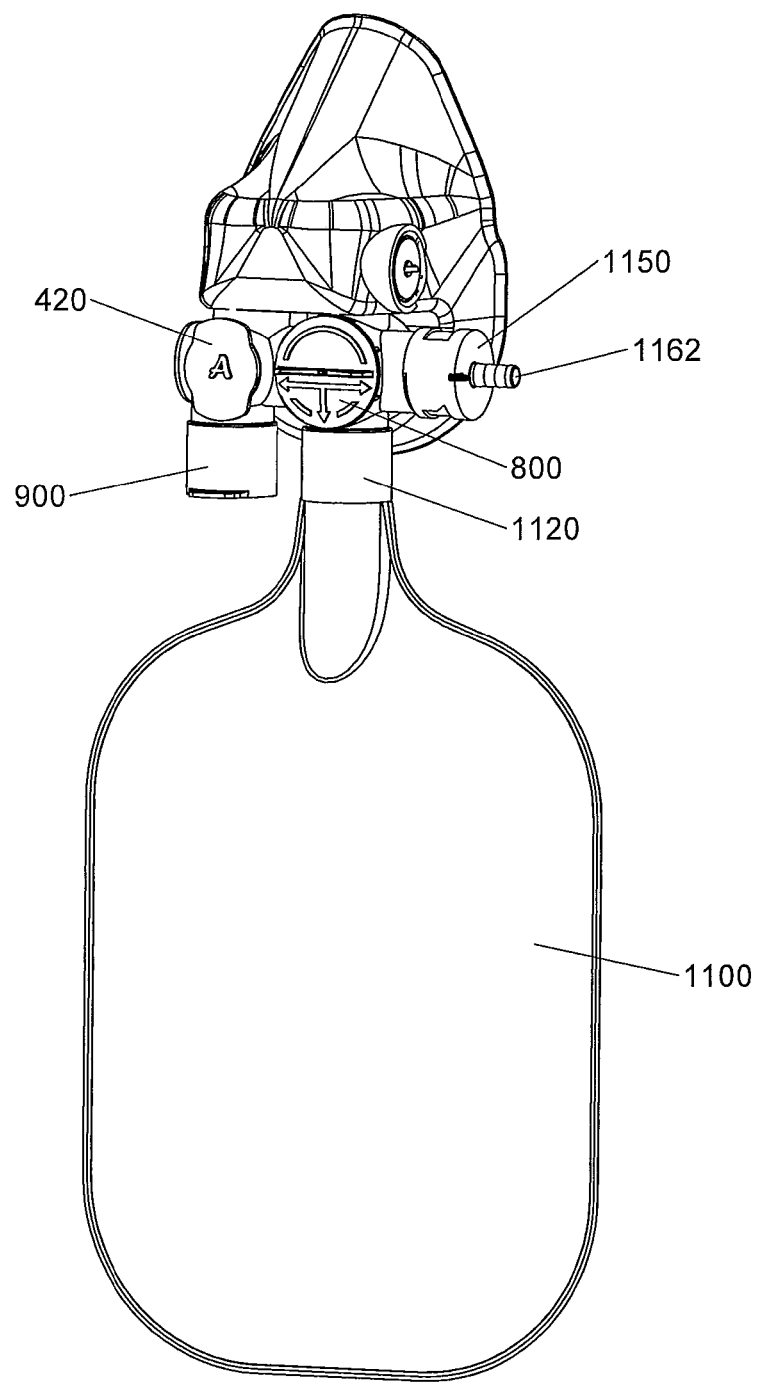
FIG. 16 is a front perspective view of the patient interface system of FIG. 15 shown in accordance with a second operating mode.

FIG. 16 shows an operating mode that is very similar to the operating mode shown in FIG. 15 with the exception that the inhaled air is provided without humidification. In this embodiment, the directional valve 800 is rotated such that the conduit 360 is closed off and instead, the internal opening 313 is open to allow gas that enters through the venturi connector 1150 at the second end 314 and additional gas, if needed, from the bag 1100 to flow toward the first end 312 which is closed off with a cap. As a result, when the patient inhales, the main inhalation valve 500 opens and the gas flows therethrough into the face mask 200. When the main inhalation valve 500 is closed as during exhalation, the gas flowing into the main body 310 from the venturi connector 1150 can flow into the bag 1100 for storage. As a result, the only inhalation flow path is through the main inhalation valve assembly 500 and thus, the inhaled air is not heated or humidified since no inhaled air flows through the HME media 700.

Figure 17:
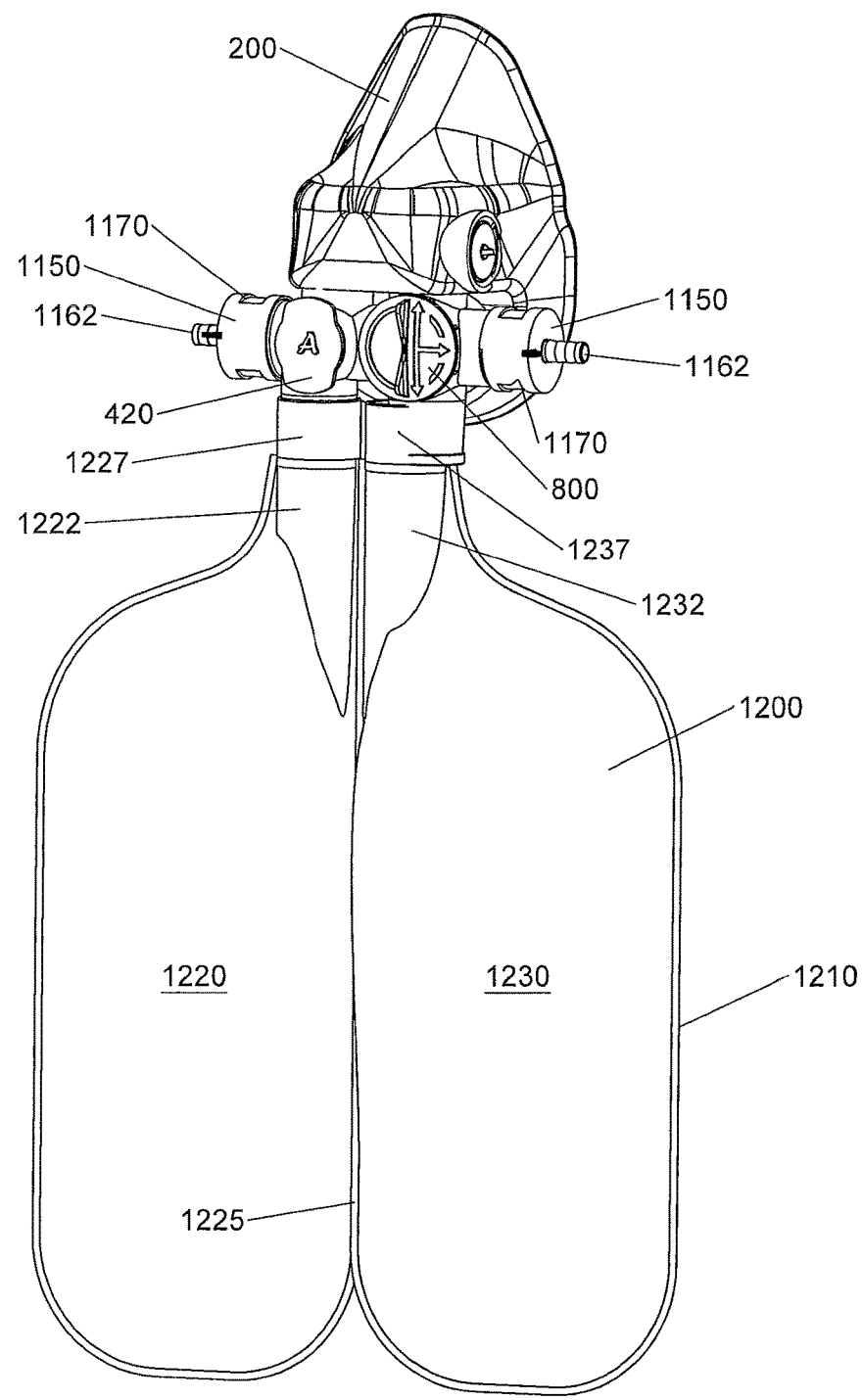
FIG. 17 is a front perspective view of the patient interface system of FIG. 1 attached to a dual gas reservoir assembly and two venturi mechanism shown in accordance with a first operating mode.

FIG. 17 shows another operating mode which is similar to the modes shown in FIGS. 15 and 16 except that in this embodiment, a dual gas reservoir assembly 1200 is provided. The operating mode shown in FIG. 17 is a variable concentration gas (oxygen) delivery with partial heat exchange and humidification. The dual gas reservoir assembly 1200 includes two different storage compartments that are located within the expandable bag structure. In particular, a body 1210 of the assembly 1200 is partitioned into a first compartment 1220 and a second compartment 1230 by an inner dividing wall 1225. Gas cannot pass through this wall 1225.

The body 1210 includes two neck portions, namely a first neck portion 1222 that is associated with the first compartment 1220 and a second neck portion 1232 that is associated with the second compartment 1230. The first neck portion 1222 includes a first neck connector 1227, while the second neck portion 1232 includes a second neck connector 1237. The first neck connector 1227 is sealingly attached to the conduit 320, while the second neck connector 1237 is sealingly attached to the conduit 330. Gas can thus flow from the main body 310 into and out of each of the first and second compartments 1220, 1230.

In this embodiment, there is a pair of venturi style variable concentration delivery means 1150, one at the open first end 312 and the other at the open second end 314. As described above, each of these venturi style variable concentration delivery means 1150 is constructed to let gas, such as oxygen from an oxygen source, to flow therethrough and the windows 1170 formed therein allow a user to select the amount of air that is also introduced into the venturi connector 1150 to mix with the gas being injected therethrough.

In FIG. 17, the directional valve 800 is positioned such that the conduit 360 is open and the conduit 330 is open and the end 314 is open. The internal opening 313 is closed and thus gas cannot flow toward the first end 312 into contact with the main valve assembly 500 from the second end 314 and from the second compartment 1230. As a result, the inhaled air is humidified since the gas introduced through the connector 1162 and mixed with air through window 1170 flows through the supplemental gas valve assembly 600 (upon patient inhalation) and through the HME media 700 where the inhaled gas is humidified before flowing into the face mask 200 to the patient.

Gas (oxygen) flowing through the connector 1162 at the first end 312 (along with air introduced through the window 1170) can flow into the first compartment 1220 and also upon inhalation by the patient, the gas flows through the main inhalation valve 500 into the interior of the face mask 200 to the patient.

It will be appreciated that the gas introduced at the first end 312 can be the same or a different gas than the gas introduced at the second end 314. When it is a different gas, the patient thus receives two different gases.

Figure 18:
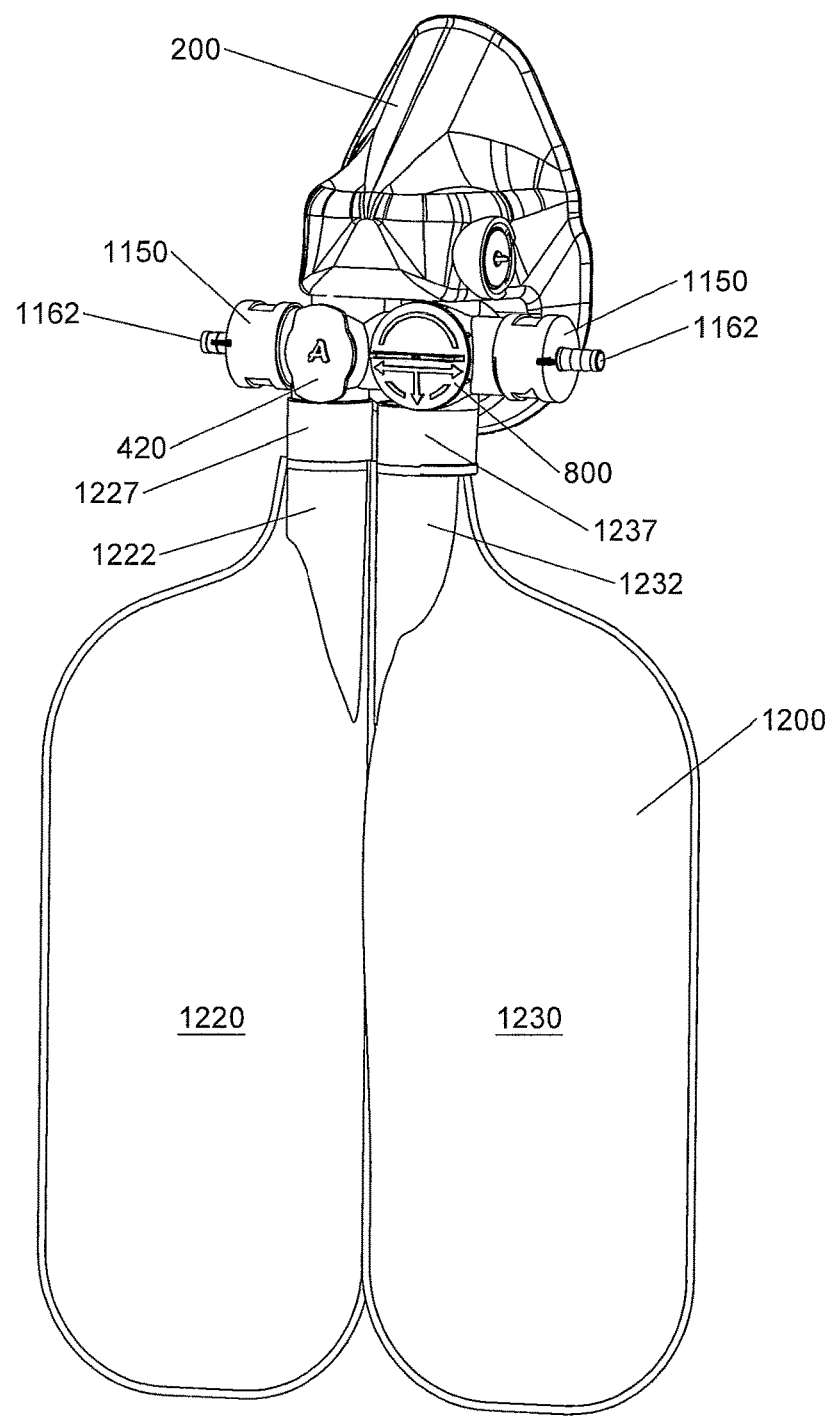
FIG. 18 is a front perspective view of patient interface system of FIG. 17 shown in accordance with a second operating mode.
Figure 21:
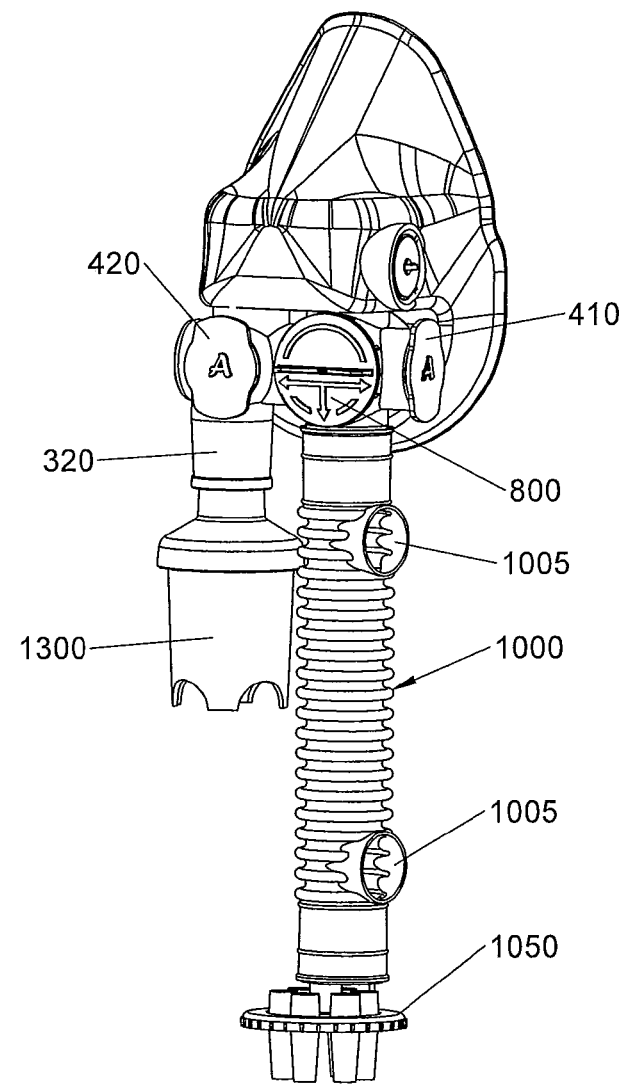
FIG. 21 is a front perspective view of the system of FIG. 20 in further combination with a multi-port low concentration venturi for aerosol drug and controlled low concentration gas delivery.
Figure 22:
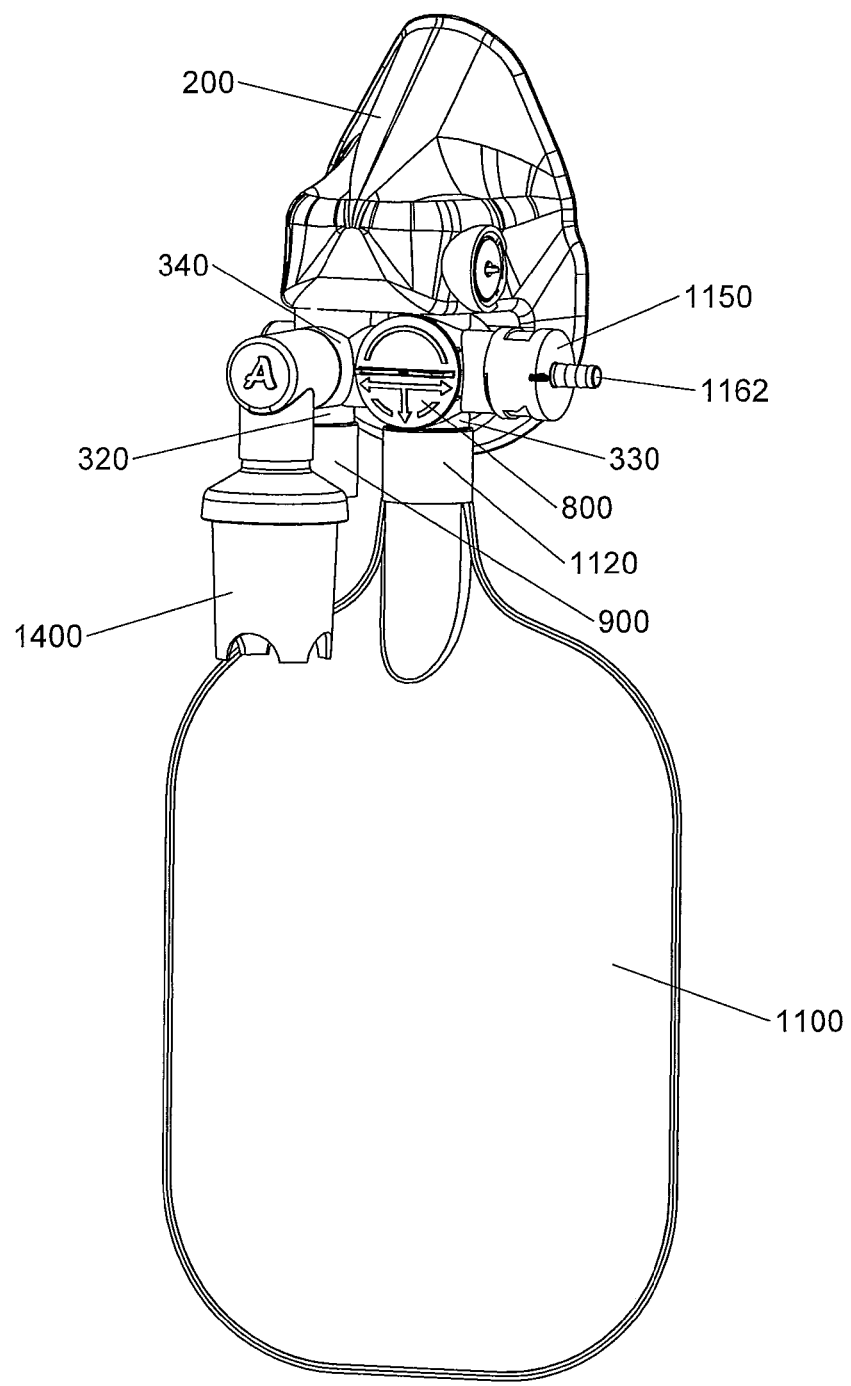
FIG. 22 is a front perspective view of the patient interface system of FIG. 1 in further combination with a nebulizer and a gas reservoir assembly for aerosol drug and controlled high concentration gas delivery.
Figure 23:
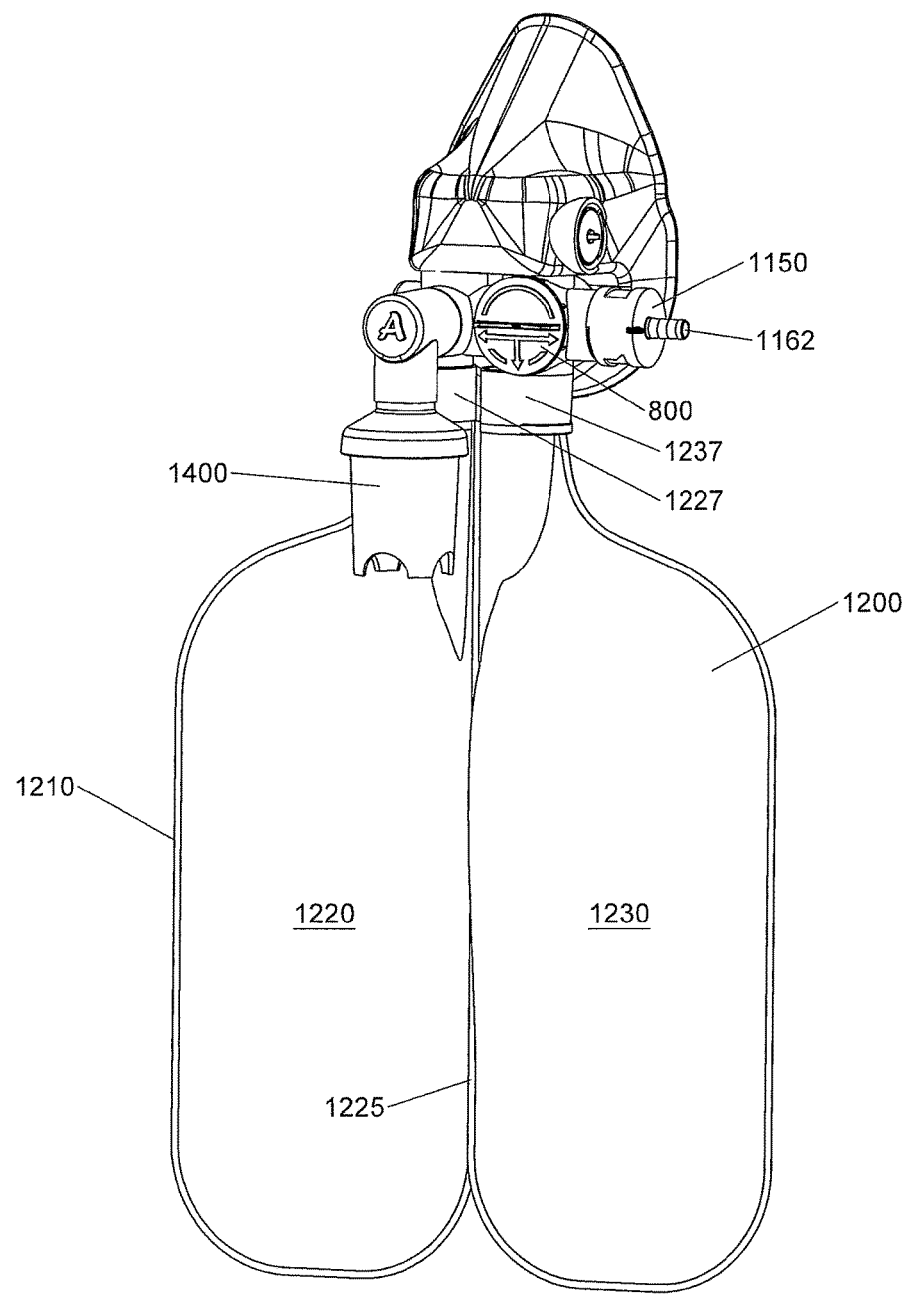
FIG. 23 is a front perspective view of the patient interface system of FIG. 1 in further combination with a nebulizer and a dual gas reservoir assembly shown in accordance with a second operating mode.
Figure 24:
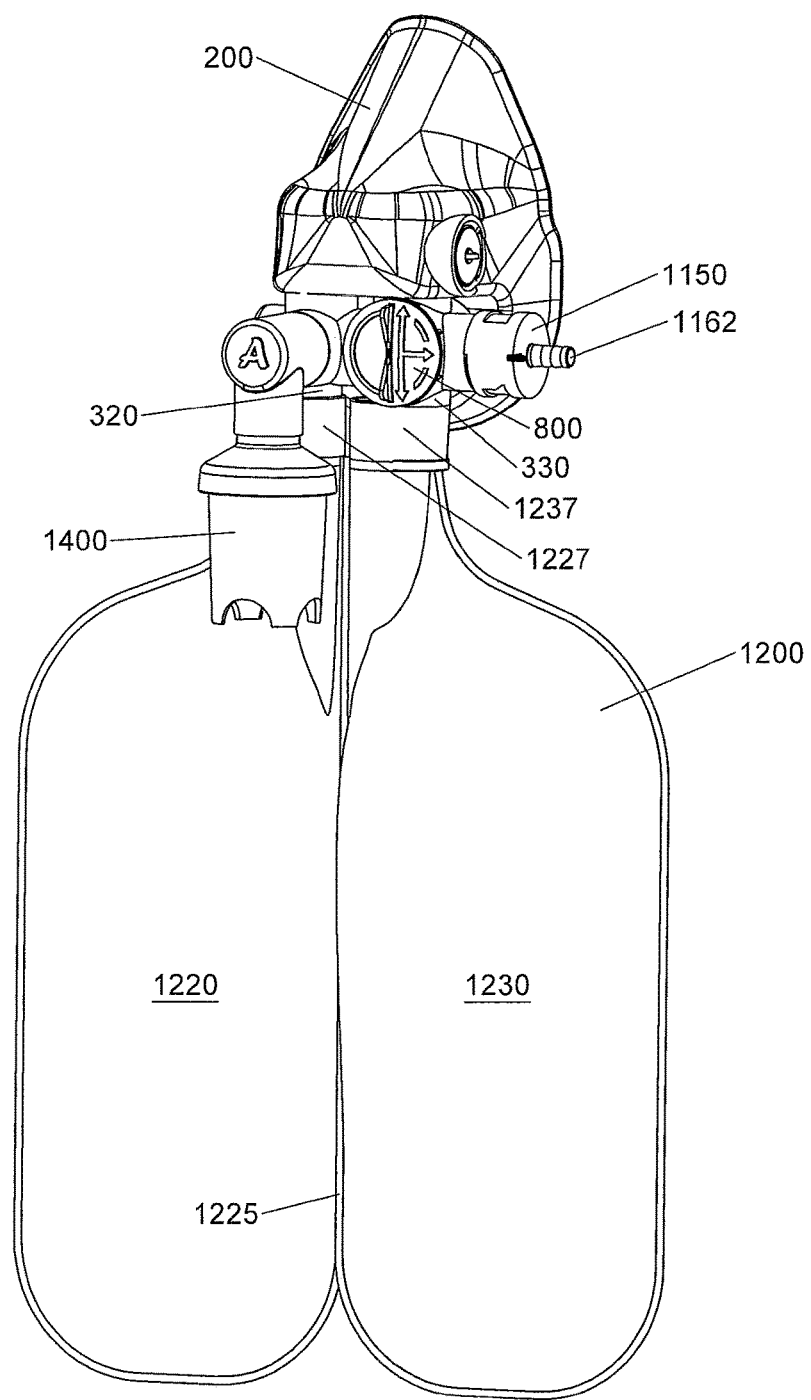
FIG. 24 is a front perspective view of the patient interface system of FIG. 23 shown in accordance with a third operating mode.

FIG. 18 shows another operating mode and in particular, it illustrates variable concentration gas (oxygen) delivery without humidification. The main difference between the modes shown in FIG. 17 and FIG. 18 is that the system of FIG. 17 humidifies the inhaled air, while FIG. 18 does not. As a result, the directional valve 800 is positioned such that the conduit 360 is closed off and the internal opening 313 is open as well as the second end 314 of the main body 310 and the conduit 330 is open.

In this position, the direction valve 800 allows gas that is injected into either the first end 312 and/or the second end 314 to flow to the main inhalation valve assembly 500 and upon inhalation, the gas flows into the face mask 200 as a result of the valve assembly 500 opening. Thus, gas can only flow into the face mask 200 by means of the opening of the inhalation valve assembly 500. However, gas that flows into the venturi connector 1150 at the first end 312 can flow both into the first compartment 1220 and the second compartment 1230 since the internal opening 313 is open. Similarly, gas that flows into the venturi connector 1150 at the second end 314 can flow into both the second compartment 1230 and the first compartment 1220. It will be appreciated that the two gases can thus mix to a degree and flow into the various compartments 1220, 1230. However, based on fluid dynamics and flow paths based on the path of least resistance, more of the gas that enters into the first end 312 flows into the first compartment 1220 and similarly, more of the gas that enters into the second end 314 flows into the second compartment. In any event, both gases must flow through the main valve assembly 500 in order to reach the patient.

FIG. 19 shows the system 100 in a standard aerosol drug delivery mode. In this operating mode, the conduits 320, 330 are open and conduit 360 is closed. Both ends 312, 314 of the main body 310 are closed off with plugs and/or caps 400, 410 and therefore gas only flows into the mask through the conduits 320, 330. In this case, a nebulizer 1300 is provided and a neck portion 1310 of the nebulizer 1300 mates with the conduit/port 320 to sealingly attach the nebulizer 1300 to the module 300.

In this operating mode, the conduit 330 is open and thus acts as a supplemental gas source as described below. The directional valve 800 is positioned such that the conduit 360 is closed off and thus inhaled air does not pass through the HME media 700. The aerosolized drug is discharged from the nebulizer 1300 and enters the conduit 320 and flows into the main body 310 in which is it available for delivery to the patient upon inhalation and upon opening of the main inhalation valve assembly 500. It will be appreciated that excess aerosolized drug can flow through the main body 310 and be vented through the conduit 330 to atmosphere. This is especially the case when the patient is exhaling and the main inhalation valve assembly 500 is closed and thus the aerosolized drug cannot flow to the patient. Conduit 330 also provides a supplemental gas source in addition to the gas being injected into the module 300 by the nebulizer 1300 to meet the inhalation requirements of the patient.

FIG. 20 shows an operating mode for enhanced aerosol drug delivery. In this operating mode, the only difference compared to the arrangement of FIG. 19 is the inclusion of the conduit 1000 which is attached to the conduit/port 330.

The conduit 1000 is sealingly attached to the conduit/port 330 and is open at the other end to allow venting of gas through the conduit/port 330. The conduit 1000 serves as at least a partial reservoir for storing aerosolized drug when the patient exhales. In other words, when the patient exhales, gas can flow from the main body 310 into the conduit 1000 where some remains captured therein and when the patient subsequently inhales, the main inhalation valve assembly 500 opens and aerosol drug in the conduit 1000 can flow to the face mask 200 and the patient. The conduit 1000 is adjustable-collapsible and expandable to adjust the length of the reservoir for medication storage during exhalation and thereby enhancing controlled and predictable medication delivery during inhalation When the user desires to operate the system in this mode, the conduit 1000 can be selected so as to have no or only a few air entrainment ports 1005.

FIG. 21 shows another operating mode that is similar to the one shown in FIG. 20 with the exception that the system in FIG. 21 also includes the multi-port low concentration venturi device 1050. This operating mode is standard aerosol drug and low concentration oxygen delivery. The venturi device 1050 mates with the free end of the conduit 1000 and allows delivery of a gas (e.g., oxygen). This arrangement allows to control the desired oxygen concentration while simultaneously administering medication.

Since the venturi device 1050 mates with conduit 1000, the gas flowing therethrough flows into the conduit 1000 to the patient via the main body 310.

FIG. 22 shows another operating mode that is defined as standard aerosol drug and variable concentration oxygen delivery. In this operating mode, the gas reservoir assembly 1100 is sealingly attached to the conduit/port 330. The conduit/port 320 is closed off by the cap 900. A nebulizer 1400 is sealingly attached to the nebulizer port 340 for delivery of aerosol drug to the patient by flowing through the main body 310. Upon inhalation, the main inhalation valve assembly 500 opens and the aerosol drug flows into the face mask 200 to the patient.

In this operating mode, the conduit 360 is closed off. Gas flowing through the venturi connector 1150 at the second end 314 flows to the main inhalation valve assembly 500 and can mix with the aerosol drug for delivery to the patient. The bag 1100 is open and serves to collect and store both the gas delivered through the venturi connector 1150 and by means of the nebulizer 1400.

FIG. 23 shows another operating mode, namely, a high efficiency drug and variable concentration oxygen delivery mode. The dual gas reservoir assembly 1200 is provided and includes the first compartment 1220 and the second compartment 1230 segregated by the inner dividing wall 1225.

The directional valve 800 is positioned such that the conduit 360 is closed. The conduits 320, 330 are open to permit gas to flow into the first and second compartments 1220, 1230. Variable concentration of the gas is achieved by manipulating the mechanism 1150 as discussed herein.

FIG. 24 shows another operating mode, namely, another high efficiency drug and variable concentration oxygen delivery mode. The difference between the operating mode of FIG. 24 and the operating mode of FIG. 23 is the position of the directional valve 800. In particular, the directional valve 800 is positioned such that the internal opening 313 is closed off, while the conduit 330 and conduit 360 are open, as well as the end 314. At the second end 314, the venturi style delivery mechanism 1150 is provided for delivering gas (oxygen) to the main body 310. Gas from the mechanism 1150 can flow into the second compartment 1230 of the bag 1200 when the patient exhales. The gas from the mechanism 1150 flows to the patient by passing through the supplemental gas valve assembly 600 and through the HME media 700, thereby heating and humidifying the inhaled gas.

The aerosolized drug flows from the nebulizer 1400 and enters the main body 310 and can only flow to the patient through the main inhalation valve assembly 500 when it opens since the internal opening 313 is closed and thus the aerosol drug cannot flow to the directional valve 800.

This operating mode thus delivers humidified gas (oxygen/air) to the patient along one flow path and the aerosol drug is delivered along another flow path. This arrangement allows preferential flow of medication through path of lower resistance system and additional gas as needed through a relatively higher resistance system thereby maximizing medication delivery.

FIGS. 26 and 27 illustrate another embodiment that is very similar to the system shown in the previous figures except for the inclusion of an intermediary valve assembly 1500. The intermediary valve assembly 1500 is disposed within the internal opening 313 between the conduits 320, 330. The intermediary valve assembly 1500 includes a valve body 1510 and a valve member 1520. The intermediary valve assembly 1500 is in the form of a one way valve that opens in one direction to only allow fluid to flow in the direction from the second end 314 to the first end 312. The intermediary valve assembly 1500 is an inhalation valve that opens on inhalation by the patient. Thus, when the patient inhales, gas can flow through the valve assembly 1500.

FIGS. 28 and 29 show a venturi connector 1600 according to one embodiment for use in the system 100 of the present invention in place of the venturi connector 1150. The venturi connector 1600 includes a connector body 1610 that has a first open end 1612 and an opposite second end 1616. The connector body 1610 has an intermediary lip 1614 with the portion from the lip 1614 to the first end 1612 is a tubular structure with a hollow interior. From the lip 1614 to the end 1616 is a cassette loading port 1620 that is open along the side wall of the connector body 1610. In particular the side wall includes an opening or notch 1625 that permits access to the interior of the body 1610. An inner surface of the side wall of the cassette loading port 1620 includes a locking feature, such as a locking channel 1629 or other structure such as a snap, tab, etc.

The cassette loading port 1620 receives a venturi port cassette 1700. The cassette 1700 is in the form of an elongated tubular structure that has a center bore formed therein. The size of the bore can vary as discussed above with reference to the tubes 1070. The cassette 1700 includes locking feature, such as a locking flange 1640. The cassette 1700 is received within the notch 1625 and the locking flange 1040 mates with the locking channel 1629, thereby removably locking the cassette 1700 in place. The cassette 1700 is positioned such that the bore thereof is axially aligned with the hollow interior of the body 1610 and therefore, gas flowing through the cassette flows into the top portion of the connector body 1610.

The main module 300 and the various components and accessories described herein can be formed of any number of different materials including but not limited to a plastic material.

Now referring to FIGS. 30A and 38-40, a patient interface system (modular pulmonary treatment system) 1800 is shown in accordance with one embodiment of the present invention. The system 1800 is formed of a number of components that mate together to form the assembled system 1800 and in particular, the patient interface system 1800 includes a face mask 1900 and one or more accessories that intimately mate with the face mask 1900.

The illustrated face mask 1900 is merely exemplary in nature and it will therefore be understood that any number of different face mask constructions can be utilized. The face mask 1900 includes a face mask body 1910 that has a front surface or face 1912 and an opposite rear surface or face 1914. The face mask body 1910 includes a nose portion 1916 that is defined by a planar underside 1917 and a front beveled portion 1918. The face mask body 1910 has a peripheral edge 1911 that seats and seals against the face of a user.

As shown in FIGS. 38A-C, a hollow interior of the face mask body 1910 can have a landing or planar floor 1913 that is part of the nose portion 1916.

The face mask body 1910 can be formed of any number of different materials including but not limited to polymeric materials.

As shown in FIGS. 38A-C, the face mask 1900 includes a number of valve assemblies and in particular, includes a first valve assembly 1920 and a second valve assembly 1940. The first valve assembly 1920 is in the form of an inhalation valve assembled and thus opens only when the patient inhales. The first valve assembly 1920 is defined by a primary valve body 1922 that has a first end 1924 and a second end 1926. The valve body 1922 can be in the form of a tubular body with the first end 1924 defining an annular valve seat and the second end 1926 defining a portion that can be connected to another member including a conduit, such as tubing as described herein. The valve seat at the first end 1924 of the valve body 1922 can be constructed to receive a first valve 1930 which can be in the form of a flapper valve. When in the form of a flapper valve 1930, the first end 1924 includes a coupling means (members) 1932 that receive a pin 1934 that pass through bores that are formed through a pair of fingers 1936 that extend from the valve 1930. A hinge is thus formed and the valve 1930 pivots relative to an axis that extends through the pin 1934. The valve 1930 opens only when the patient inhales.

The planar underside 1917 of the nose portion 1916 includes an inhalation port or opening 1919 that is formed therein for receiving the first valve assembly 1920 and in particular, the first end 1924 of the first valve assembly 1920 is disposed within the inhalation port 1919 with the valve 1930 being at least partially disposed within the open interior space of the face mask 1900. The valve 1930 thus opens inwardly into the interior space. Any number of different means can be used to attach the first valve assembly 1920 to the face mask body including mechanical means.

The second valve assembly 1940 is in the form of an exhalation valve and mates with an exhalation port or opening 1941 formed in the nose portion 1916. In the illustrated embodiment, the opening 1941 is a circular shaped opening. The opening 1941 is formed generally perpendicular to the opening 1919 in that a central axis through opening 1919 intersects a central axis through opening 1941 to form a right angle. The opening 1941 is located above the opening 1919.

The second valve assembly 1940 includes an exhalation valve body 1942 that has a first end 1943 that is inserted into the opening 1941 and a second end 1945 that is located outside of the face mask body 1910. The valve body 1942 includes a central post 1946 that is attached to the inner wall of the body 1942 by a support structure, such as a spoke structure. The second valve assembly 1940 includes an exhalation valve 1950 that has a center hole to allow the exhalation valve 1950 to be received on the central post 1946. A valve retainer 1960 (that acts as a cap) mates with the post 1946 to securely attach and hold the valve 1950 in place. The valve 1950 seats against the support structure (spoke structure) when the valve 1950 is in the closed position. The valve 1950 opens only when the patient exhales to allow exhaled air out of the inside of the face mask 1900.

The face mask body 1910 itself preferably does not include internal exhalation ports, valves, openings, vents, etc.

Figure 39B:
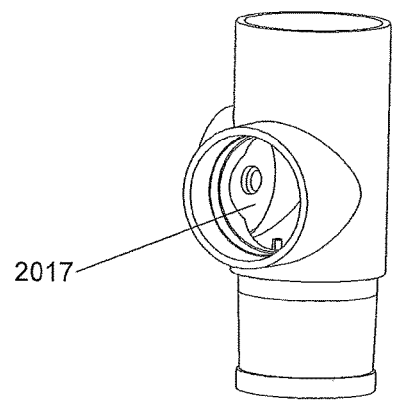
FIG. 39B is perspective view of the connector of FIG. 39A in an assembled condition.
Figure 39A:
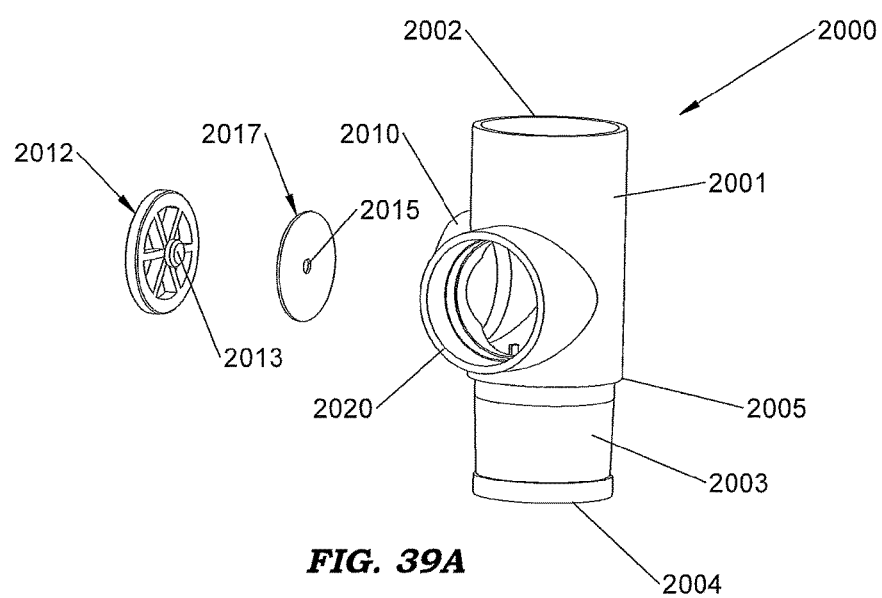
FIG. 39A is an exploded perspective view of a first multi-port valve connector for use in some of the systems of FIGS. 30-37.

In accordance with the present invention, a multi-port valve body (connector or adapter) 2000, as shown in FIG. 39A, is provided for use with the patient interface system (modular pulmonary treatment system) 1800. As described herein, depending upon the precise application, the various components of the system 1800 are configured to achieve the desired treatment objective. The multi-port valve body connector 2000 includes a first end 2002 and an opposing second end 2004. The connector 2000 is a tubular structure with a hollow center that is open at the ends 2002, 2004.

As shown, the connector 2000 does not have a uniform outer diameter but instead can be defined by two different regions, namely, a first region 2001 being located at the first end 2002 and a second region 2003 being located at the second end 2004. The second region 2003 can have an outer diameter that is less than the first region 2001. A shoulder 2005 can be formed between the two regions 2001, 2003.

The connector 2000 also includes a pair of side conduits in the form of a first leg 2010 and a second leg 2020 that extend radially outward from the main body of the connector 2000. The first and second legs 2010, 2020 are spaced from one another (e.g., at a 90 degree angle) and can be formed in the same plane. The legs 2010, 2020 can be circular shaped tubular structures that are in fluid communication with the bore (hollow interior) of the main connector body. It will be understood that the sizes (e.g., diameters) of the legs 2010, 2020 can be different or can be the same.

The first leg 2010 is in the form of an inhalation valve assembly and thus includes a valve seat 2012. The valve seat 2012 is disposed within and secured to the first leg 2010. The valve seat 2012 includes a body that has air passages formed therein and includes a center post 2013 that is received within a hole 2015 formed in an inhalation valve 2017 for attaching the valve 2017 to the valve seat 2012. The inhalation valve 2017 opens when the patient inhales.

The second leg 2020 can be an open leg in that it does not include a valve member but instead is merely a free vent to allow air to flow into and out of the inside of the connector 2000. The second leg 2020 can thus be completely open.

Figure 40:
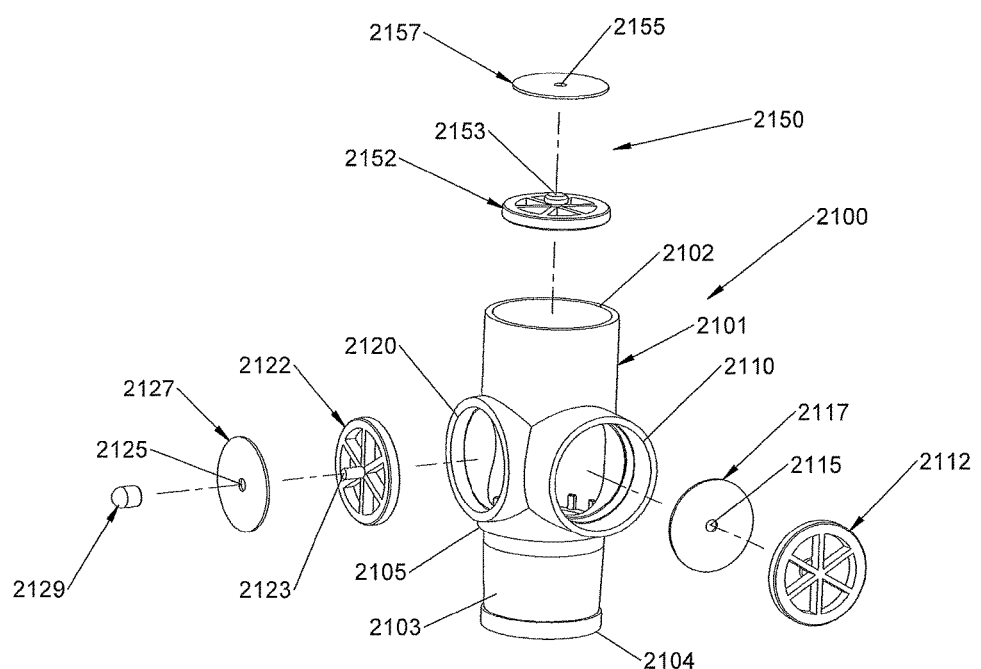
FIG. 40 is an exploded perspective view of a second multi-port valve connector for use in some of the systems of FIGS. 30-37.
Figure 41:
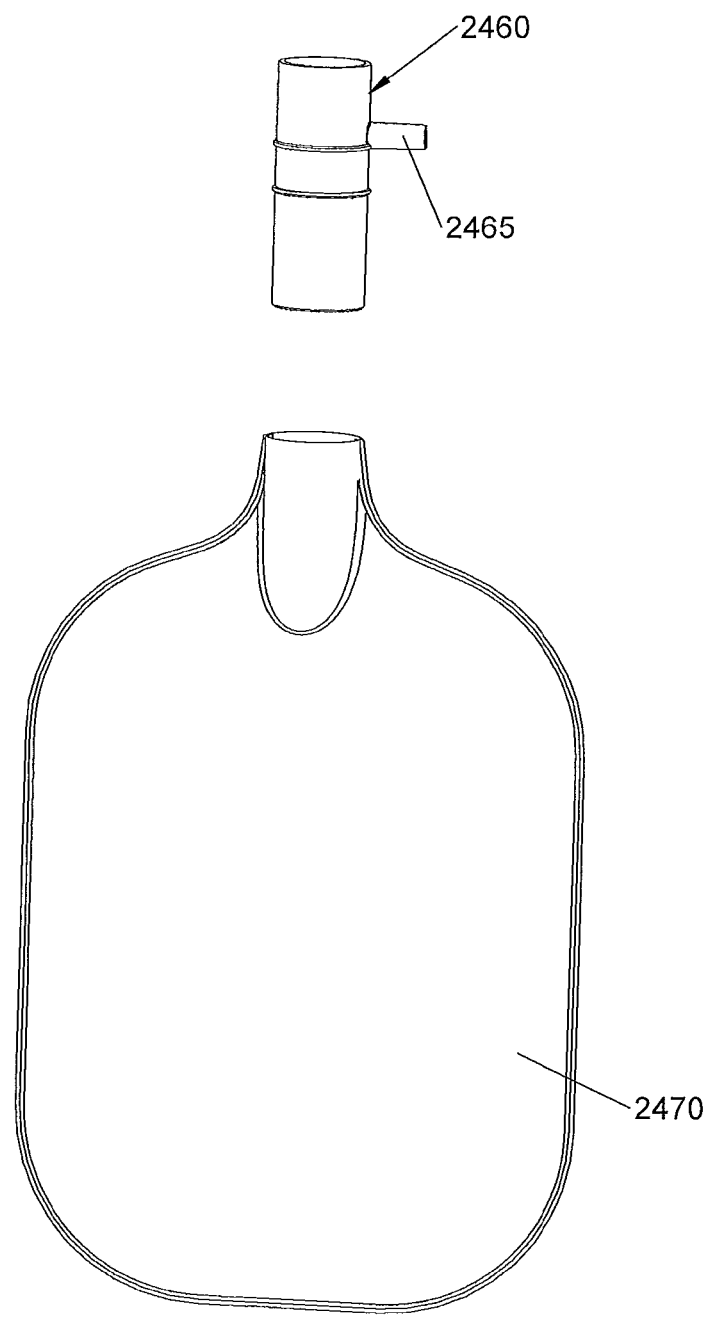
FIG. 41 shows both exploded and assembled perspective views of a single bag reservoir assembly.

The system 1800 also includes another multi-port valve body (connector or adapter) 2100 as shown in FIG. 40. The multi-port valve body connector 2100 is similar to the connector 2000 and includes a first end 2102 and an opposing second end 2104. The connector 2100 is a tubular structure with a hollow center and is open at the ends 2102, 2104.

As shown, the connector 2100 does not have a uniform outer diameter but instead can be defined by two different regions, namely, a first region 2101 being located at the first end 2102 and a second region 2103 being located at the second end 2104. The second region 2103 can have an outer diameter that is less than the first region 2101. A shoulder 2105 can be formed between the two regions 2101, 2103.

The connector 2100 also includes a pair of side conduits in the form of a first leg 2110 and a second leg 2120 that extend radially outward from the main body of the connector 2100. The first and second legs 2110, 2120 are spaced from one another (e.g., at a 90 degree angle) and can be formed in the same plane. The legs 2110, 2120 can be circular shaped tubular structures that are in fluid communication with the bore (hollow interior) of the main connector body. It will be understood that the sizes (e.g., diameters) of the legs 2110, 2120 can be different or can be the same.

The first leg 2110 is in the form of an inhalation valve assembly and thus includes a valve seat 2112. The valve seat 2112 is disposed within and secured to the first leg 2110. The valve seat 2112 includes a body that has air passages formed therein and includes a center post 2113 that is received within a hole 2115 formed in an inhalation valve 2117 for attaching the valve 2117 to the valve seat 2112. The inhalation valve 2117 opens when the patient inhales.

The second leg 2120 is in the form of an exhalation valve assembly and thus includes a valve seat 2122. The valve seat 2122 is disposed within and secured to the second leg 2120. The valve seat 2122 includes a body that has air passages formed therein and includes a center post 2123 that is received within a hole 2125 formed in an exhalation valve 2127 for attaching the valve 2127 to the valve seat 2122. The exhalation valve 2127 opens when the patient exhales. A valve retainer 2129 is used to couple the valve 2127 to the seat 2122.

In addition, the connector 2100 includes a second inhalation valve assembly 2150. The inhalation valve assembly 2150 includes a valve seat 2152. The valve seat 2152 is disposed within and secured to the inner wall of the main body of the connector 2100. In particular, the second inhalation valve assembly 2150 is disposed between the legs 2110, 2120 and the second end 2104. The valve seat 2152 includes a body that has air passages formed therein and includes a center post 2153 that is received within a hole 2155 formed in a second inhalation valve 2157. The second inhalation valve 2157 opens when the patient inhales. The second valve 2157 can be located at the interface between the regions 2101, 2103 below the first leg 2110 and the second leg 2120.

When the patient inhales, the inhalation valves 2117, 2157 open and air can flow to the patient through the main body of the connector 2100 and through the first leg 2110.

Now referring back to FIG. 30A, the system 1800 includes accessories as mentioned above and in particular, FIG. 30A shows system 1800 being configured for low concentration gas (oxygen) delivery. The system 1800 includes a main external conduit 2200 that has a first end 2202 and a second end 2204. The external conduit 2200 is in the form of a tubular structure that permits gas to be delivered from a source to the inside of the face mask and thus be delivered to the patient. The external conduit 2200 can be in the form of a corrugated tube (e.g., 22 mm tube); however, other tube structures and other conduits can be equally used. The length of the external conduit 2200 can be varied (expanded/contracted) as a result of the structure of the conduit 2200.

The external conduit 2200 is fluidly connected to the second end 1926 of the valve body 1922 as by a frictional fit or some other suitable attachment means.

In the embodiment of FIG. 30A, the multi-port valve body connector 2000 is coupled to the conduit 2200 and a venturi device 2300. The second end 2004 of the connector 2000 is attached to the conduit 2200 and the first end 2002 of the connector 2000 is attached to the venturi device 2300. The second region 2003 can be frictionally fit with the conduit 2200 as by being received within the conduit 2200. Similarly, a connector portion of the venturi device 2300 is mated with the first region 2001 of the connector 2000.

In this configuration, the second end 2004 represents a top end of the connector 2000 and the first end 2002 represent a bottom end of the connector. The open second leg 2020 represents a means for entraining air into the external conduit 2200 for mixing with the gas from the gas source that is controlled (metered) by the venturi device 2300 to thereby delivery the proper concentration of gas to the patient.

As the patient inhales, the inhalation valve 1930 in the face mask opens to allow a gas mixture (e.g., mixture of air and oxygen flowing in from venturi 2300 and the entrainment port 2020 of connector 2000 at a concentration between about 24% to about 50%) to flow to the inside of the face mask for breathing by the patient. When the patient exhales, the inhalation valve 1930 closes and the exhalation valve 1950 opens to allow exhaled gas to be exhausted from the face mask 1900.

It will be appreciated that the venturi device 2300 can be any number of different venturi devices that are configured to meter the flow of gas from the gas source to the external conduit 2200. The venturi device 2300 can be of the type which delivers a fixed contraction of gas or can be of a type that delivers a variable concentration of gas. In addition, the venturi device 2300 can be of the type that is disclosed in commonly owned, U.S. patent application Ser. No. 61/610,828, which is hereby incorporated by reference in its entirety.

In the illustrated embodiment, the venturi device 2300 is of a type that allows the gas concentration (oxygen) to be between about 24% to 50%.

Figure 38E:
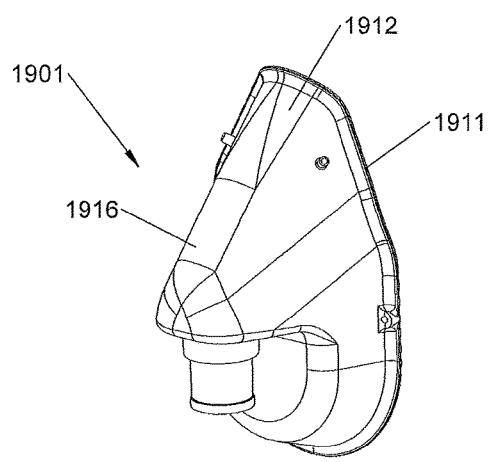
FIG. 38E is a front view of the system of FIG. 38D in the assembled condition.
Figure 38F:
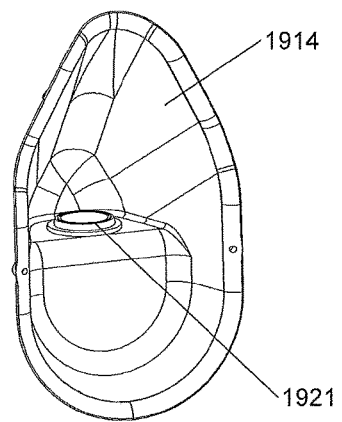
FIG. 38F is a rear perspective view of the system of FIG. 38D.
Figure 38D:
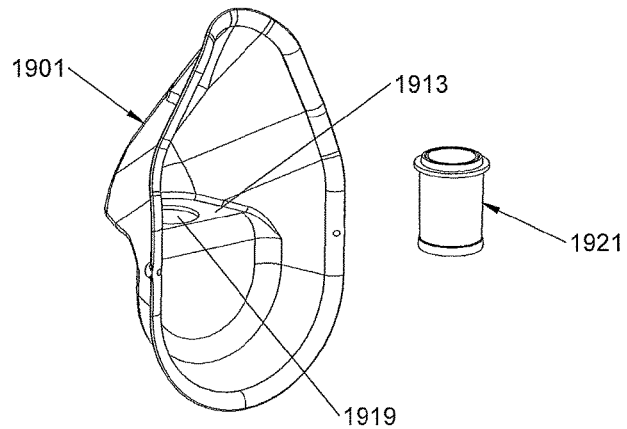
FIG. 38D is an exploded perspective view of a patient interface mask system without valves for use in some of the systems of FIGS. 30-37.

FIG. 30B shows an alternative system 1801 for low concentration gas (oxygen) delivery (e.g., between about 24% and 50%). The system 1801 is similar system 1800 but includes a different face mask 1901 (FIGS. 38D-F). The face mask 1801 does not include the exhalation valve 1950 and does not include primary inhalation valve 1930 within the valve body 1922. Instead the mask 1901 includes an elongated port 1921 a tubular structure that does not include any valve structure and is free of such elements. Fluid can freely flow therethrough into the inside of the mask 1901.

Instead, the system 1801 includes the connector 2100 disposed between the port 1921 and the upper end 2202 of the external conduit 2200. The connector 2100 is arranged such that the first region 2101 is attached to the port 1921 and thus the main valve 2157 is disposed below the side ports 2110, 2120 closer to the external conduit 2200. When the patient inhales, the main inhalation valve 2157 opens to allow the gas (oxygen and air) to flow through the conduit 2200 to the inside of the mask 1901 to the patient. The inhalation valve 2117 serves as an emergency valve and does not normally open or does not open to the degree main valve 2157 opens and instead opens only when there is no other source of gas for the patient. The exhalation valve 2127 in the second port 2120 serves as the main exhalation valve and exhaled air flows therethrough. During exhalation, the gas from the venturi device 2300 remains in the conduit 2200.

An air entrainment port 2301 can be formed in the venturi device 2300 as shown for drawing additional air into the venturi device 2300 and into the conduit 2200 for delivery to the patient.

As with the system 1800, the system 1801 can deliver gas concentrations between about 24% to 50%.

Now referring to FIG. 31 in which a standard dose aerosol drug delivery system 2400 is shown. The system 2400 has many of the components of the system 1800 and therefore, like elements are numbered alike.

In this embodiment, the connector 2000 is attached to the second end 1926 of the valve body 1922. The open end 2004 of the connector 2000 is fluidly attached to a drug delivery means 2410 that delivers aerosolized drug. For example, the drug delivery means 2410 can be in the form of a nebulizer that delivers aerosolized drug. The second leg 2020 of the connector 2000 is connected to a first end 2422 of an elbow shaped connector 2420 while an opposite second end 2424 is connected to one end of the external conduit 2200.

The system 2400 is of an open nature in that the opposite end of the external conduit 2200 remains free of any connection and therefore is open to atmosphere. As a result when the main inhalation valve 1930 within the main body of the connector 2100 is closed (as when the patient is exhaling), the aerosolized drug from the means 2410 flows through the connector 2000 and through the open side port 2020 into the conduit 2200 for storage and future use. End 2204 remains open to atmosphere so the aerosolized drug can be vented if needed to atmosphere when the patient is exhaling through the exhalation valve 1940. The conduit 2200 is adjustable-collapsible and expandable to adjust the length of the reservoir for medication storage during exhalation and thereby enhancing controlled and predictable medication delivery during inhalation Now referring to FIG. 32, a system 2500 is shown in the form of high dose aerosol drug delivery.

The system 2500 includes connector 2000 attached to the open end 1926 of the valve body 1922 that extends through the port 1919. In particular, the connector 2000 is oriented such that the first region 2001 attaches to the valve body 1922 (friction fit) and the second region 2003 attaches to the source of aerosolized medication (e.g., nebulizer 2410) as by a friction fit.

The connector 2420 (e.g., elbow connector) is attached at its first end 2422 to the second leg 2020 of connector 2000. The second end 2424 of the connector 2420 is attached to a reservoir 2450 that receives and stores gas (e.g., aerosolized medication from the nebulizer 2410) under select conditions. The reservoir 2450 can be in the form of a reservoir bag that includes a connector 2460 at an open first end. The connector 2460 is a hollow member and includes a side port 2465 that extends radially outward from one side of the connector 2460. The other end of the connector 2460 is attached to and in fluid communication with the inside of an expandable reservoir bag 2470. The reservoir bag 2470 can be in the form of a 1.5 liter bag that holds overflow aerosolized medication from the nebulizer 2410.

Gas (aerosolized medication) can flow into the bag 2470 when the patient exhales since the inhalation valve 1930 is closed and the second leg 2020 of connector 2000 is always open leading to the reservoir 2470. Exhalation is through valve 1940.

The side port 2465 can be left open (so as to allow the venting of the contents of the reservoir bag 2470 or can be closed with a cap or the like so as to close off the bag 2470 and create a closed system. The side port 2465 permits control of the concentration of the dose and in particular, if the side port 2465 is not closed and left open, the concentration of the aerosolized medication that is delivered to the patient is reduced. Conversely, if the side port 2465 is left closed (capped), the aerosolized medication that flows into the bag 2470 remains collected in the bag 2470 and is not mixed with or vented to atmosphere outside of the bag 2470.

Now referring to FIG. 33A, a system 2600 is shown and is in the form of a 100% non-rebreather gas (oxygen) delivery system.

The system 2600 includes reservoir bag 2470 which is connected to the face mask 1900 via the valve body 1922 and in particular, the reservoir bag 2470 is connected to the connector 2000 which in turn is connected to the valve body 1922. More specifically, the connector 2000 is connected at region 2001 to the end 1926 of the valve body 1922 and the region 2003 of the connector 2000 is connected to the connector 2460 associated with the reservoir bag 2470.

The inhalation valve 2017 of the connector 2000 serves as an emergency inhalation valve to allow air to be delivered to the patient under select conditions.

The side port 2465 of the connector 2460 is fluidly connected to a gas source, such as oxygen, for delivery to the patient. The connector 2460 does not include an inhalation valve within the main body thereof (unlike the connector 2100) and therefore, gas flowing through the side port 2465 flows into the connector 2460 and the reservoir bag 2470 and into the valve body 1922 such that when the patient inhales and the inhalation valve 1930 opens, the gas from the gas source and reservoir bag 2470 is delivered to the inside of the face mask 1900 to the patient.

The gas stored in the reservoir 2470 is available once the patient inhales since it can freely flow through the connector 2460 and valve body 1922 to the patient when valve 1930 is open.

It will be appreciated that a conduit, such as tubing or the like, is used to connect the gas source to the side port 2465.

FIG. 33B shows an alternative system 2601 (100% non-rebreather gas (oxygen) delivery) using the face mask 1901. The connector 2100 is connected to the port 1921 at the first region 2101 thereof. Thus the main inhalation valve 2157 is located below the side ports 2110, 2120. The second region 2103 is connected to the connector 2460 of the reservoir 2450 (bag 2470).

The inhalation valve 2117 in the side port 2110 is an emergency valve as discussed herein and the exhalation valve 2127 disposed in the second port 2120 is the main exhalation valve. The side port 2465 is connected to the gas source (e.g., oxygen) and when the patient inhales and valve 2157 opens, the gas is delivered to the inside of the face mask 1901 to the patient. When the patient exhales and valve 2157 is closed, the gas flows to the bag 2470 and exhaled air is vented through the side port 2120 (valve 2127).

Now referring to FIG. 34A, a system 2700 is shown in the form of low concentration gas (oxygen) delivery with heat and moisture exchange. The system 2700 includes components previously discussed; however, these parts are arranged to provide the intended treatment. In this embodiment, a heat and moisture exchanger (HME) 2710 is used and is configured to attach to different components and in particular, includes a first end 2712 and an opposite second end 2714. The ends 2712, 2714 act as connector ends. In between the ends 2712, 2714, the HME 2710 includes HME media to perform the heat and moisture exchange. As previously mentioned, the HME media is constructed to heat and humidify inhaled air and in the present system 2700, the HME media is disposed within the hollow tubular structure of the HME 2710. The HME media is thus in fluid communication with both the gas to the patient as discussed below for inhalation by the patient and also exhaled gas that flows from the patient as discussed below.

In the HME mode, the main exhalation valve 1940 of the face mask 1900 is capped so as to disable this valve and this venting port during exhalation. In addition, the main inhalation valve 1930 of the face mask 1900 is also disabled so as to allow exhaled gas to flow into and through the valve body 1922. Any number of different means can be used to disable the inhalation valve 1930 and in one embodiment, the HME device 2710 includes an element (not shown) for disabling the main inhalation valve 1930. For example, the HME device 2710 can include an extension (pin, rod, etc.) that is integrally attached thereto and extends outwardly therefrom and can be received within valve body 1922 so as to forcible contact and open the valve 1930 as by lifting the valve 1930 away from its seat 1924 (this disables the valve 1930 by preventing it from closing). Since the exhalation valve 1940 is capped and the inhalation valve 1930 is disabled, both inhalation and exhalation is performed through the valve body 1922 and through the HME 2710. This is required since for the HME 2710 to function, the HME media needs to be in fluid contact with the warm, moist exhaled gas and also in communication with the gas that is inhaled by the patient.

The end 2712 is connected to the end 1926 of the valve body 1922, while the end 2714 is connected to the first region 2101 of the connector 2100. The region 2103 of the connector 2100 is connected to the first end 2202 of the external conduit 2200. The second end 2204 of the conduit 2200 is connected to the venturi device 2300. As mentioned herein, the venturi device 2300 can be any number of different types of venturi devices including but not limited to a variable venturi device in which the concentration of the gas being delivered from a gas source to the external conduit 2200 and then ultimately to the patient can be varied.

The inhalation valve 2117 that is disposed in the first leg 2110 serves as an emergency valve. The exhalation valve 2127 disposed in the second leg 2120 serves as the main exhalation valve of the system since the exhalation valve 1940 of the face mask 1900 is closed as discussed above.

The system 2700 includes an air entrainment port to permit air to be drawn into the external conduit 2200. The air entrainment port can be formed in any number of different locations so long as it functions to permit air to flow into the conduit 2200 to mix with the gas delivered through the venturi device 2300. For example, a connector with an air entrainment port (i.e., an open side port) can be connected between the external conduit 2200 and the venturi device 2300. Alternatively, the external conduit 2200 can include an air entrainment port (i.e., an open port formed in the side of the external conduit 2200) to allow air to flow into the external conduit 2200 for mixing with the gas (oxygen) from the gas source. Alternatively, the venturi device 2300 can include an air entrainment port (an open side port) that is in fluid communication with atmosphere to draw air therein for mixing with the gas delivered through the venturi device 2300.

The system 2700 is a low concentration gas (oxygen) delivery system since the gas concentration can be controlled by the venturi device 2300 in the manner described hereinbefore. As mentioned earlier, the venturi device 2300 is configured to deliver low concentration (e.g., about 24% to 50%) of gas.

The system 2700 operates in the following manner. When the patient inhales, the inhalation valve 2157 in the connector 2100 opens and gas can flow into the external conduit 2200 by way of the venturi mechanism 2300. The inhalation valve 1930 is disabled (remains open) and therefore, the mixed gas flows through the external conduit 2200 to the inside of the face mask 1900. The mixed gas flows through the HME media 2710 and therefore, is heated and humidified before delivery to the patient. Upon exhalation, the exhaled gas flows through the inside of the face mask 1900 to the HME device 2710 where it contacts the HME media is exhaled through exhalation valve 2127. As mentioned, the HME media serves to capture heat and moisture from the exhaled air. This allows recharging of the HME media upon each exhalation, thereby allowing the inhaled air to be heated and humidified.

Figures 34B, 35A:
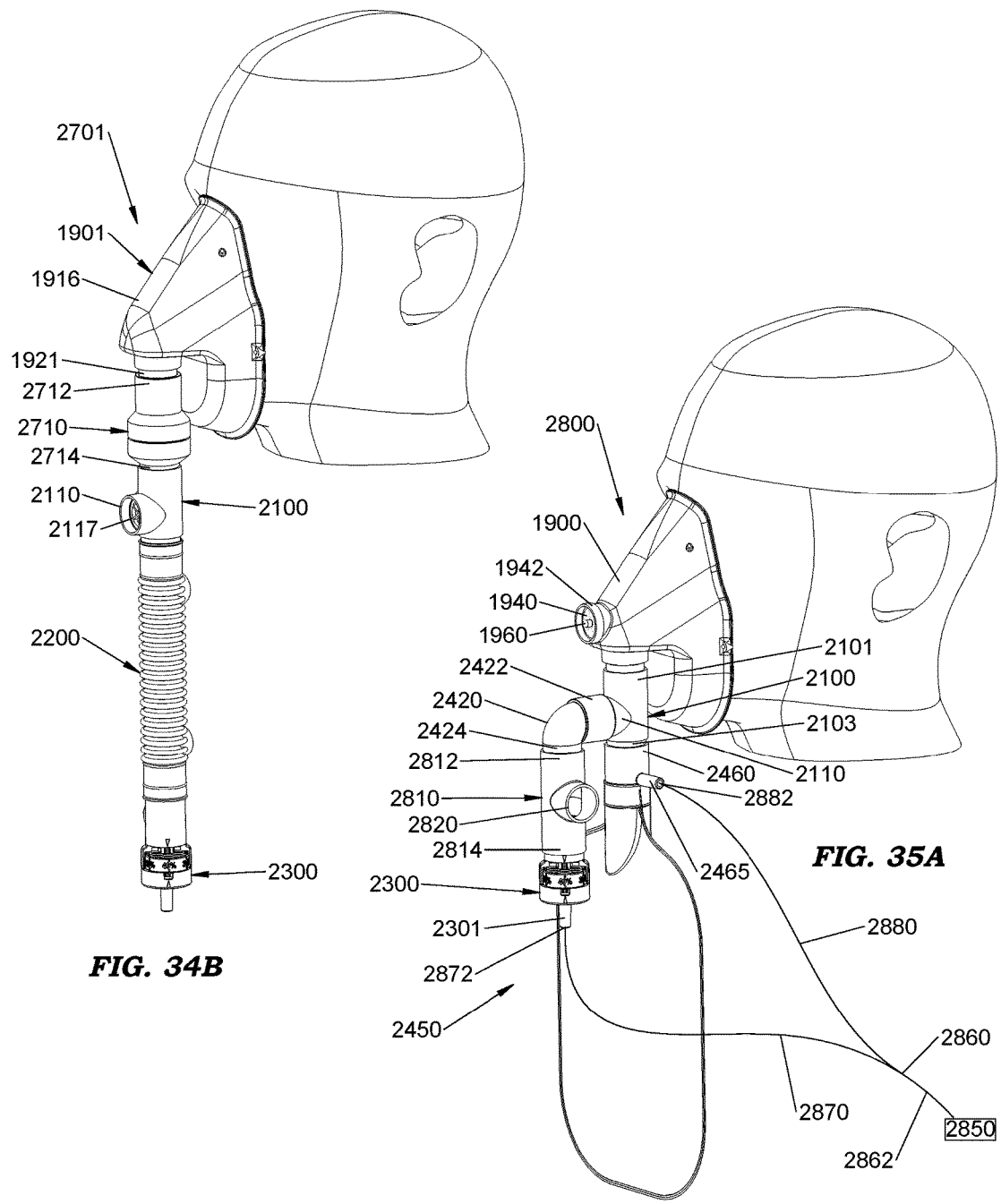
FIG. 34B is a side perspective view of a patient interface system according to another embodiment for low concentration gas (oxygen) delivery with heat and moisture exchange.
FIG. 35A is a side perspective view of a patient interface system according to another embodiment for high concentration gas (oxygen) delivery.

FIG. 34B is similar to FIG. 34A and discloses a system 2701 which uses mask 1901. The main inhalation valve is valve 2157 with the valve 2117 being an emergency valve as discussed herein. The exhalation valve 2127 is the main exhalation valve of the system. Since connector 2100 is below the HME 2710, both inhaled and exhaled air passes through the HME. The advantage of this mask assembly is that it does not require disabling of inhalation and exhalation valves as described before for embodiment 34A mask where valves 1930 and 1960 had to be disabled.

The venturi device 2300 can be of a variable type and allows the concentration of gas (oxygen) to be varied and can include an air entrainment port to allow air to flow into the device 2300. The concentration can be varied between about 24% to 50%. Any number of different venturi devices 2300 can be used.

Now referring to FIG. 35A in which a system 2800 is shown. The system 2800 is a high concentration gas (oxygen) delivery system without heat and moisture exchange.

In this embodiment, the connector 2100 is connected at its first region 2101 to the end 1926 of the valve body 1922 and the second region 2103 is connected to the reservoir 2450 (e.g., reservoir bag). In particular, the second region 2103 is attached to the connector 2460 associated with the reservoir 2450. The connector 2460 includes the side port 2465.

Connector 2420 (e.g., elbow connector) is attached at its first end 2422 to the first leg 2110 of connector 2100 and thus, the inhalation valve 2117 is in fluid communication with the connector 2420 and allows fluid to flow into the face mask 1900 under select conditions. The second end 2424 of the connector 2420 is attached to a tee connector 2810 that has a first end 2812 and an opposite second end 2814 with the first end 2812 being attached to the second end 2424 of the connector 2420 and an opposite second end 2814 being attached to the venturi device 2300. The tee connector 2810 includes an intermediate port 2820 that is located between the ends 2812, 2814. The intermediate port 2820 is an open port that functions as an air entrainment port for drawing air into the system at a location above the venturi device 2300 and therefore, the air drawn into the tee connector 2810 is mixed with the gas delivered through the venturi device 2300.

The venturi device 2300 has an inlet port 2301 associated therein in which the gas (e.g., oxygen) is delivered.

As in the other embodiments, the venturi device 2300 can be any number of different types of venturi devices.

In FIG. 35A, a gas source 2850 is shown. The gas source 2850 can be any number of different types of gas sources and the gas can be any number of different types of gas including but not limited to oxygen (e.g., it can also be heliox, etc.). A wye connector 2860 is provided and includes a main leg 2862 that is connected to the gas source 2850 and a pair of split first and second legs 2870, 2880. A distal end 2872 of the split leg 2870 is connected to the inlet port 2301 of the venturi device 2300 for delivering gas thereto. A distal end 2882 of the split leg 2880 is attached to the side port 2465 of the connector 2460 that is associated with the reservoir 2450.

As described in detail in Applicant's U.S. Pat. No. 7,841, 342, which is hereby incorporated by reference in its entirety, the first and second legs 2870 and 2880 can function to meter the flow of the gas to the respective inlet (i.e., to the inlet 2301 and to the side port 2465). For example, the first and second legs 2870, 2880 do not necessarily have a uniform construction relative to one another but instead, the restrictive inside diameter of one leg 2870, 2880 can be different than the other leg for changing the gas flow rate to the respective port. For example, by reducing the diameter of the leg, the flow rate of the gas is reduced, thereby allowing the user to customize and tailor the concentration of the gas that is delivered to the patient. The system 2800 is configured such that gas concentrations of between about 50% and about near 100% is delivered under select conditions described below.

To achieve maximum gas concentration, the intermediate port 2820 of the tee connector 2810 is capped to prevent air from flowing into the tee connector 2810 and by constructing the tubing wye connector 2860 such the flow rates to the venturi device 2300 and the connector 2460 maximize gas concentration. For example, the leg 2870 connected to the venturi device 2300 can have a reduced gas flow rate compared to leg 2880 and thus, a greater amount of gas is delivered to the patient through the connector 2460 which is located below the internal inhalation valve 2157 of the connector 2100. Thus, when the patient inhales and the inhalation valve 2157 opens, the gas from the gas source flows through the connector 2460 and the valve body 1922 and into the inside of the face mask 1900 to the patient.

When the patient inhales, gas is also delivered through the venturi device 2300 and through the elbow connector 2420 and the first leg 2110 of the connector 2100 due to the inhalation valve 2117 in the first leg 2110 opening. Thus, both the gas delivered through the first leg 2870 and through the second leg 2880 meet in the connector 2100 and is delivered into the primary valve body 1922 and to the patient as the valve 1930 opens. It will be appreciated that each of the gas flowing through the first leg 2870 and the gas flowing through the second leg 2880 has to pass through one inhalation valve (i.e., valves 2117, 2157) before meeting in the first region 2101 of the connector 2100 and thus the relative flow paths have equal resistance in terms of flow to the face mask 1900. Thus, one route is not favored over the other at least in terms of flow resistance associated with the individual flow paths. This permits the customization of the gas concentration to be possible and controlled as described herein. Thus, altering/modifying the flow properties (flow rate) of the legs 2870, 2880 has direct effects on the overall concentration of the gas delivered to the patient.

It will be appreciated that two separate conduits can be used instead of the wye-connector 2860, with one conduit connected to the venturi device 2300 and the other conduit connected to the port 2465. The two conduits (tubes) can be connected to the same gas source 2850 or can be attached to separate gas sources (which can be the same or different gases).

Figures 35B, 36A:
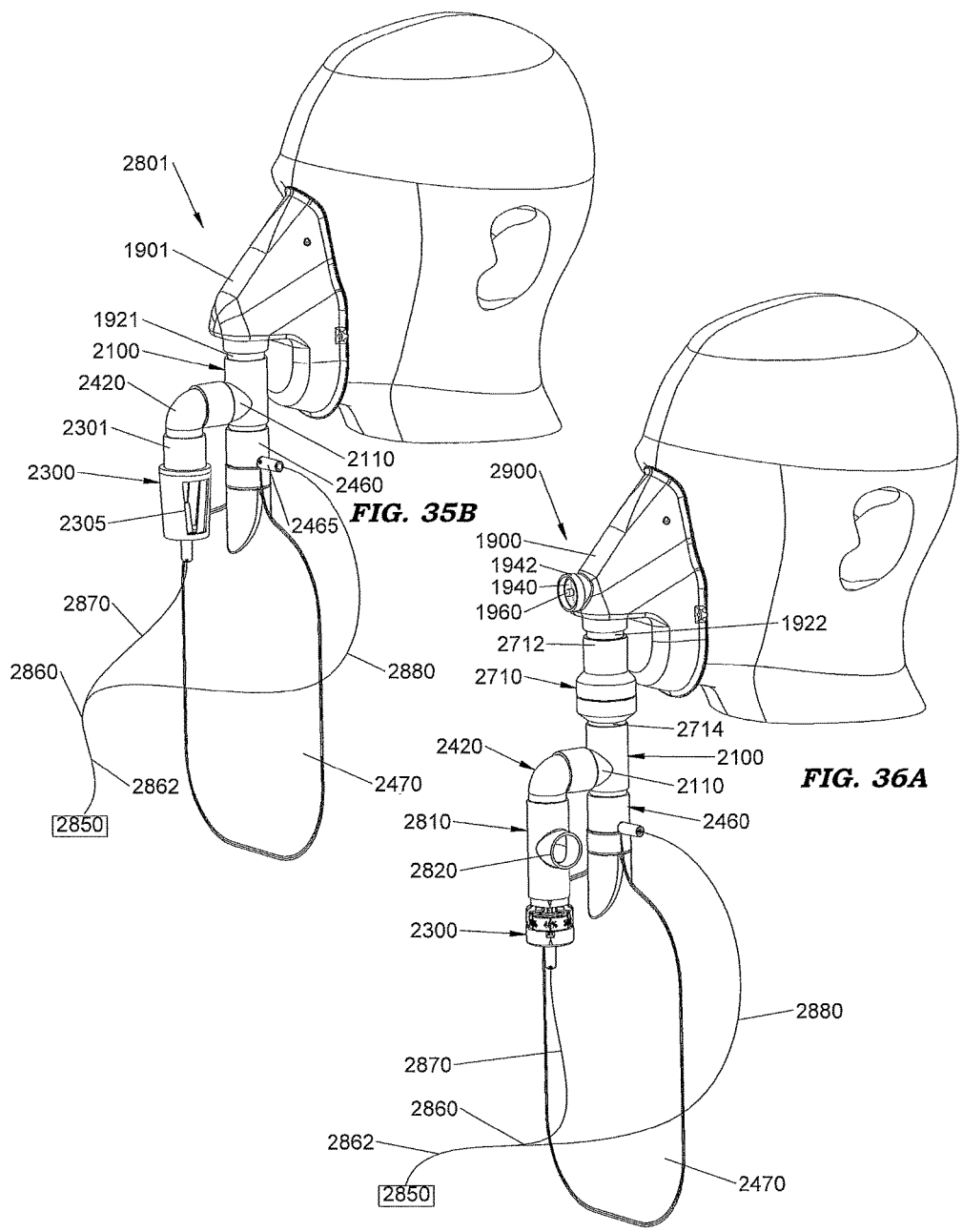
FIG. 35B is a side perspective view of a patient interface system according to another embodiment for high concentration gas (oxygen) delivery.
FIG. 36A is a side perspective view of a patient interface system according to another embodiment for high concentration gas (oxygen) delivery with heat and moisture exchange.

FIG. 35B shows a system 2801 using mask 1901. The port 1921 is connected to the connector 2100 with the side port 2110 being connected to the elbow connector 2420. The other end 2424 of the elbow connector 2420 is connected to the venturi device 2300. The device 2300 includes an inlet port 2301 connected to gas source 2850. The illustrated device 2300 is of a type that allows the flow rate to be adjusted and also permits adjustment of the degree of air entrainment as by having an adjustable air entrainment window (as by rotating the device to change the degree of openness of the window 2305, thereby altering the gas concentration).

The exhalation valve 2127 is the means for exhaling air and the valve 2117 is an emergency valve as discussed herein. As in the previous embodiment, the flow paths through the device 2300 and connector 2460 offer equal degrees of resistance since each has one inhalation valve within the flow path.

As in FIG. 35A, two conduits instead of a wye-connector 2860 can be used and more than one gas source can be used in FIG. 35B.

FIG. 36A shows a system 2900 that is very similar to system 2800 with the exception that system 2900 is high concentration gas (oxygen) delivery with heat and moisture exchange. The set-up and arrangement of the components of the system 2900 is virtually identical to the system 2800 with the one exception being the inclusion of the HME device 2710 between the connector 2100 and the primary valve body 1922. The first end 2712 of the HME device 2710 is attached to the valve body 1922, while the second end 2714 is attached to the first region 2101 of the connector 2100.

As with the previous HME application described herein, the main exhalation valve 1940 is capped (disabled) and the primary inhalation valve 1930 is disabled so as to remain always open. This causes both inhaled and exhaled air (gas) to flow through the HME device 2710 thus causing the media to be charged.

The tee-connector 2810 can include the port 2820. Gas flows to the patient when inhaling due to the opening of valves 2117, 2157. The main exhalation is at exhalation valve 2127 in side port 2120 of the connector 2100.

As in the other embodiment, the wye-connector can be substituted with two conduits attached to the device 2300 and the connector port 2465 and one or more gas sources can be used.

FIG. 36B shows system 2901 using face mask 1901 in which the HME media 2710 is connected to the port 1921. The venturi device 2300 is connected to port 2110 using elbow connector 2420 and the reservoir (bag 2470) is connected via connector 2460. Thus, gas flowing through the port 2465 being stored in reservoir bag 2470 flows through valve 2157 (when patient inhales) and the gas flowing through the venturi device 2300 and connector 2420 flows through the valve 2117 in side port 2110.

Exhalation is through the valve 2127 in side port 2120 of the connector 2100.

As in the other embodiment, the wye-connector can be substituted with two conduits attached to the device 2300 and the connector port 2465 and one or more gas sources can be used.

FIG. 37 shows a system 3000 which is a high dose drug deliver with 100% gas (oxygen) delivery.

Figure 42:
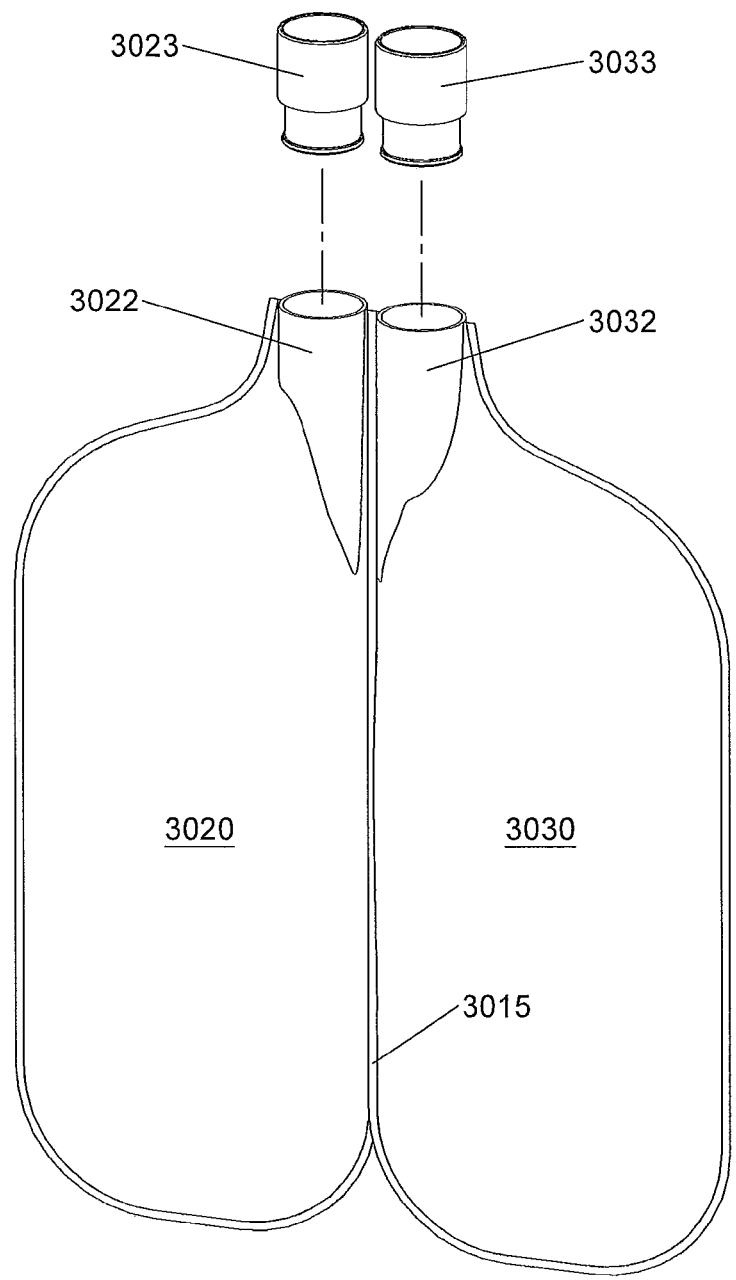
FIG. 42 shows both exploded and assembled perspective views of a dual bag reservoir assembly.
Figure 43:
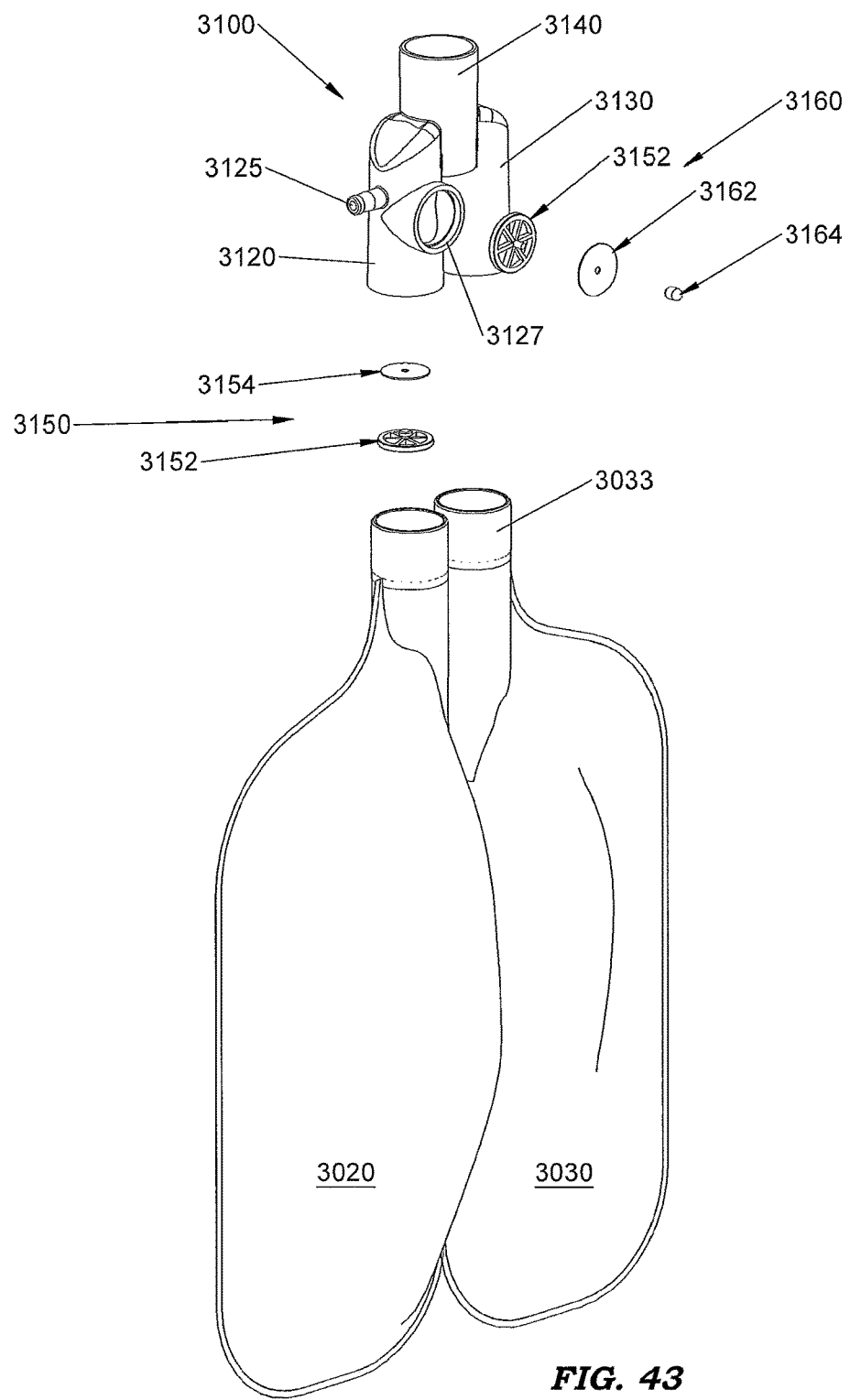
FIG. 43 shows both exploded and assembled perspective views of a dual bag reservoir system used in embodiment 37 for high dose drug delivery with 100% gas (oxygen) delivery system.

The system 3000 uses face mask 1900 and a first region 2001 of the connector 2000 is connected to the valve body 1922. The open side port 2020 is attached to the elbow connector 2420 at end 2422 thereof. The other end 2424 of the connector 2420 is attached to a dual reservoir 3010. As shown also in FIGS. 42-43, the dual reservoir 3010 can be in the form of a bag that has a first compartment 3020 and a second compartment 3030. The compartments 3020, 3030 can be divided by a shared inner wall 3015. As shown in FIG. 42, the compartments 3020, 3030 has openings or ports 3022, 3032 and can include connector 3023, 3033 that are attached to the ports 3022, 3032 to allow the bag 3010 to be easily attached to another structure.

In particular, a U-connector 3100 (FIG. 43) is used to connect the reservoir 3010 to the elbow connector 2420. The U-connector 3100 includes a connector body 3110 that includes a first conduit section 3120 and an adjacent, separate second conduit section 3130 that merge into an upper conduit section 3140. The first conduit section 3120 has a side inlet 3125 and a side port 3127, as well as an inhalation valve 3150 formed of a valve seat 3152 and inhalation valve 3154 that mates thereto as described previously with respect to other inhalation valves. The inhalation valve 3150 is positioned within the first conduit section 3120 at a location above the ports 3125, 3127. The side port 3127 contains a relief valve 3160 and includes a relieve valve seat 3152 and a relief valve 3162 that seats thereto and a valve retainer 3164. The relief valve 3160 opens when excess pressure exists in the compartment 3020. The second conduit section 3130 is free of ports and valves and is merely open.

The side port 3125 is connected to a gas source that flows into the first compartment 3020 for storage therein so as to provide a supplemental gas source for the patient during inhaling.

The device 2410 (nebulizer) is connected to the region 2003 of the connector 2000. The gas from the nebulizer 2410 is in free communication with bag 3030 and thus when the patient exhales and the inhalation valve 1930 is closed, the aerosolized gas from the nebulizer 2410 flows into the compartment 3030 for storage therein. The supplemental gas stored in the compartment 3020 can flow to the patient when the inhalation valve 3154 opens to allow the supplemental gas to flow through the first conduit section 3120 to the section 3140 and then through connectors 2420, 2000 to the main valve body 1922 and through the main inhalation valve 1930 during inhalation. Thus, the gas flow path from the nebulizer 2410 is preferred since the gas only passes through one inhalation valve (1930) as opposed to the supplemental gas which passes through two inhalation valves 3154, 1930. There is greater resistance in the flow path of the supplemental gas.

Exhalation is through valve 1940 in the mask 1900.

Figure 44:
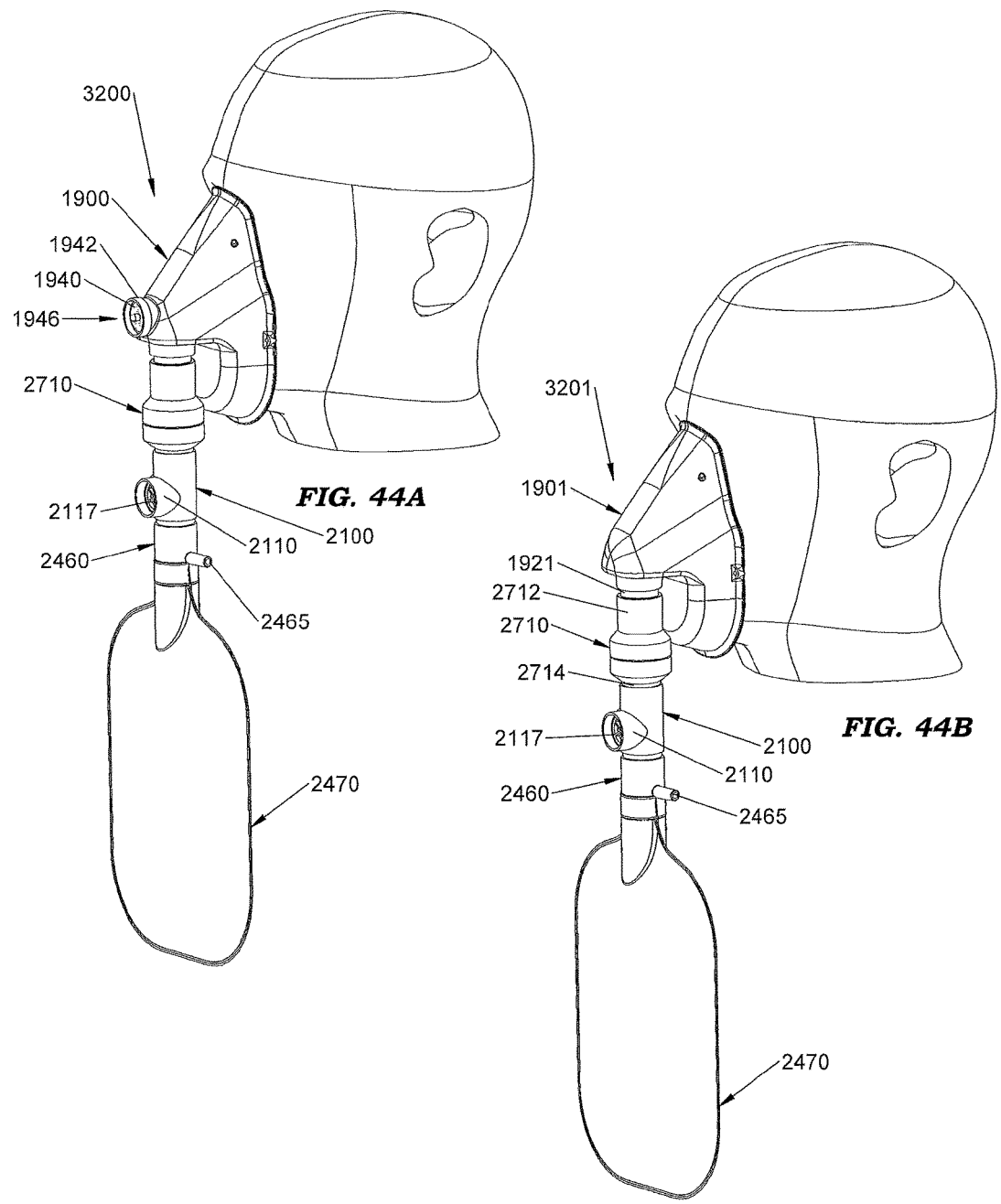
FIG. 44A is a 100% non-rebreather gas (oxygen) delivery with heat and moisture exchange.
FIG. 44B shows another embodiment for 100% non-rebreather gas (oxygen) delivery with heat and moisture exchange.

FIG. 44A shows a system 3200 that uses mask 1900 and is in the form of 100% non-rebreather gas (oxygen) delivery with heat and moisture exchange. The HME device 2710 is connected to the valve body 1922. As in some of the other HME embodiments, the exhalation valve 1940 is capped and the primary inhalation valve 1930 is disabled (so as to remain open all the time). For example, the HME 2710 can include an extension that forces the valve 1930 open.

The inhalation valve 2117 is an emergency valve that can open during select conditions.

The gas flows into the port 2465 and upon inhalation the valve 2157 opens to allow flow to the patient. Exhalation is through the valve 2127.

FIG. 44B is a system 3201 using the face mask 1901. The HME device 2710 is connected to the primary port 1921 of the mask 1901 at end 2712 and the opposite end 2714 of the HME device 2710 is attached to the first region 2101 of the connector 2100. The region 2103 of the connector 2100 is connected to the connector 2460. Exhalation is through the exhalation valve 2127 in the connector 2100. The inhalation valve 2157 is located above the side port 2465 and the gas flows to the mask 1901 when the valve 2157 opens during inhalation and when it closes during exhalation, the gas is stored in the bag 2470 to be available during the next breath.

The gas source is connected to the port 2465.

Figures 45, 46:
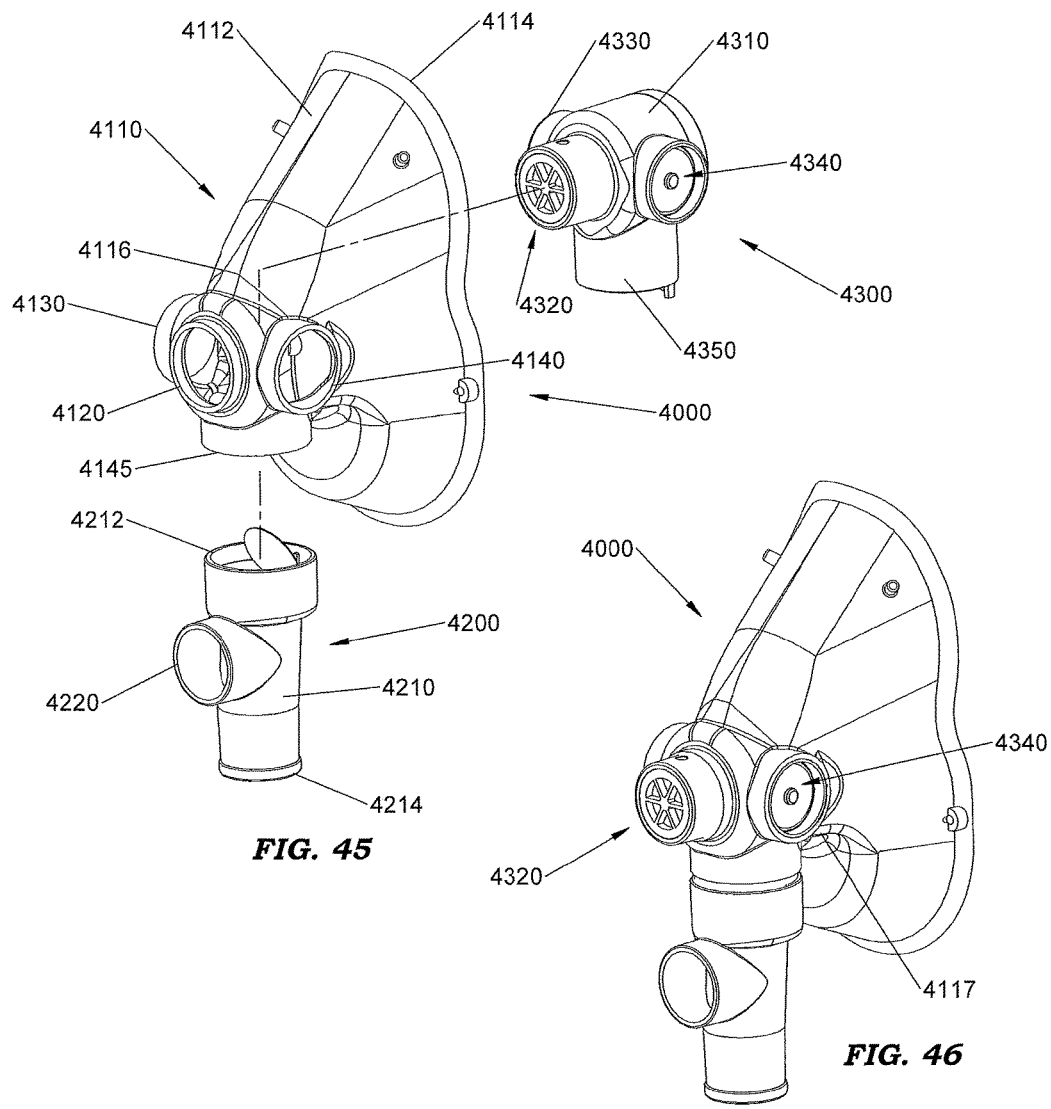
FIG. 45 is a side and front perspective view of a patient interface system according to a different embodiment and showing a mask valve assembly and a primary gas valve assembly exploded therefrom.
FIG. 46 is a side and front perspective of the assembled patient interface system of FIG. 45.

FIGS. 45 and 46 illustrate a patient interface system (modular pulmonary treatment system) 4100 in accordance with one embodiment of the present invention. The system 4100 is formed of a number of components that mate together to form the assembled system 4100 and in particular, the patient interface system 4100 includes a patient interface member (face mask) 4110.

The illustrated face mask 4100 includes a face mask body 4110 that has a front surface or face 4112 and an opposite rear surface or face 4114. The face mask body 4110 includes a nose portion 4116 that is defined by an underside 4117. The face mask body 4110 can be formed of any number of different materials including but not limited to polymeric materials.

FIG. 45 shows the body 4110 in shell form with some of the operating components being exploded therefrom. While shown in exploded form, it will be understood that the assemblies 4200, 4300 are intended to be integral with the mask body 4110 and not separable therefrom by a user.

As shown in the shell form, the body 4110 has a number of openings formed therein and in particular, the body 4110 includes a first (front) opening or port 4120; a pair of side openings or ports 4130, 4140 and a bottom opening or port 4145. The openings 4120, 4130, 4140 are formed in the nose portion 4116 of the mask body 4110. The two side openings 4130, 4140 are located opposite one another such that they are formed along the same axis and an axis extending centrally through the front opening 4120 is preferably at a right angle to the axis extending centrally through the two side openings 4130, 4140. A bottom opening 4145 can be formed such that an axis extending centrally therethrough is perpendicular the axis extending centrally through the two side openings 4130, 4140 and can also be perpendicular the axis extending centrally through the front opening 4120.

The primary gas valve assembly 4200 is in the form of an elongated hollow body 4210, such as a tubular structure that is defined by a first end 4212 and an opposing second end 4214. Between the first and second ends 4212, 4214, there is a side port 4220 that is open to atmosphere. The functionality of the side port 4220 is discussed below and generally, the side port 4220 can function as a secondary gas port. The first end 4212 is intended to mate with the bottom port 4350 of the valve body 4310 such that the hollow interior of the body 4210 communicates with the bottom port 4350 of the valve body 4310. Fluid (gas) that thus flows longitudinally through the hollow body 4210 enters or exits the mask body 4110 through the bottom port 4350 of the valve body 4310. In use, the side port 4220 faces outwardly as shown.

It will be understood that the primary gas valve assembly 4200 and the mask valve assembly 4300 are intended to be integral to the mask body 4110 and thus, are not intended to be separated from the mask body 4110. For example, the assembly 4200 and the assembly 4300 can be permanently assembled with the mask body 4110 at the point of manufacture. Any number of different techniques can be used to attach assemblies 4200, 4300 to the mask body 4110 including but not limited to using a non-releasable snap-fit. When attached, the primary gas valve assembly 4200 provides a conduit member that extends downwardly from the nose portion of the mask body 4110.

The mask valve assembly 4300 is intended for placement within the hollow interior of the mask body 4110 and as described herein, the mask valve assembly 4300 provides a plurality of valves that operate during use of the system.

The mask valve assembly 4300 includes a valve body 4310 that is intended for insertion into and coupling within the hollow interior of the mask. The body 4310 has a complementary construction as the nose portion of the face mask since it is intended to be placed therein. The body 4310 thus houses a plurality of valves and in particular, the body 4310 includes a first valve member 4320, a second valve member 4330, and a third valve member 4340. The first valve member 4320 is disposed within the front opening 4120 of the mask body 4110. The body 4310 also includes second and third valve members 4340, 4350 that are opposite one another in that they are formed along the same axis. The second and third valve members 4330, 4340 are disposed within the pair of side openings or ports 4130, 4140, respectively, of the mask body 4110.

As best shown in FIG. 51, the first valve member 4320 serves as an inhalation valve, while the second and third valve members 4330, 4340 serve as exhalation valves. As shown and according to one exemplary embodiment, the first valve member 4320 is formed of a valve seat 4322 and a valve 4324 that is coupled to the seat 4322 as by being seated over a valve retention knob 4345 that is formed as part of the valve seat 4322. Since the valve member 4320 functions as an inhalation valve, the valve 4324 is a one-way valve that lifts off of the seat when the patient inhales. The valve seat 4322 can have a spoke construction as shown to permit air flow therethrough.

As described below, the first valve member 4320 acts as an emergency air valve.

The second valve member 4330 is similar or identical to the first valve member 4320 and is formed of a valve seat 4334 and a valve 4332 that is coupled to the seat 4334 as by being seated over a valve retention knob 4345 that is formed as part of the valve seat 4334. Since the valve member 4330 functions as an exhalation valve, the valve 4334 is a one-way valve that lifts off of the seat when the patient exhales. The valve seat 4334 can have a spoke construction as shown to permit air flow therethrough.

The third valve member 4340 is similar or identical to the second valve member 4330 and is formed of a valve seat 4342 and a valve 4344 that is coupled to the seat 4342 as by being seated over a valve retention knob 4345 that is formed as part of the valve seat 4342. Since the valve member 4340 functions as an exhalation valve, the valve 4344 is a one-way valve that lifts off of the seat when the patient exhales. The valve seat 4342 can have a spoke construction as shown to permit air flow therethrough.

As mentioned and shown, the two valve members 4330, 4340 are disposed 180 degrees apart.

As best shown in the side elevation view of FIG. 52, the body 4310 includes a rear notch 4315 that is formed therein. The notch 4315 functions to receive and mount an HME member within the face mask body as described below. The body 4310 also includes a key slot 4317 and a hinge pin retention posts 4319 that are located along the rear face of the body 4310 below the notch 4315.

As shown in FIGS. 46-53, the primary gas valve assembly 4200 and the mask valve assembly 4300 can be configured to mate directly to one another and thus be coupled to one another while being maintained integral to the mask body 4110. As shown in FIG. 47, the primary gas valve assembly 4200 includes a key 4201 in the form of a protrusion that is designed to be received within the key slot 4317 for coupling the two together. The key 4201 and key slot 4317 thus serve as locating members for properly orienting the primary gas valve assembly 4200 and a mask valve assembly 4300. The body of the primary gas valve assembly 4200 includes a locating shoulder 4211.

In accordance with the present invention, a primary inhalation valve 4250 is disposed within the body of the primary gas valve assembly 4200. As best shown in the cross-sectional view of FIG. 50, the body of the primary gas valve assembly 4200 includes an annular seat 4260 formed therein and located above the secondary gas (side) port 4220. Along the annular seat 4260, a mounting cradle 4270 is formed. The primary inhalation valve 4250 is of a swing type in that the inhalation valve pivots or swings between open and closed positions depending upon the degree of force and the direction of the force. The primary inhalation valve 4250 includes a valve member 4252 and a pin 4255 that is received through a bore formed in an enlarged section of the valve member 4252. In the illustrated embodiment, the valve member 4252 generally has a circular shape; however, other shapes are possible. The pin 4255 is thus coupled to the valve member 4252 by being disposed within the bore, thereby allowing the two parts to move (rotate) independently with respect to one another. The hinge pin 4255 has a length that is such that the ends thereof extend beyond the sides of the valve member 4252, thereby allowing the hinge pin 4255 to be received within the mounting cradle 4270 for attaching the primary inhalation valve 4250 to the body of the primary gas valve assembly 4200. As shown in FIG. 50, the primary inhalation valve 4250 is disposed above the side port 4220. The opening (port) 4251 which is covered by the primary inhalation valve 4250 in the closed position thereof can be an eccentric opening 4251 relative to the body of the primary gas valve assembly 4200 as shown in FIG. 48.

In accordance with one embodiment of the present invention, the primary inhalation valve 4250 has two different degrees of rotation. In particular, the valve 4252 itself rotates along the axis of the pin 4255 as the pin 4255 itself rotates when an appropriate force is applied to the valve 4252. The additional degree of rotation is that, in some embodiments, the valve 4252 can rotate physically relative to the pin 4255 itself. Thus, the combined pin 4255 and valve 4252 can rotate together and/or the valve 4252 can rotate independently relative to the pin 4255.

FIGS. 51 and 53 also show another feature of the present invention in that an MDI nozzle connector feature is incorporated into the port 4320. In particular, the port 4320 includes an opening 4390 formed in the side wall of the port 4320 and open to the exterior. Opening 4390 serves as an MDI port. Within the inside of the port 4320, there is a depending finger 4392 that extends inwardly into the port 4320. The finger 4392 has a central bore formed therein, with the opening 4390 defining an entrance into the central bore. At an opposite end of the bore, an MDI injection orifice 4394 is formed. As shown, an axis through the orifice 4394 is formed at an angle (e.g., 90 degree) relative to an axis through the central bore (and opening 4390). When the MDI is connected to the port 4320, the MDI nozzle partially enters into the central bore and the discharged medication flows through the bore and exits the orifice 4394 and flows directly to the patient (the orifice 4394 directly faces the patient and the finger 4392 is located behind the emergency inhalation valve assembly.

While FIGS. 46-53 show the use of a valve seat that has a flat valve seat surface, it will be appreciated that different valve seat constructions can be used such as the construction shown in FIGS. 86-87. For example, each of the exhalation valve assemblies and the secondary (emergency) inhalation valve assembly can use the valve seat construction illustrated in FIGS. 86-87. As shown in FIGS. 86-87, a valve seat 4395 is provided and includes hub 4396 and a valve retention knob (integral to the hub) 4397. The valve seat 4395 includes a valve seat surface 4398 that is a non-planar surface and in particular, as illustrated, the valve seat surface 4398 has a conical shape (but can have any of the shapes described above).

In contrast to a flat seat geometry, the valve seat surface can have a non-planar construction and more particularly and in accordance with the present invention, the valve seat construction can be a construction selected from the group consisting of: a conical valve seat (FIGS. 86-87); a conical valve seat, a concave valve seat and a parabolic valve seat. It will be understood that a flat valve can still be used with any of the above seat geometries. A flat valve tends to take the shape of the valve seat and by taking the shape of the seat the valve remains in a non-relaxed state causing internal stresses within the valve. The internal stresses within the valve tend to push the valve into the valve seat creating a more effective seal between the valve and the seat. The dimensional distance between the seat and the under-side of the valve retention knob 4397 forces the valve to take the shape of the seat.

Figure 54:
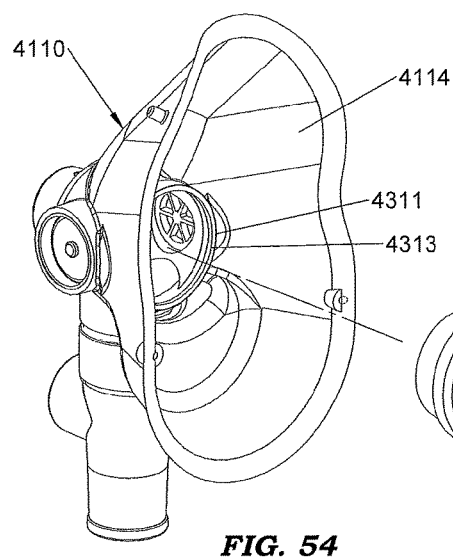
FIG. 54 is a rear perspective view of the patient interface system showing an HME assembly exploded therefrom.
Figure 55:
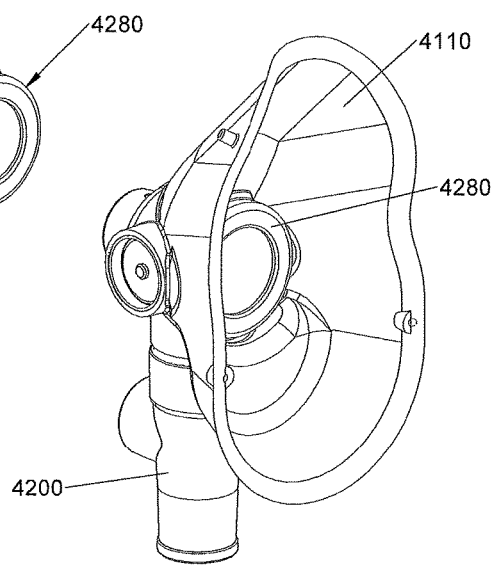
FIG. 55 is a rear perspective view of the patient interface system with the HME assembly installed therein.

Now turning to FIGS. 54-55 which are rear perspective views showing the hollow interior of the patient interface 4100. FIG. 54 shows the patient interface 4100 and an HME assembly 4280 that is shown exploded therefrom. As shown and as mentioned above, the mask valve assembly 4300 is a hollow structure and includes a rear opening 4311 that is defined by an annular shaped flange or lip 4313. FIG. 55 shows the HME assembly 4280 inserted and securely attached to the mask valve assembly 4300 (i.e., disposed within the rear opening 4311). The HME assembly 4280 is positioned within the mask so as to function as an HME exchange in that both inhaled air and exhaled air of the patient passes through the HME assembly 4280.

Figure 56:
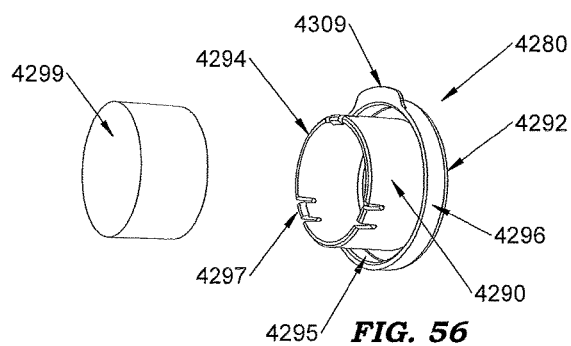
FIG. 56 is an exploded perspective view of the HME assembly.
Figure 57:
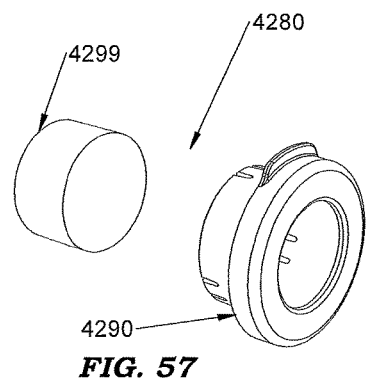
FIG. 57 is also an exploded perspective view of the HME assembly.

FIGS. 56-57 show the HME assembly 4280 in more detail. The HME assembly 4280 includes an HME housing 4290 that is a generally hollow structure with an open first end 4292 and an open second end 4294. The housing 4290 generally includes an annular wall 4295 that terminates at the second end 4294 and an annular sealing flange 4296 at the first end 4292. The annular flange 4296 has a greater diameter than the annular wall 4295 and thus protrudes outwardly therefrom. As a result, an annular shaped space is formed between the annular wall 4295 and the annular flange 4296.

The annular wall 4295 has integrally formed therewith one or more HME retention snaps 4297 that assist in retaining the HME media 4299 within the annular wall 4295 of the HME housing 4290. The HME assembly 4280 also includes HME media 4299 that is sized and configured to fit within the hollow space inside the annular wall 4295. Any number of techniques can be used to securely couple the HME media 4299 within the hollow space inside the annular wall 4295. For example, the HME media 4299 can be frictionally fit, bonded using adhesive or snapped into the hollow space inside the annular wall 4295. The HME media 4299 can be a traditional heat moisture exchange media (i.e., foam, wovens, pleated paperboard, etc.). The illustrated HME media 4299 has a solid cylindrical shape.

The annular sealing flange 4296 can include a tab 4309 that serves as finger hold for both insertion and removal of the HME assembly 4280 from the mask valve assembly. The tab 4309 extends outwardly from the annular flange 4296.

The HME assembly 4280 is intended to be securely attached to the body of the mask valve assembly 4310 by a mechanical fit, such as a frictional fit or snap-fit. For example, the lip 4313 of the body of the mask valve assembly can be received within the annular shaped space that is formed between the annular wall 4295 and the annular flange 4296. This is very much similar to how a lid of a plastic food container mates with the base in a sealing manner. When inserted into the rear opening 4311 of the body of the mask valve assembly, the HME assembly 4280 is securely contained and held in place within the interior of the face mask body in a location in which the open end 4292 faces the patient and thus, one end (face) of the HME media 4299 is exposed and faces the patient.

It will be appreciated that the HME assembly 4280 is thus designed to receive the inhaled breath and exhaled breath of the user (patient) and thereby serve as a heat moisture exchanger.

Figure 58:
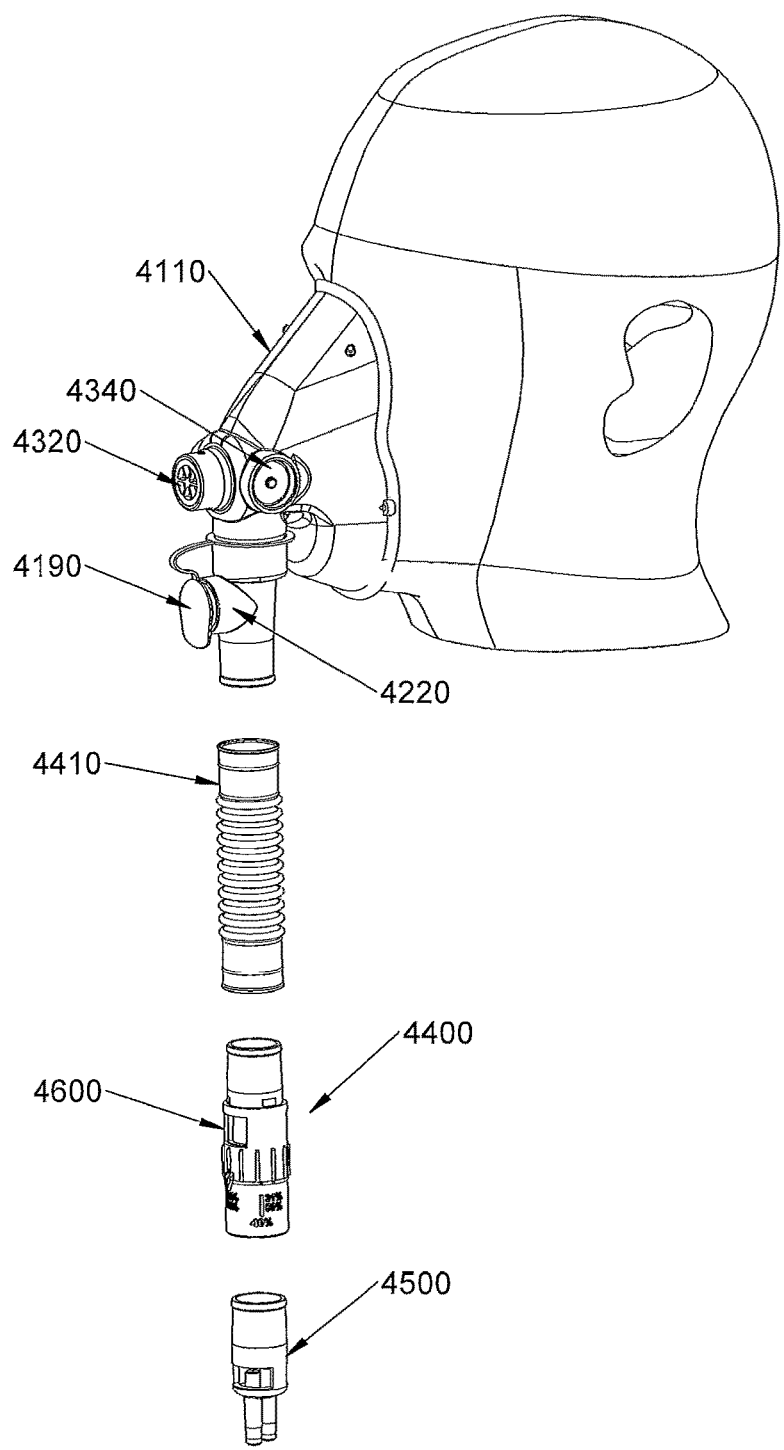
FIG. 58 is an exploded perspective view of a respiratory treatment system for low concentration gas (oxygen) delivery.

FIG. 58 shows one operating mode for the patient interface system (modular pulmonary treatment system) 4000 and in particular, the system of FIG. 58 is arranged for low concentration oxygen delivery with or without heat and moisture exchange dependent upon whether or not the HME assembly 4280 is placed within the patient interface 4000 as previously described. As shown, the secondary gas port 4220 is capped in this operating mode by means of a cap 4190 (that can be integrally attached to the body of the primary gas valve assembly as by a tether). In this operating mode, a venturi entrainment assembly 4400 is used. The assembly 4400 is formed of a number of parts (components) that interact with one another to provide for controlled gas delivery to a patient. The assembly 4400 is meant for use with a patient interface member (assembly) 4000 that is designed to interact with the patient and in one exemplary embodiment, the interface member 4000 is in the form of a mask assembly. It will be appreciated that the illustrated interface member 4000 is merely exemplary in nature and any number of other types of interface members can be used for delivery gas to the patient. The interface member 4000 includes the primary gas valve assembly 4200 for receiving the gas from the venturi assembly 4400. An elongated conduit member 4410 is connected to the primary gas valve assembly 4200 and to the venturi assembly 4400 for delivering the gas from the venturi assembly 4400 to the interface member 4000. The elongated conduit member 4410 can be in the form of an elongated tube which can be of a type which is expandable/retractable in that a length of the elongated conduit member 4410 can be varied. Conventional methods of attachment can be used to attach the elongated conduit member 4410 to both the interface member 4000 and the venturi assembly 4400.

FIGS. 59-70D illustrate in more detail the venturi assembly 4400 according to one embodiment of the present invention. The venturi assembly 4400 is formed of two main components, namely, a multi-port venturi member 4500 and a secondary gas entrainment valve member 4600. FIGS. 59-68 show the multi-port venturi member 4500 according to one embodiment. The multi-port venturi member 4500 has a first end 4502 and an opposite second end 4504. The multi-port venturi member 4500 is a generally hollow body 4501 that includes a main hollow space 4503 at the first end 4502. In the illustrated embodiment, the body 4501 has a cylindrical shape; however, it will be appreciated that the body 4501 can have any number of other shapes.

The body 4501 also has an air entrainment window 4560 formed therein below the main hollow space 4503. The air entrainment window 4560 is thus located intermediate to the ends 4502, 4504. The member 4500 also includes a lower body section 4562 that is connected to the hollow body 4501 by means of a pair of opposing walls 4565 (e.g., a pair of vertical walls located 180 degrees apart). The wall 4565 thus partially defines the air entrainment window 4560. The lower body section 4562 is a disk shaped structure that lies below the air entrainment window 4560 and serves as a floor of the air entrainment window 4560. The air entrainment window 4560 is thus open to atmosphere and serves to allow air to flow into the hollow space 4503 and then flow ultimately to the patient (by means of the elongated conduit member 4410 to the interface member 4000).

The member 4500 also includes at least one and preferably a plurality of gas port members 4570, 4580 that extend downwardly from the lower body section 4562. The gas port members 4570, 4580 are configured to be individually connected to a gas source (such as an oxygen gas source). As shown in the cross-sectional view of FIG. 62, the gas port members 4570, 4580 are elongated hollow conduits that each allows a fluid, such as gas, to enter at an exposed, free distal end 4572, 4582 and flow therethrough into the hollow space 4503 while flowing by the air entrainment window 4560 which is designed to allow atmospheric gas (air) to be entrained by the gas flow through the gas port orifices 4571, 4581. Entrainment of air through the window 4560 results due to the pressure drop created by the gas flowing through one of the gas port members 4570, 4580 and its respective orifice 4571 or 4581. The distal ends 4572, 4582 can be barbed ends to facilitate mating of the gas port members 4570, 4580 to conduits (tubing) that is connected to the same, single gas source or to different gas sources.

In another embodiment, the member 4500 includes only a single gas port member.

It will be understood that at any one operating time, gas is flowing through only one of the gas port members 4570, 4580. As described below, the gas port members 4570, 4580 have different gas flow characteristics and therefore, depending upon the desired gas concentration that is chosen to be delivered to the patent, the user selects one of the gas port members 4570, 4580 to use. Once again, at any one point in time, only one of the gas port members 4570, 4580 is active in that gas is flowing therethrough. Alternatively, both gas ports could be used simultaneously using two gas sources or via a single gas source using a wye-tubing.

As best shown in FIGS. 59-62, the gas port members 4570, 4580 are constructed so as to provide known gas flow rates. In particular, a top wall 4585 is formed across the tops of the gas port members 4570, 4580 and defines the ceiling of the gas port members 4570, 4580. An orifice (through hole) 4571, 4581 is formed in the top walls 4585 of the gas port members 4570, 4580, respectively. The shape and dimensions of the orifices 4571, 4581 define the gas flow characteristics base upon the flow and pressure of the gas provided by the gas source to either of the gas port members 4570, 4580. Hence the degree of pressure drops could be influenced to allow predictable air entrainment to ultimately influence the final oxygen concentration of the gas mixture.

As a result, the gas port member 4570 has different flow characteristics than the gas port member 4580. It will be appreciated that the system 4400 can include a plurality of multi-port venturi members 4500 that can be grouped as a kit. This allows the user to select the venturi member 4500 that has the desired, chosen gas flow characteristics. The venturi members 4500 can be interchanged as part of the overall system 4400 depending upon the precise application and desired gas concentration to be delivered to the patient.

As best shown in the cross-sectional view of FIG. 62, first lengths of the elongated gas port members 4570, 4580 are located above the lower body section 4562 and second lengths of the elongated gas port members 4570, 4580 are located below the lower body section 4562 (which is generally in the form of a disk that defines a floor of the member). The second lengths are greater than the first lengths and therefore, more of the gas port members 4570, 4580 are located below the lower body section 4562. The lower body section 4562 defines a solid wall structure between the gas port members 4570, 4580. The tops of the gas port members 4570, 4580 are disposed within the air entrainment window. In other words, the height of the gas port members 4570, 4580 is such that the tops are disposed within the air entrainment window and therefore, gas exiting the top of one of the gas port members 4570, 4580 is mixed with entrained air flowing into the air entrainment window 4560.

The gas flow rates associated with the gas port members 4570, 4580 can be the same or the flow rates can be different. FIGS. 60-61 illustrate a laterally disposed gas injection arrangement in which the gas port members 4570, 4580 are located adjacent the vertical walls 4565 as best shown in FIG. 60 and the orifices 4571, 4581 are centrally located with respect to the center bore of the gas port members 4570, 4580. The orifice 4571 has a greater size than the orifice 4581 and therefore, different flow characteristics. It will be appreciated that the orifices 4571, 4581 thus serve to meter the gas from the gas source as it flows through the gas port members 4570, 4580 into the hollow space 4503.

As will be appreciated by the following discussion, the arrangement in FIG. 58 serves as a low concentration gas (oxygen) delivery system. The dual nature of the air entrainment windows provides for a reduced or lower concentration of gas being delivered to the patient. As described herein, the user can control the concentration of the gas (oxygen) being delivered to the patient by selecting the desired gas port member 4570, 4580 and by manipulating the shutter 4650 to thereby change the degree the air entrainment window is open (or whether it is closed).

During inhalation, the primary inhalation valve 4250 (which is located within the hollow body of the primary gas valve assembly 4220 opens in such a way, at least in one embodiment, that it gets significantly out of the way of the flow passage of the gas and/or aerosolized medication flow through the member 4200. This can be achieved by constructing the valve body 4252 as a flapper valve, umbrella valve, or swing valve and the valve body 4252 can be of a rigid construction or of a flexible construction.

It will be appreciated that the emergency inhalation valve member 4324 does not open during normal inhalation activity as a result of the construction and design differences between the primary and emergency inhalation valves 4250, 4324. In particular, the two valves 4250, 4324 can be specifically designed to generate differential resistance and differential opening in response to an applied inspiratory flow or pressure. In other words, the two different valves are constructed such that the emergency valve 4324 only opens when an elevated force is applied thereto as compared to the primary valve 4250 which opens when normal inhalation forces are applied. As a result, when normal inhalation forces (pressures) are applied to both during patient inhalation, the primary valve 4250 only will open since the opening pressure requirement of the primary valve is reached; however, the normal inhalation forces (pressures) are not sufficient to open the emergency valve 4324. As a result, the emergency valve 4324 requires more applied force (pressure) to open and only in an emergency are such elevated applied forces (pressures) achieved especially when the gas flow through the primary inhalation valve may not be sufficient to meet patient's gas flow requirement.

Once the primary valve 4250 opens, the gas (oxygen) can flow directly into the inside of the mask to the patient. When the patient exhales, the primary valve 4250 closes and one or both of the exhalation valves 4332, 4334 open to release the exhaled air.

As will be appreciated by FIGS. 54-57, the HME assembly 4280 can be used as part of this gas delivery operating mode. When the HME assembly 4280 is installed, the HME media 4299 is positioned between the patient and each of the patient interface system 4000 valves and valves of the primary gas valve assembly system 4200 that form a part of the overall system.

Thus, it will be appreciated that the HME assembly 4280 is so positioned within the patient interface 4100 that inhaled emergency air passes first through the emergency valve 4324 before coming into contact with the HME media 4299 and passing therethrough to the patient. Even in the unlikely event that the emergency inhalation valve 4324 opens and air flows therethrough, such air flows also through the HME media 4299 before reaching the patient. Similarly, exhaled air passes through the HME media 4299 before then exiting through one or both of the exhalation valves 4332, 4334.

The HME assembly 4280 is thus positioned strategically within the mask such that both inhaled and exhaled air pass therethrough and at the same time, the modular nature (cartridge nature) of the HME assembly 4280 permits the user to easily implement the HME functionality.

The HME assembly 4280 can easily be inserted and removed from the patient interface 4000 due the unique manner in which it seats within the interface 4000 and therefore, the user can easily convert the face interface 4000 between both an HME operating mode and a non-HME operating mode.

The present invention also provides for user adjustment in real-time to alter the concentration of the gas being delivered to the patient since the shutter (4650, FIG. 69) can be readily adjusted.

In the embodiment of FIGS. 60-61, the gas port members 4570, 4580 are thus not located directly within the air entrainment window due to the members 4570, 4580 being disposed adjacent the vertical walls 4565.

FIGS. 63-64 show a different embodiment and in particular, show laterally disposed eccentric gas injection. As with FIGS. 63-64, the gas port members 4570, 4580 are disposed laterally in that these members are formed adjacent the vertical walls 4565; however, in this embodiment, the orifices 4571, 4581 are not located centrally within the gas port members 4570, 4580, respectively. Instead, the orifices 4571, 4581 are eccentrically formed within the gas port members 4570, 4580.

FIGS. 65-66 show a different embodiment and in particular, show centrally disposed gas injection. Opposite to the arrangement shown in FIGS. 60-61, the gas port members 4570, 4580 in FIGS. 65-66 are disposed centrally in that the gas port members 4570, 4580 are not located adjacent the pair of vertical walls 4565 as best shown in FIG. 65. Instead, the gas port members 4570, 4580 are located spaced (offset) from the vertical walls 4565 and are disposed directly within the air entrainment window 4560. The orifices 4571, 4581 are located centrally within the gas port members 4570, 4580, respectively.

FIGS. 67-68 show a different embodiment and in particular, show centrally disposed eccentric gas injection. Opposite to the arrangement shown in FIGS. 63-64, the gas port members 4570, 4580 in FIGS. 67-68 are disposed centrally in that the gas port members 4570, 4580 are not located adjacent the pair of vertical walls 4565 as best shown in FIG. 67. Instead, the gas port members 4570, 4580 are located spaced (offset) from the vertical walls 4565 and are disposed directly within the air entrainment window 4560. Unlike the centrally disposed gas injection of FIGS. 65 and 66, the orifices 4571, 4581 in FIGS. 67 and 68 are eccentrically formed within the gas port members 4570, 4580.

It will be appreciated that the relative sizes of the orifices 4571, 4581 are merely exemplary in nature and the sizes of orifices 4571, 4581 can be readily changed. For instance, the orifice 4581 can be larger in size than orifice 4571.

In one exemplary embodiment, the end 4502 of body 4501 has a outside diameter of about 22 mm.

FIG. 69 shows the secondary gas entrainment valve member 4600 which is formed of a generally hollow body 4610 that has a first end 4612 and an opposing second end 4614. As shown in FIG. 58, the second end 4614 is configured to mate with the first end 4502 of the multi-port venturi member 4500. The second end 4614 can be a female connector type, while the first end 4502 of the multi-port venturi member 4500 is of a male connector type. Similarly, the first end 4612 can be a male connector type that is designed to mate with the elongated conduit member 4410.

The generally hollow body 4610 has a secondary air entrainment window 4620 formed integrally therein. The air entrainment window 4620 extends circumferentially about the body 4610 and thus is defined by a first end (in the form of a vertical edge) and a second end (in the form of a vertical edge). The air entrainment window 4620 is intended to allow atmospheric gas (air) to flow into the hollow interior of the body 4610 where in mixes with the gas that flows out of the multi-port venturi member 4500 (which one will appreciate is already mixed gas due to air being entrained through the air entrainment window 4560 (which can be thought of as being a main or primary air entrainment window). The air entrainment window 4620 is a secondary window since it serves as a second window between the gas source and the patient interface 4000 in which air can be entrained through to mix with the gas for purposes of altering the characteristics, and in particular, the gas concentration, of the gas that is delivered to the patient.

In accordance with the present invention, the secondary gas entrainment valve member 4600 includes a rotatable shutter 4650 that is cylidrically and vertically coupled to the body 4610 and more specifically, the shutter 4650 is disposed about the body 4610 in the location of the air entrainment window 4620 to allow the shutter 4650 to either open or close the secondary gas entrainment window 4620 depending upon the desired setting as described below. The shutter 4650 has a first (top) end 4652 and an opposite second (bottom) end 4654.

Any number of different techniques for coupling the shutter 4650 to the body 4610 can be used. For example, different types of mechanical attachment techniques can be used including a friction fit, a snap fit, etc. In FIG. 69, the body 4610 includes a shutter retaining mechanism in the form of tabs 4665 spaced apart from one another and located circumferentially about the body 4610. The top end 4652 of the shutter 4650 is located below the tabs 4665.

The shutter 4650 itself has an air entrainment window 4660 formed therein. The air entrainment window 4660 is defined by a first end 4662 (vertical wall) and a second end 4664 (vertical wall).

There is a rotational correlation between the degree of registration between the air entrainments windows 4620, 4660 and more particularly, the degree of overlap and openness of the two windows 4620, 4660 factors into the amount of air being entrained through the secondary gas entrainment valve member 4600 and thus, the concentration of the gas delivered to the patient.

The shutter 4650 rotates about the body 4610 as mentioned above and therefore, the shutter 4650 can include features 4655 as a means to assist the user in rotating the shutter 4650. In particular, the features 4655 can be in the form of ribs that are spaced apart and extend circumferentially about the shutter 4650. The ribs 4655 are raised structures that permit the user to more easily grip and rotate the shutter 4650 relative to the body 4610.

The secondary gas entrainment valve member 4600 also preferably includes indicia to allow the user to set the degree of air entrainment and thus, to position the secondary gas entrainment valve member 4600 at a setting that achieves the desired gas concentration being delivered to the patient.

For example, the shutter 4650 can include a gas concentration pointer 4665 that is formed along the bottom edge 4654 of the shutter 4650 and the lower region of the body 4610 includes gas concentration indicator markings 4670. For example, the markings 4670 include a plurality of gas concentrations (in percentages) that correspond to the concentration of the gas that is delivered to the patient. The markings 4670 directly correspond to the degree of overlap between the windows 4620, 4660 in that the greater the overlap (registration) between the windows 4620, 4660, the greater the openness of the secondary air entrainment window resulting in a greater flow of atmospheric air into the member 4600 (thereby resulting in a reduced gas concentration being delivered to the patient as a result of more mixing between atmospheric gas and the mixed gas from the multi-port venturi member 4650).

The rotatability of the shutter 4650 allows the user to effectively and easily "dial in" the desired gas concentration for delivery to the patient by simply rotating the shutter 4650 to cause the pointer 4665 to point to the desired, selected gas concentration indicator marking 4670 (which has the desired gas concentration indicia listed). This results in the window being open the proper desired amount to achieve the target mixing, etc.

FIGS. 70A-70D shows the various operating states of the secondary gas entrainment valve member 4600.

FIG. 70A shows the air entrainment port in a fully opened position (i.e., complete registration between the windows 4620, 4660). As will be seen in FIG. 70A, the markings 4670 include two numbers, namely, a first number that is disposed on top of a second number. These two numbers correspond to the gas concentrations (%) that are obtained depending upon which of the venturi gas port members 4570, 4580 is used. In the example shown in FIG. 70A, the second number (35%) corresponds to the gas port member 4570 (which has a larger orifice 4571 compared to the orifice 4581 of gas port member 4580). The first number (24%) corresponds to the gas concentration obtained with gas port member 4580.

FIG. 70D shows the air entrainment port in a fully closed position (i.e., complete non-registration between the windows 4620, 4660). As will be seen in FIG. 70D, the markings 4670 include two numbers, namely, a first number that is disposed on top of a second number. These two numbers correspond to the gas concentrations (%) that are obtained depending upon which of the gas port members 4570, 4580 is used. In the example shown in FIG. 70D, the second number (50%) corresponds to the gas port member 4570 (which has an larger orifice 4571 compared to the orifice 4581 of gas port member 4580). The first number (31%) corresponds to the gas concentration obtained with gas port member 4580.

FIGS. 70B and 70C show the air entrainment window in partially open positions in which the window 4660 formed in the shutter 4650 is not in complete registration with the window 4620 formed in the body 4610. It will be appreciated that FIG. 70B is a partially open window.

It will be appreciated that the openness of the air entrainment window is very similar in FIG. 70B and in FIG. 70C; however, the two different resulting gas concentrations (e.g., 28% vs. 40%) is based on whether the gas port member 4570 or gas port member 4580 is used. When the larger sized gas port member 4570 is used, the 40% is obtained when the window is in the position of FIG. 70C. Conversely, when the smaller sized gas port member 4580 is used, a gas concentration of 28% is obtained when the air entrainment window is placed in the partially open position of FIG. 70B. It is to be appreciated that the openness of the entrainment windows in 70B and 70 C may be different and varied to achieve different concentrations of oxygen delivery based on whether the gas port member 4570 or gas port member 4580 is used.

It will be appreciated that other partially open positions can be used with the present system.

It will also be understood that the gas entrainment valve member 4600 can be used with other venturi members besides the multi-port venturi member 4500 that is shown paired with the member 4600 in assembly 4400. For example, the venturi connector assemblies of FIGS. 25A and B, 28-29, 30A and B and 34A and B, 35A and B, and FIGS. 36A and B can be used with the gas entrainment valve member 4600. In particular and similar to the system of FIG. 58, the combination of any of the above mentioned venturi connector assemblies and with the gas entrainment valve member 4600 provides two different air entrainment windows that are spaced apart from one another. More specifically, the combination provides two air entrainment windows that are located in series between the gas source and the patient interface (mask) 4000. It will also be appreciated that the gas entrainment valve member 4600 can be used with any traditional venturi (venturi connector) to provide a dual air entrainment window structure.

Unlike conventional venturi design, the present invention teaches the use of two connector members that provide the dual window design (dual air entrainment windows) with one air entrainment window being located serially downstream from the other window and at least one window is adjustable in nature in that the degree of which the window is open can be adjusted by the user.

It will be appreciated that the elongated conduit 4410 can vary in its diameter and/or length and the size and length of the elongate conduit 4410 dictates the reservoir capacity and provides a means of reducing the noise level of the gas delivery mechanism experienced by the patient.

Figure 71:
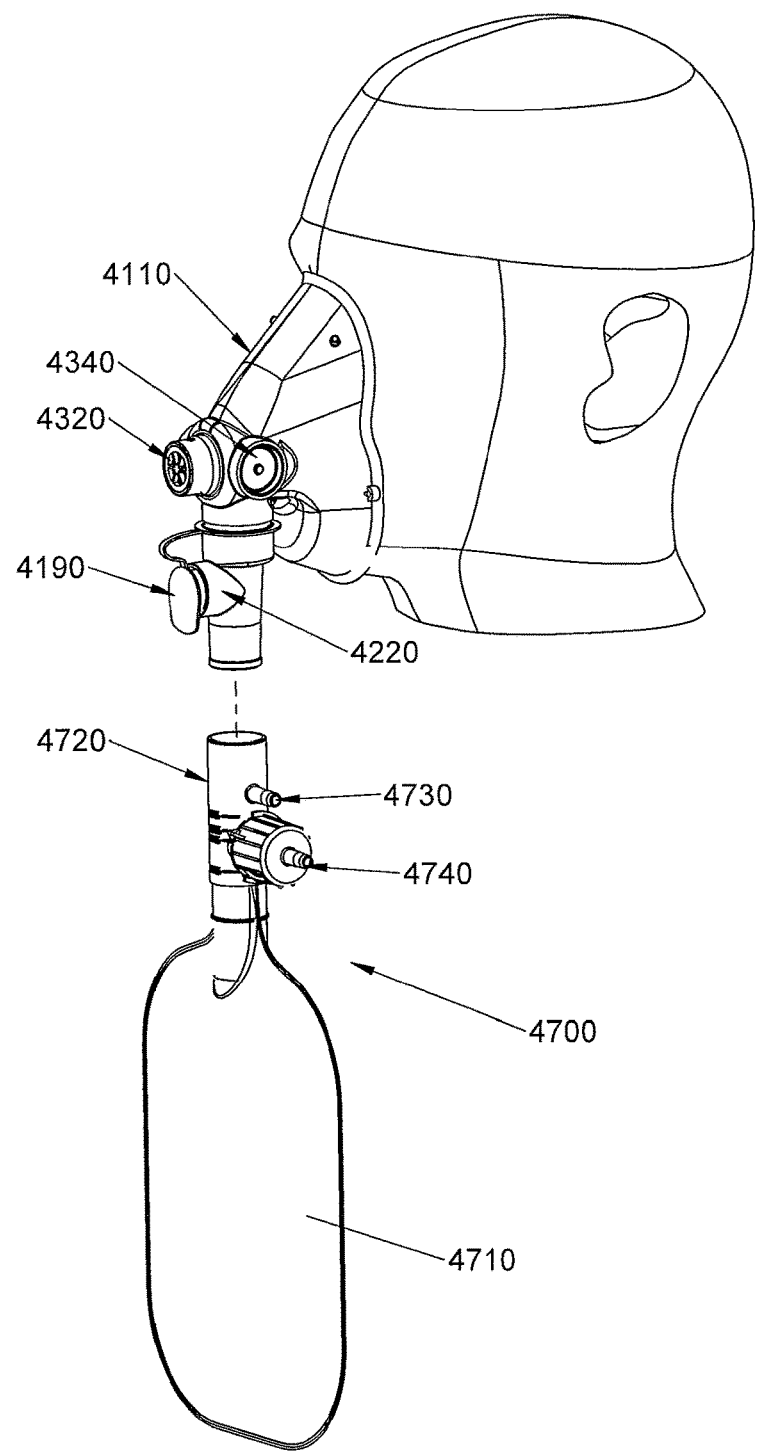
FIG. 71 is an exploded perspective view of a respiratory treatment system for high concentration gas (oxygen) delivery.

FIG. 71 illustrates one operating mode of the system in accordance with the present invention and in particular, utilizes the patient interface (mask) 4000. The operating mode shown in FIG. 71 can be characterized as being a high concentration oxygen delivery operating mode. In this operating mode, the second (distal) end 4214 of the primary gas valve assembly 4200 is attached to a high concentration gas delivery assembly 4700. The assembly 4700 includes a reservoir member 4710 which can be in the form of an inflatable bag that has an opening 4712 at one end.

The assembly 4700 also includes a high concentration gas valve connector 4720 which is configured to mate with and seal to the bag opening 4712. As best shown in FIGS. 72-76, the connector 4720 is formed of a valve body 4722 that has a first end 4724 and an opposing second end 4726. The valve body 4722 is an elongated hollow structure to allow fluid (gas) to readily flow therethrough. The valve body 4722 includes a retaining ring 4725 that assists in coupling the reservoir member 4710 to the valve body 4722. However, it will be appreciated that other retaining mechanisms can be used.

As shown, the valve body 4722 includes a first gas port 4730 and a second gas port 4740, each of which is disposed along one side of the body 4722. The first gas port 4730 is located closer to the first end 4724 and can be in the form of a barbed gas port that is attached to a conduit (e.g., tube) that is attached to a gas source (e.g., oxygen). The second gas port 4740 is located below the first gas port 4730 and includes a main port body 4750 that is integrally formed with the body 4722. The main port body 4750 is a hollow structure (tubular) that has an open end 4751 and includes along its outer surface a detent ring 4752. The main port body 4750 also includes an air entrainment window 4755 that is formed therein circumferentially about the main port body 4750.

The second gas port 4740 is of an adjustable type in that it includes a rotating shutter 4760 that is cylindrically and horizontally coupled to the main port body 4750. As shown, the rotating shutter 4760 can be in the form of cap-like structure that is received on the open end of the main port body 4750. The shutter 4760 has an open end (which receives the main port body 4750) and an opposite closed end. The shutter 4760 has a main section that has an air entrainment window 4762 formed therein. The air entrainment window 4762 extends circumferentially about a portion of the body 4750. The air entrainment window 4762 is formed at a location on the shutter 4760 such that it overlaps (is in registration) with the window 4755 of the main port body 4750 and preferably, the dimensions of the window 4762 are greater than the dimensions of the window 4755.

Figures 72, 73, 74, 75, 76:
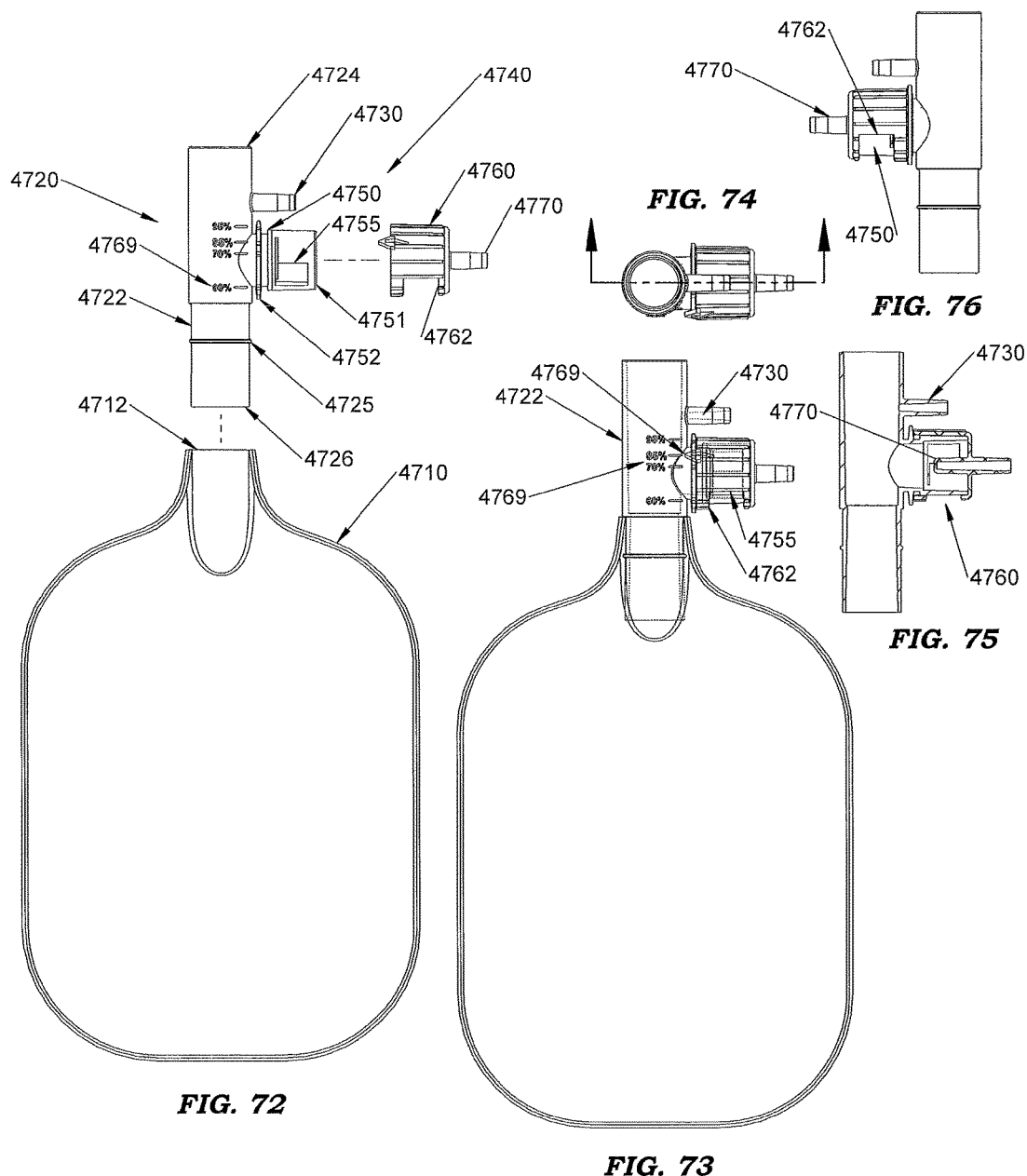
FIG. 72 is an exploded elevation view of a device of the system of FIG. 71.
FIG. 73 is an elevation view of the device of FIG. 72 in an assembled condition.
FIG. 74 is a top plan view of the device of FIG. 73.
FIG. 75 is a cross-sectional view taken along the line 75-75 of FIG. 74.
FIG. 76 is a rear elevation view thereof.

The rotating shutter 4760 also includes a (barbed) gas port member 4770 that extends radially outward from the closed end of the shutter 4760 and also is formed internally within the shutter 4760 as shown in FIG. 75. The internal section of the member 4770 serves as a gas injection orifice that directs the gas into the hollow interior of the body 4722. The open end of the internal section of the member 4770 is located preferably in-line with the windows 4755, 4762 since the internal section is physically received within the hollow interior of the main port body 4750. Orifice 4770 could be of variable size (diameter) to allow variable gas flow and pressure drop for air entrainment from window 4762. Multiple venturi arrangement can be made like FIGS. 25A and B, 28-29, 30A and B and 34A and B, 35A and B, and FIGS. 36A and B.

Similar or identical to the shutter 4650, the shutter 4760 also includes a gas concentration pointer 4767 that extends outwardly from (and beyond) the open end of the shutter 4760. The valve body 4722 includes gas concentration indicator markings 4769 that are formed thereon. For example, the markings 4769 can be vertically displayed along the connector body 4722. As the user rotates the shutter 4760, the degree of registration between the windows 4755, 4762 changes (between a fully open position and a fully closed position, as well as intermediate, partially open states). To change the concentration of the gas being delivered through the second gas port 4750, the user simply adjusts the shutter 4760 and thereby changes the amount of air entrainment that occurs. In the fully open position of the shutter, more air is entrained with the gas flow and therefore, the concentration of the gas (e.g., oxygen) that is delivered to the patient is lower. FIG. 76 shows the air entrainment window partially open.

One will appreciate that by having two different gas port entry points, different concentration of gas can be achieved and then delivered to the patient. For example, the first gas port 4730 is unmetered and therefore produces a fixed flow rate of the gas (gas concentration) that flows therethrough into the main body. However, as discussed above, the second part port 4740 is metered and produces a variable gas concentration since an amount of air is entrained with the gas that flows through the port member 4770. Much like the shutter 4650 described hereinbefore, the shutter 4760 can be rotated to adjust the degree of air entrainment and thereby, directly alter the mixed gas that is delivered into the main port body to the patient. It is expected that in most applications, both the first and second gas ports 4730, 4740 are attached to the gas source and are both actively receiving the gas at the same time. In the event that the shutter 4760 is closed, the concentration of the gas flowing through the first and second gas ports 4730, 4740 is the same. However, in one embodiment, at least one of the first gas port 4730 and the second gas port 4740 can be sealingly closed, as by a cap, thereby leaving one active gas port.

As shown in FIG. 71, the first and second gas ports 4730, 4740 are located below the primary inhalation valve 4250 (that is part of the patient interface 4000); however, there is free, unobstructed flow between the first and second gas ports 4730, 4740 and the interior of the reservoir member 4710. Thus, when the primary inhalation valve 4250 is closed, any gas flowing through the first and second ports 4730, 4740 flows directly into the interior of the reservoir member 4710. The bag 4710 can expand as it fills up.

When the patient inhales, the primary inhalation valve 4250 opens as discussed herein before and gas can flow directly from the first and second gas ports 4730, 4740 and also any gas stored in the reservoir bag 4710 can flow to the patient through the primary inhalation valve 4250.

Now turning to FIG. 77 which shows another operating state of the system 4000 in accordance with the present invention. The embodiment shown in FIG. 77 can be thought of as a 100% non-rebreather gas (oxygen) delivery system. In this embodiment, the reservoir member 4710 is connected to a connector 4800 that is a hollow (tubular) structure that includes a single gas port 4810 extending outwardly therefrom. This gas port 4810 is intended for connection to a gas source, such as oxygen.

Since gas is delivered through the gas port 4810 by means of the gas port 4810, the concentration of the gas is fixed and there is no air entrainment (venturi) in this embodiment (thus, the concentration of the gas is not diluted with air). When the primary inhalation valve 4250 is closed, the gas flows through the gas port 4810 into the reservoir member 4710 for storage therein. When the primary inhalation valve 4250 opens, the gas flowing through the gas port 4810 and the gas stored in the reservoir member 4710 can flow to the patient interface 4000.

Now turning to FIG. 78 which shows another operating mode of the system 4000 of the present invention and in particular, shows a standard dose aerosol drug delivery system. In this embodiment, the secondary port 4220 is not capped with a cap or plug 4190 and a nebulizer device 4900 is sealingly fitted to the open second (distal) end of the primary gas valve assembly 4200. The nebulizer device 4900 is thus located below the primary gas valve 4250. The aerosolized medication from the nebulizer device 4900 is thus delivered into the hollow space of the assembly 4200 and upon opening of the primary gas valve 4250, the aerosolized medication flows directly into the interior of the face mask 4110 to the patient.

Since the secondary gas port 4220 remains open and is located below the primary gas valve 4250, the aerosolized medication is free to flow out of the secondary gas port 4220 when the primary gas valve 4250 is closed as during exhalation. The secondary gas port 4220 thus serves as exit or outlet for the aerosolized medication during exhalation and as a supplemental gas source in addition to the aerosolized medication delivered by the nebulizer 4900 during inhalation.

Figures 79, 80:
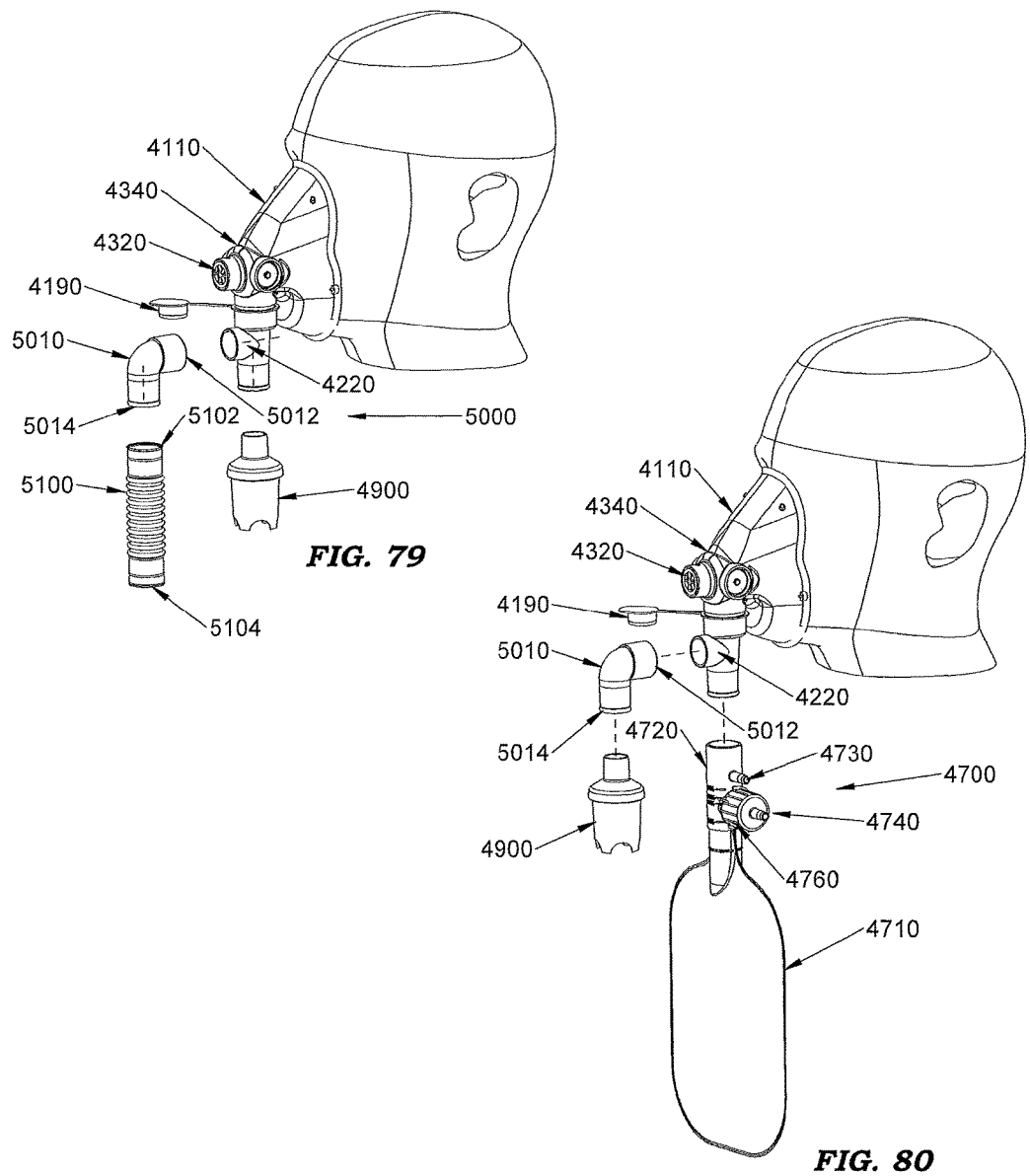
FIG. 79 is an exploded perspective view of a respiratory treatment system for enhanced dose aerosol drug delivery.
FIG. 80 is an exploded perspective view of a respiratory treatment system for high dose aerosol drug delivery with gas delivery with single bag reservoir system.

FIG. 79 shows a different operating mode of the system 4000 of the present invention and in particular, this operating mode is an enhanced dose aerosol drug delivery mode. As with the standard dose aerosol drug deliver mode of FIG. 78, the operating mode of FIG. 79 includes the nebulizer 4900 attached to the distal end of the primary gas valve assembly 4200. Instead of the secondary gas port 4220 being used as a vent or supplemental gas source, a reservoir assembly 5000 is attached to the secondary gas port 4220 for storing the aerosolized mediation when the primary gas valve 4250 is closed.

In the illustrated embodiment, the reservoir assembly 5000 comprises several components that mate together to provide a reservoir for storing the aerosolized medication. For example, the illustrated assembly 5000 includes a connector 5010 that sealingly mates with the secondary gas port 4220. As shown, the connector 5010 can be in the form of a 90 degree elbow connector that attaches at a first end 5012 to the secondary gas port 4220 and has an opposite second end 5014. The assembly 5000 also includes a reservoir member 5100 which, as illustrated, is in the form of an elongated reservoir tube that has a first end 5102 and an opposite second end 5104. The first end 5102 is sealingly attached to the second end 5014 of the connector 5010.

It will be appreciated that the reservoir tube 5100 can be a corrugated tube and can have an adjustable length. In addition, the diameter of the tube 5100 can vary. It will be appreciated that by changing one or both of the length and diameter of the tube 5100, the storage capacity of the reservoir changes.

The secondary gas port 4220 is located below the primary gas valve 4250 and the aerosolized drug is introduced into the assembly 4200 at a location below the primary gas valve 4250 and therefore, when the primary gas valve 4250 is closed, the aerosolized mediation flows directly into the reservoir assembly 5000 and more particularly, the aerosolized medication can flow through the secondary gas port 4220 through the connector 5010 and into the reservoir tube 5100. The aerosolized medication thus resides within the tube 5100 and is stored therein.

The enhancement in the drug delivery of the aerosolized drug (medication) results as a result of the secondary gas port 4220 not being simply open to atmosphere as in the embodiment of FIG. 78 but instead is configured to a reservoir member in the form of the tube 5100 in which aerosolized medication is contained (stored) therein.

Now referring to FIG. 80 in which yet another operating mode of the system 4000 is shown and in particular, the illustrated operating mode is a high dose aerosol drug delivery operating mode. In this embodiment, the patient interface (mask) 4000 is connected to components previously described herein and therefore, like numbers are used in the figures to identify the same components. More specific, the elbow connector 5010 is sealingly attached to the secondary gas port 4220; however, instead of the connecting the nebulizer device 4900 to the open end of the primary gas valve assembly 4200, the nebulizer device 4900 is attached to the end 5014 of the elbow connector 5010.

Similar to the operating mode shown in FIG. 71, the operating mode of FIG. 80 includes the use of the high concentration gas delivery assembly 4700, which is connected to the second (distal) end of the primary gas valve assembly 4200. The reservoir member 4710 is in the form of an inflatable bag. The gas delivery assembly 4700 includes the first gas port 4730 and the second gas port 4740 and as previously discussed, this permits one of these ports to be connected to a gas (e.g., oxygen or heliox, etc.) that is for delivery to the patient. As discussed with reference to FIG. 71, a wye tube can be used to connect the two ports 4730, 4740 to a single gas source or separate tubes (conduits) can be used to connect the two ports 4730, 4740 to two different gas sources. As mentioned herein, during normal operating conditions both the first and second gas ports 4730, 4740 are attached to the gas source and are both actively receiving the gas at the same time. When a wye tube is used, it will be appreciated that the two distal legs of the wye tube can have the same or different diameters. By controlling the diameters of the distal legs, different gas flow rates can be achieved in the distal legs and thus, different gas flow rates are provided to the nebulizer and one of the gas ports 4730, 4740. Though two separate gas sources could be used, the system of delivery is intended to be used in conjunction with a wye tube, as previously discussed, with the exception that in this case one leg of the wye tube provides gas to the nebulizer 4900 and the other leg of the wye is connected to either one of gas ports 4730 or 4740 to control the oxygen concentration of the gas delivered to the patient. The other port that is not connected to the tubing may remain open or can be capped/plugged using a tethered cap or plug. One could in an alternative mode of delivery simultaneously choose two sources of gas and connect one gas source to the nebulizer and one gas with a wye-tubing to both the ports at the same time during medication delivery to adjust medication delivery and oxygen concentration at the same time.

The shutter 4760 can be rotated to adjust the degree of air entrainment and thereby, directly alter the mixed gas that is delivered into the main port body to the patient. The first and second gas ports 4730, 4740 are located below the primary inhalation valve 4250 (that is part of the patient interface 4000); however, there is free, unobstructed flow between the first and second gas ports 4730, 4740 and the interior of the reservoir member 4710. Thus, when the primary inhalation valve 4250 is closed, any gas flowing through the first or second ports 4730, 4740 flows directly into the interior of the reservoir member 4710. The bag 4710 can expand as it fills up.

When the patient inhales, the primary inhalation valve 4250 opens as discussed hereinbefore and gas can flow directly from either the first or second gas port 4730, 4740 and also any gas stored in the reservoir bag 4710 can flow to the patient through the primary inhalation valve 4250.

It will also be appreciated that the reservoir member (bag) 4710 stores aerosolized medication from the nebulizer device 4900 as a result of its positioning and based on the fact that there is a free, unobstructed flow path from the nebulizer device 4900 to the inside of the reservoir bag 4710. In particular, since the nebulizer device 4900 is connected to the secondary gas port 4220, which is below the primary inhalation valve 4250, the aerosolized medication from the nebulizer device 4900 can freely flow into the assembly 4200 (at a location below the primary inhalation valve 4250) and then through the connector 4720 and into the inside of the bag 4710 when the primary inhalation valve 4250 is closed (i.e., as during exhalation of the patient).

Conversely, when the patient inhales, the primary inhalation valve 4250 opens and the aerosolized medication (drug) can flow directly from the nebulizer device 4900 through the assembly 4200 to the patient. In addition, the connector 4720 is fluidly connected to the assembly 4200 and thus, the gas delivered through either of the ports 4730, 4740 is delivered through the open primary inhalation valve 4250 to the patient. There are thus two gas flow paths to the patient when the patient inhales. During exhalation, the reservoir bag 4710 stores both the gas delivered through either port 4730 and/or 4740, and/or the aerosolized medication delivered from the nebulizer device 4900 through the connector 5010.

The embodiment of FIG. 80 thus provides a high dose aerosol drug delivery system.

Figures 81, 82:
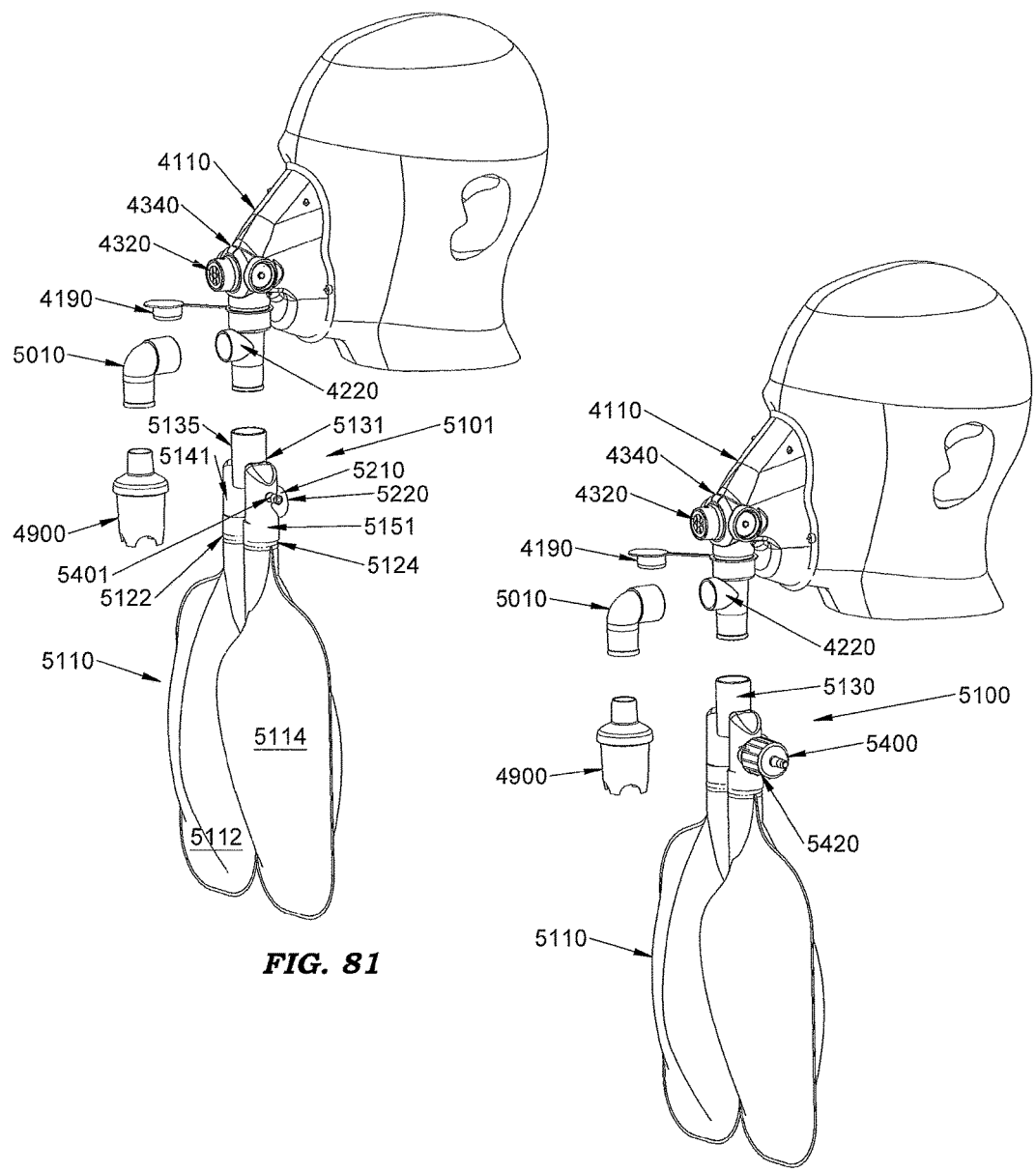
FIG. 81 is an exploded perspective view of a respiratory treatment system for high dose aerosol drug delivery with gas delivery with dual bag reservoir system.
FIG. 82 is an exploded perspective view of a respiratory treatment system for high dose aerosol drug delivery with controlled concentration gas delivery with dual reservoir bag system.

FIG. 81 illustrates another operating mode for the system 4000 and in particular, this operating mode is a high dose aerosol drug delivery with gas delivery operating mode. This operating mode is similar to the operating mode of FIG. 80 with the exception that the high concentration gas delivery assembly 4700 is replaced with a high dose aerosol drug/gas delivery mechanism 5100 which is shown in more detail in FIGS. 83-85.

The high dose aerosol drug/gas delivery mechanism 5100 is a dual reservoir system that is formed of a dual reservoir member (bag) 5110 that has two different (separate) interior compartments for storage of a fluid (gas). In the illustrated embodiment, the dual reservoir member 5110 is in the form of a bifurcated bag that has a first chamber (compartment) 5112 and a second chamber (compartment) 5114. The bag 5110 includes a neck portion that includes a first opening 5115 and a second opening 5117 (side by side relationship). Note that the dual bag reservoir system for dose drug delivery and high concentration oxygen delivery has been described earlier in FIGS. 37 and 43

The mechanism 5100 includes connectors 5120 that are constructed to mate with the two openings 5115, 5117 of the reservoir bag 5110. Each connector 5120 has a retaining member 5125, such as a retaining ring, which serves to attach the connector 5120 to the bag 5110. The conduit members 5122, 5124 of connectors 5120 define fluid flow paths allowing gas to flow into and out of the bag 5110.

The mechanism 5100 also includes a high dose valve body 5130 that includes a first end 5132 and an opposing second end 5134. The first end 5132 is a single conduit member 5135 in that it defines a single flow path, while the second end 5134 has a dual conduit structure in that the second end 5134 includes two side-by-side conduit members 5140, 5150 as best shown in the cross-sectional view of FIG. 85. The conduit members 5140, 5150 resemble legs. The conduit members 5135, 5140, 5150 are all in fluid communication with one another; however, as discussed below, the conduit member 5140 has a selective fluid communication due to the presence of a valve therein. The second end 5134 can thus generally have a U-shape as shown. The first end 5132 can be in the form of a 22 mm female connector.

The valve body 5130 also includes an over-inflation valve assembly 5200. More specifically, the valve body 5130 has a side port 5210 formed therein which is formed in the conduit member (leg) 5140. The valve assembly 5200 is disposed within the side port 5210 and more particularly, the valve assembly 5200 includes a valve seat 5220 that is disposed within the side port 5210 and is securely attached to the valve body 5130. The valve seat 5220 can be a spoke-like structure with a plurality of openings formed between the spokes and also includes a valve mounting post 5222 extending outwardly therefrom. An over-inflation valve 5230 is mated to the post 5222 (by reception of the post 5222 within an opening) and lies over the valve seat 5220.

In accordance with the present invention, a valve retention thimble 5240 is provided and is received over the post 5222. The valve retention thimble 5240 is constructed and intended to control valve movement. The thimble 5240 is adjustable on the post 5222 and thereby can control the maximum valve movement distance. In other words, the thimble 5240 can be set at a specific distance from the valve seat 5220 and thus from the valve 5230 itself since the thickness of the valve 5230 is known. For a given valve 5230, the greater the distance from the thimble 5240 to the valve seat and the valve, then the greater the degree of permitted movement for the valve 5230, thereby allowing a greater degree of opening for the valve 5230. In one embodiment, the thimble 5240 is adjusted until it is at a desired location along the post and is then set at the site of the manufacturer. Any number of techniques can be used to set it in place including using an adhesive. The use of an adjustable thimble 5240 allows the manufacturer to select and set the position of the thimble 5240, thereby controlling the degree of movement of the valve. It will be appreciated that the thimble 5240 can be used on the exhalation valves described herein with respect to the face mask.

The valve body 5130 also includes a gas valve assembly 5300 that is disposed within the conduit member (leg) 5140. The gas valve assembly 5300 includes a valve seat 5310 that is disposed within conduit member 5140 and is securely attached to the valve body 5130. The valve seat 5310 can be a spoke-like structure with a plurality of openings formed between the spokes and also includes a valve retention knob (protrusion) or the like 5312 extending outwardly therefrom. A gas valve 5320 is mated to the knob 5312 (by reception of the knob 5312 within an opening in the valve) and lies over the valve seat 5310. As best shown in FIG. 85, the gas valve 5320 is positioned proximate to the interface between the leg 5140 and the single conduit 5135 and is thus located above the over-inflation valve assembly.

The gas valve assembly 5300 serves as an inhalation valve that opens upon inhalation.

The valve body 5130 also includes a side gas port assembly 5400 that permits a gas, of variable concentration, to be delivered into the leg 5140 at a location below the gas valve assembly 5300. The side gas port assembly 5400 has a hollow side port body 5410 that extends outwardly from the side of the leg 5140. The side port body 5410 includes an air entrainment window 5415 formed therein to allow fluid flow into the hollow interior thereof. The side gas port assembly 5400 is similar to or identical to the second gas port 4740 and therefore, is of an adjustable type in that it includes a rotating shutter 5420 that is rotatably coupled to the side port body 5410.

As shown, the rotating shutter 5420 can be in the form of cap-like structure that is received on the open end of the side port body 5410. The shutter 5420 has an open end (which received the side port body 5410) and an opposite closed end. The shutter 5420 has a main section that has an air entrainment window 5422 formed therein. The air entrainment window 5422 extends circumferentially about a portion of the shutter. The air entrainment window 5422 is formed at a location on the shutter 5420 such that it overlaps (is in registration) with the window 5415 of the side port body 5410 and preferably, the dimensions of the window 5422 are greater than the dimensions of the window 5415.

A (barbed) gas port member 5430 that extends radially outward from the closed end of the shutter 5420 and also is formed internally within the shutter 5420. The internal section of the member 5430 serves as a gas injection orifice that directs the gas into the hollow interior of the body 5410. The open end of the internal section of the member 5430 is located preferably in-line with the windows 5415, 5422 since the internal section is physically received within the hollow interior of the side port body 5410.

Similar or identical to the shutter 4650, the shutter 5420 also includes a gas concentration pointer 4767 that extends outwardly from (and beyond) the open end of the shutter 5420. The body 5410 or some other proximate structure includes gas concentration indicator markings (similar to markings 4769) that are formed thereon. As the user rotates the shutter 5420, the degree of registration between the windows 5415, 5422 changes (between a fully open position and a fully closed position, as well as intermediate, partially open states). To change the concentration of the gas being delivered through the side gas port, the user simply adjusts the shutter 5420 and thereby changes the amount of air entrainment that occurs. In the fully open position of the shutter, more air is entrained with the gas flow and therefore, the concentration of the gas (e.g., oxygen) that is delivered to the patient is lower.

What is claimed is:

1. A patient interface device for delivering a gas to a patient comprising:
   a main body for placement against a face of the patient, the main body including a conduit portion that is open at a first end to a hollow interior of the main body and a free second end for attachment to another object in a sealed manner;
   at least one exhalation valve assembly that is disposed within a first port formed in the main body and includes an exhalation valve member that is configured to vent exhaled air when open;
   a primary inhalation valve assembly that is disposed within the conduit portion and includes a primary valve member that moves between open and closed positions;
   a secondary inhalation valve assembly that is disposed within a second port formed in the main body and includes a secondary valve member that moves between open and closed positions; and
   a mask valve assembly which includes a body in which the exhalation and secondary inhalation valve assemblies are disposed and for receipt within the main body, the body of the mask valve assembly including a first locator member which mates with a complementary second locator member formed in the conduit portion for coupling the mask valve assembly to the conduit portion;
   wherein the body includes an HME (heat moisture exchange) seat for receiving an HME unit and being located in relationship to the least one primary inhalation valve assembly and the at least one exhalation valve assembly to: (1) allow passage of inhaled gas, that flows through the primary inhalation valve assembly, through the HME seat before flowing into the hollow interior of the main body and to the patient and (2) allow passage of exhaled gas from the patient through the HME seat before exiting to atmosphere through the at least one exhalation valve assembly, wherein the HME seat is at least partially defined by a wall that is integral to the main body and defines a hollow space for receiving the HME unit, the wall being constructed for mating with the HME unit for the secure, yet releasable, attachment of the HME unit to the HME seat.

2. The patient interface device of claim 1, wherein the primary inhalation valve assembly has a first flow resistance associated therewith and the second inhalation valve assembly has a second flow resistance associated therewith which is greater than the primary inhalation valve assembly and as a result, the secondary inhalation valve assembly acts as an emergency inhalation valve.

3. The patient interface device of claim 1, wherein the at least one exhalation valve assembly includes a pair of coaxial exhalation valve assemblies formed in coaxial first and third ports formed in the main body.

4. The patient interface device of claim 1, wherein an axis extending centrally through the first port is perpendicular to an axis extending centrally through the second port.

5. The patient interface device of claim 1, wherein the primary inhalation valve assembly is constructed such that in an open position thereof, the primary valve member thereof moves such that a flow passage defined within the conduit portion is at least substantially open and substantially free of occlusion by the valve member.

6. The patient interface device of claim 5, wherein the primary valve member of the primary inhalation valve assembly is a swing valve which includes a base section that includes a bore formed therein that receives an elongated pin and the conduit portion includes a cradle for capturing ends of the pin such that the swing valve rotates between the open and closed positions.

7. The patient interface device of claim 6, wherein the primary valve member of the primary inhalation valve assembly has two different degrees of rotation in that the elongated pin rotates within the structure of a valve seat and the swing valve can independently rotate about the elongated pin.

8. The patient interface device of claim 1, wherein the primary valve member is disposed eccentrically relative to the conduit portion in which the primary valve member is disposed.

9. The patient interface device of claim 1, wherein the conduit member includes a secondary gas port formed therein at a location below the primary inhalation valve assembly.

10. The patient interface device of claim 1, wherein the body of the face mask assembly includes a retention post for retaining a pin about which a valve member of the primary inhalation valve assembly rotates.

11. The patient interface device of claim 1, wherein the at least one exhalation valve includes a valve seat and the exhalation valve member that is coupled to a mounting post that is formed as part of the valve seat and wherein excursion of the exhalation valve member is controlled by a thimble that is adjustably disposed on the mounting post, with the exhalation valve member being disposed between the thimble and the valve seat.

12. The patient interface device of claim 11, wherein the thimble is set on the mounting post at a position such that a target distance from an underside of the thimble to the exhalation valve member is achieved, thereby controlling a degree of which the exhalation valve member can open.

13. The patient interface device of claim 1, wherein the main body comprises a face mask and the conduit portion extends downwardly from a front portion of the main body, the free second end of the conduit portion being disposed below a bottom edge of the face mask.

14. A patient interface device for delivering a gas to a patient comprising:
   a main body for placement against a face of the patient, the main body including a conduit portion that is open at a first end to a hollow interior of the main body and a free second end for attachment to another object in a sealed manner;
   at least one exhalation valve assembly that is disposed within a first port formed in the main body and includes an exhalation valve member that is configured to vent exhaled air when open;

a primary inhalation valve assembly that is disposed within the conduit portion and includes a primary valve member that moves between open and closed positions; and a secondary inhalation valve assembly that is disposed within a second port formed in the main body and includes a secondary valve member that moves between open and closed positions;

wherein the body includes an HME (heat moisture exchange) seat for receiving an HME unit and being located in relationship to the least one primary inhalation valve assembly and the at least one exhalation valve assembly to: (1) allow passage of inhaled gas, that flows through the primary inhalation valve assembly, through the HME seat before flowing into the hollow interior of the main body and to the patient and (2) allow passage of exhaled gas from the patient through the HME seat before exiting to atmosphere through the at least one exhalation valve assembly, wherein the HME seat is at least partially defined by a wall that is integral to the main body and defines a hollow space for receiving the HME unit, the wall being constructed for mating with the HME unit for the secure, yet releasable, attachment of the HME unit to the HME seat;

wherein the HME unit is disposed within the HME seat such that the HME unit is securely attached to the main body but also can be readily removed therefrom, the HME unit having a base structure that contains HME media, the base structure having a first wall which contains the HME media and a flange structure that extends outwardly from the first wall so as to define a space, the wall of the HME seat being received within the space so as to couple the HME unit to the HME seat.

15. The patient interface device of claim 14, wherein the flange structure includes a finger hold for removing the HME unit from the HME seat.

16. A patient interface system for delivering a gas to a patient comprising:

a patient interface device for delivering the gas to the patient comprising:

a main body for placement against a face of the patient, the main body including a conduit portion that is open at a first end to a hollow interior of the main body and a free second end for attachment to another object in a sealed manner;

at least one exhalation valve assembly that is disposed within a first port formed in the main body and includes an exhalation valve member that is configured to vent exhaled air when open;

a primary inhalation valve assembly that is disposed within the conduit portion and includes a primary valve member that moves between open and closed positions; and a secondary inhalation valve assembly that is disposed within a second port formed in the main body and includes a secondary valve member that moves between open and closed positions; and a first accessory that is fluidly attached to the conduit portion;

wherein the primary inhalation valve assembly has a first flow resistance associated therewith and the second inhalation valve assembly has a second flow resistance associated therewith which is greater than the primary inhalation valve assembly and as a result, the secondary inhalation valve assembly acts as an emergency inhalation valve;

wherein the first accessory comprises a reservoir device having a flexible, expandable chamber and a connector that is fluidly connected to the conduit portion, the connector being defined by a body having a first gas port for connection to a gas source and a separate second gas port for connection to the gas source, wherein the second gas port includes a first air entrainment opening formed therein and a rotatable shutter having a second air entrainment opening formed therein is rotatably coupled about the second gas port, the first and second air entrainment openings defining an air entrainment window which is selectively open to atmosphere, the reservoir device being free of a valve member.

17. The patient interface system of claim 16, wherein the first gas port is located closer to a top open end of the connector compared to the second gas port and the shutter including a gas concentration pointer and the connector includes gas concentration indicator markings disposed vertically on an exterior surface of the connector, the gas concentration indicator markings corresponding to the gas concentration which is realized when the shutter is in a select position relative to the second part and the pointer is aligned with one of the gas concentration markings.

18. The patient interface system of claim 16, wherein the first accessory comprises a device selected from the group consisting of an MDI and a nebulizer.

19. The patient interface system of claim 16, wherein the conduit portion further has a secondary gas port formed therein at a location below the primary inhalation valve assembly and wherein in at least one operating state, a second accessory is fluidly attached to the secondary gas port, wherein at least one of the first and second accessories deliveries aerosolized medication and the other of the first and second accessories delivers a gas to the patient, wherein the gas and aerosolized medication communicate with one another upstream of the primary inhalation valve assembly.

20. The patient interface system of claim 19, wherein the second accessory comprises one of an MDI and a nebulizer device that delivers the aerosolized medication and the first accessory comprises a reservoir device that includes a connector for attachment to the conduit portion and at least one port for delivering the gas to the conduit portion and a chamber for storing the gas as well as the aerosolized medication when the primary inhalation valve assembly is closed during patient exhalation.

21. The patient interface system of claim 20, wherein the first accessory comprises a dual chamber reservoir device having separate first and second holding chambers, wherein the first holding chamber is for storing the aerosolized medication and the second holding chamber is in fluid communication with an external gas port that is connected to a gas source that delivers the gas.

22. The patient interface system of claim 21, wherein the external gas port includes an adjustable air entrainment window that is configured to alter a concentration of the gas by varying an amount of air that is entrained through the air entrainment window and mixes with the gas from the gas source.

23. The patient interface system of claim 22, wherein the connector of the reservoir device has first and second legs, the first leg being in fluid communication with the first holding chamber and the second leg being in fluid communication with the second holding chamber, the second leg containing an inhalation valve assembly that is positioned above the external gas port to permit the gas therefrom to only flow to the conduit portion when the inhalation valve assembly in the second leg is open.

\* \* \* \* \*